(12) United States Patent
Vargas

(10) Patent No.: US 9,173,734 B2
(45) Date of Patent: *Nov. 3, 2015

(54) INTRAGASTRIC IMPLANT DEVICES

(71) Applicant: IBIS Medical, Inc., Redwood City, CA (US)

(72) Inventor: Jaime Vargas, Redwood City, CA (US)

(73) Assignee: IBIS Medical, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/627,627

(22) Filed: Sep. 26, 2012

(65) Prior Publication Data

US 2013/0079603 A1 Mar. 28, 2013

Related U.S. Application Data

(60) Provisional application No. 61/539,814, filed on Sep. 27, 2011.

(51) Int. Cl.
*A61F 2/04* (2013.01)
*A61M 29/00* (2006.01)
(Continued)

(52) U.S. Cl.
CPC .............. *A61F 2/04* (2013.01); *A61B 5/14503* (2013.01); *A61B 5/14507* (2013.01);
(Continued)

(58) Field of Classification Search
CPC ....... A61F 5/0076; A61F 2/04; A61F 5/0036; A61F 5/0079; A61F 5/0089; A61B 5/14503; A61B 5/14507; A61B 5/14539; A61B 5/4238; A61B 5/6884; A61B 5/686; A61B 2560/0219; A61B 2560/028; A61B 2560/066; A61M 29/00

USPC .......................................... 604/8, 9; 606/191
See application file for complete search history.

(56) References Cited

U.S. PATENT DOCUMENTS 4,485,805 A 12/1984 Foster
4,648,383 A 3/1987 Angelchik
(Continued)

FOREIGN PATENT DOCUMENTS

WO 2004/017863 A2 3/2004
WO 2006/060049 A2 6/2006
WO 2010/074712 A2 7/2010

OTHER PUBLICATIONS

International Search Report and Written Opinion of the International Searching Authority issued in PCT/US12/57288 on Feb. 8, 2013, 14 pages.
(Continued)

*Primary Examiner* — Philip R Wiest
*Assistant Examiner* — Benjamin Klein
(74) *Attorney, Agent, or Firm* — Kilpatrick Townsend and Stockton LLP

(57) ABSTRACT

An intragastric anchor implant device with an elongate member having proximal and distal ends with atraumatic features disposed thereon is described herein. The atraumatic features inhibit damage to the tissues of the stomach and the gastrointestinal tract and help anchor the device. The elongate member may be substantially rigid to resist bending and engage a tissue of the stomach or gastrointestinal tract to prevent passage therethrough and may include one or more bends to conform to the shape of the tract. The anchor implant device may be coupled with a therapeutic device, such as an intestinal bypass sleeve with a sliding seal, such as an expandable structure, that secures the sleeve to direct a flow of food particles from the stomach therethrough, for use in treating various disorders, including obesity and diabetes. Methods of deploying the anchor implant devices are also disclosed.

40 Claims, 39 Drawing Sheets

(51) Int. Cl.
*A61B 5/145* (2006.01)
*A61F 5/00* (2006.01)
*A61B 5/00* (2006.01)

(52) U.S. Cl.
CPC ............ *A61B 5/4238* (2013.01); *A61B 5/6884* (2013.01); *A61F 5/0036* (2013.01); *A61F 5/0076* (2013.01); *A61F 5/0079* (2013.01); *A61F 5/0089* (2013.01); *A61M 29/00* (2013.01); *A61B 5/14539* (2013.01); *A61B 5/686* (2013.01); *A61B 2560/028* (2013.01); *A61B 2560/0219* (2013.01); *A61B 2560/066* (2013.01)

(56) References Cited

U.S. PATENT DOCUMENTS

| | | | |
|---|---|---|---|
| 4,694,827 | A | 9/1987 | Weiner et al. |
| 4,878,905 | A | 11/1989 | Blass |
| 4,899,747 | A | 2/1990 | Garren et al. |
| 4,925,446 | A | 5/1990 | Garay et al. |
| 5,306,300 | A | 4/1994 | Berry |
| 5,401,241 | A | 3/1995 | Delany |
| 5,820,584 | A | 10/1998 | Crabb |
| 5,868,141 | A | 2/1999 | Ellias |
| 6,629,987 | B1 | 10/2003 | Gambale et al. |
| 7,033,384 | B2 | 4/2006 | Gannoe et al. |
| 7,320,696 | B2 | 1/2008 | Gazi et al. |
| 7,803,195 | B2 | 9/2010 | Levy et al. |
| 7,892,214 | B2 | 2/2011 | Kagan et al. |
| 8,597,224 | B2 * | 12/2013 | Vargas ............................... 604/8 |
| 2002/0161341 | A1 | 10/2002 | Stinson et al. |
| 2003/0040804 | A1 | 2/2003 | Stack et al. |
| 2003/0040808 | A1 | 2/2003 | Stack et al. |
| 2003/0109935 | A1 | 6/2003 | Geitz |
| 2003/0199991 | A1 | 10/2003 | Stack et al. |
| 2004/0092974 | A1 | 5/2004 | Gannoe et al. |
| 2004/0267378 | A1 | 12/2004 | Gazi et al. |
| 2005/0049718 | A1 | 3/2005 | Dann et al. |
| 2005/0080431 | A1 | 4/2005 | Levine et al. |
| 2005/0096750 | A1 | 5/2005 | Kagan et al. |
| 2005/0192614 | A1 | 9/2005 | Binmoeller |
| 2005/0197714 | A1 | 9/2005 | Sayet |
| 2005/0228504 | A1 | 10/2005 | Demarais |
| 2005/0267596 | A1 | 12/2005 | Chen et al. |
| 2005/0273060 | A1 | 12/2005 | Levy et al. |
| 2006/0064120 | A1 | 3/2006 | Levine et al. |
| 2006/0142731 | A1 | 6/2006 | Brooks |
| 2006/0178691 | A1 | 8/2006 | Binmoeller |
| 2006/0190019 | A1 | 8/2006 | Gannoe et al. |
| 2007/0083271 | A1 | 4/2007 | Levine et al. |
| 2007/0149994 | A1 | 6/2007 | Sosnowski et al. |
| 2007/0198074 | A1 | 8/2007 | Dann et al. |
| 2007/0250020 | A1 | 10/2007 | Kim et al. |
| 2009/0118749 | A1 | 5/2009 | Shalon et al. |
| 2009/0187206 | A1 * | 7/2009 | Binmoeller et al. .......... 606/191 |
| 2009/0276055 | A1 | 11/2009 | Harris et al. |
| 2010/0049224 | A1 * | 2/2010 | Vargas ........................ 606/153 |
| 2010/0160933 | A1 | 6/2010 | Krueger et al. |
| 2010/0256775 | A1 | 10/2010 | Belhe et al. |
| 2010/0286628 | A1 | 11/2010 | Gross |
| 2011/0000496 | A1 | 1/2011 | Priplata et al. |
| 2011/0009690 | A1 | 1/2011 | Belhe et al. |
| 2011/0009980 | A1 | 1/2011 | Levy et al. |
| 2011/0040232 | A1 | 2/2011 | Magal |
| 2011/0046537 | A1 | 2/2011 | Errico et al. |
| 2012/0004676 | A1 | 1/2012 | Vargas |
| 2012/0116285 | A1 | 5/2012 | Duggirala |

OTHER PUBLICATIONS

International Search Report and Written Opinion of the International Searching Authority issued in PCT/US2011/030210 on May 27, 2011, 15 pages.
International Preliminary Report on Patentability issued in PCT/US2011/030210 on Oct. 11, 2012, 6 pages.
http://www.macmillandictionary.com/dictionary/american/rigid. Accessed Tuesday, Sep. 18, 2012.
First Office Action mailed Aug. 21, 2014, from Chinese Application No. 201180023065.2 (15 pages).
International Search Report and Written Opinion mailed Feb. 23, 2015, from International Application No. PCT/US2014/068457 (13 pages).

* cited by examiner

INTRAGASTRIC IMPLANT DEVICES

CROSS-REFERENCES TO RELATED APPLICATIONS

The present application is a non-provisional of, and claims the benefit of U.S. Provisional Patent Application No. 61/539,814, filed Sep. 27, 2011, the entire contents of which are incorporated herein by reference.

The present application is related generally to U.S. patent application Ser. No. 12/568,899, filed on Sep. 29, 2009, U.S. Provisional Patent Application No. 61/317,710 filed on Mar. 26, 2010 and U.S. Non-Provisional application Ser. No. 13/073,762 filed on Mar. 28, 2011, of which, the entire contents of each are incorporated herein by reference.

FIELD OF THE INVENTION

The present invention relates generally to medical devices, system and methods. Exemplary embodiments provide devices, systems, and methods for anchoring a treatment or diagnostic device in the stomach of a patient. Specific embodiments provide devices, systems, and methods for anchoring a therapeutic device in the stomach of a patient for the treatment of obesity, diabetes, hypertension, and/or other metabolic related disorders.

BACKGROUND OF THE INVENTION

Obesity and other metabolic related disorders affect millions of patients, and the number of patients suffering from such disorders has increased in recent years. Morbid obesity is often considered a serious and potentially life threatening disorder, as it may lead to diabetes, hypertension and other serious medical conditions. Since all of these disorders are typically related to the digestive processes, treatment methods often involve interrupting the normal digestive process to reduce the absorption of food particles passing from the stomach through the gastrointestinal system. Studies have also shown that reducing intestinal contact with gastric chyme, which may influence the secretion of certain hormones such as ghrelin which may stimulate hunger, may also be a viable treatment for obesity and its associated medical conditions. Although bariatric surgical procedures, such as the Roux-en-Y gastric bypass and gastric sleeve resection, have proven beneficial, these procedures are highly invasive and typically involve removal of portions of the stomach, stapling or suturing, which generally result in permanent irreversible changes to the patient's digestive tract and carry a substantial risk of surgical complications or death.

Although more recently, endoscopic procedures have been developed to deliver less invasive therapies, such as the gastric bypass sleeve, into the a patient's gastrointestinal system, anchoring of such devices has proven difficult as the stomach and gastrointestinal tract is fairly flexible and may contort significantly during digestion. Additionally, the harsh digestive environment within the stomach can tend to break down foreign objects, such as an anchoring device, when placed in the stomach for any length of time. The unique anatomy of the stomach also presents challenges in anchoring a treatment device as devices large enough to resist passage from the stomach through the gastrointestinal tract may block the passage of nutrients and food particles through the digestive system, while devices small enough to allow passage of food and nutrients are often passed through the digestive system. Due to these difficulties in anchoring treatment devices in the stomach, many procedures still rely on invasive techniques, such as suturing or penetrating tissues.

In light of the above, it would be beneficial to provide improved devices, systems and methods for anchoring treatment, sensing and/or monitoring devices, and in particular anchoring of such devices in a stomach of a patient for use in treatment of obesity and other metabolic related disorders. It would be desirable to provide a device and method for anchoring a treatment and/or sensing device in a gastrointestinal tract or stomach of a patient that does not require suturing, stapling, or resection of tissue, while allowing the passage of nutrients and food particles through the digestive system. It would also be beneficial to provide systems and methods of treatment that allow for treatment of metabolic disorders by limiting intestinal contact with stomach chyme and stomach secretions thereby influencing secretion of certain hormones, both of which contribute to metabolic disorders including diabetes and obesity. It would be further beneficial to provide systems and methods that allow for passage of such devices through the gastrointestinal tract after treatment monitoring is complete. It is further desirable that such devices and methods are robust enough to withstand the harsh environment of the stomach while providing adequate anchoring in the unique morphology of the stomach.

BRIEF SUMMARY OF THE INVENTION

The present invention generally provides improved medical devices, systems and methods of treatment. Exemplary embodiments of these devices and techniques can be used to anchor a treatment device in a stomach of a patient, which is particularly useful in treating metabolic disorders such as obesity (and related disorders), diabetes, hypertensions, and the like. Such disorders may be treated by anchoring a sleeve placed in the gastrointestinal tract in the stomach so that the sleeve can reduce intestinal contact with and absorption of gastric chyme or stomach secretions, flowing from the stomach through the gastrointestinal tract. Advantageously, the present invention allows for anchoring of a treatment device, such as a bypass sleeve, in the stomach of a patient by engaging a wall of the stomach and/or the gastrointestinal tract at multiple locations, without the need for stapling, suturing, resection, or other invasive modification of the gastrointestinal system.

In one aspect, the invention comprises an anchor having an elongate element extending between a proximal end and a distal end and further having a proximal and distal atraumatic feature disposed at each end, wherein the anchor is attached to or supports a treatment or diagnostic device. Each of the proximal and distal atraumatic features are configured to inhibit tissue trauma when urged against a tissue of the stomach or the gastrointestinal tract, while the elongate element is sufficiently rigid so as to resist bending between the proximal and distal ends and is sufficiently long to inhibit advancement of the anchor around a bend of a proximal intestine, such as the proximal portion of the duodenum, when under anchoring loads. In any of the embodiments described herein, the anchor may include one or more expandable structures which may be incorporated into or separate from the proximal and distal atraumatic features. For example, the anchor may include an expandable structure disposed between proximal and distal atraumatic features, the distal atraumatic feature optionally comprising another expandable structure. The elongate element and one or more expandable structures, as well as any other components associated with the anchor, may be made from the same or differing materials, including but not limited to polymers and various metals, including stainless steel alloys and nickel-titanium.

In another aspect, the treatment device comprises an intestinal bypass sleeve having a lumen extending between a proximal opening and a distal opening, wherein the sleeve comprises a material substantially impenetrable to a flow of ingested matter, such as ingested nutrients and food particles, the flow being in contact with the walls of the stomach before passing into the lumen. The proximal opening of the lumen is supported by the anchor distally of the proximal end of the anchor so as to direct the flow of ingested matter from the stomach into the lumen thereby reducing contact of the ingested matter with the walls of the gastrointestinal tract. In an embodiment particularly useful in treating diabetes, the sleeve may prevent ingested matter from contacting a portion of the duodenum, thereby influencing production of certain hormones that affect diabetes, such as ghrelin, a hormone that stimulates hunger.

In many embodiments, the distal atraumatic feature is sized and configured to be advanced through a pyloric valve such that when implanted the distal feature is disposed distal of the pyloric valve and the proximal feature is disposed within the stomach. In other embodiments, the distal atraumatic feature may be disposed in a distal portion of the stomach and the proximal feature may also be disposed in the stomach albeit proximal of the distal feature. Typically, in embodiments where the treatment device includes a sleeve, the elongate element between the features at each end has a profile smaller than the sleeve, and optionally, the distal feature may radially support the proximal opening of the sleeve so that a majority of a flow of ingested food advancing around the anchor passes into the opening of the sleeve. In other embodiments, the anchor is attached to the treatment device, often a sleeve, by a tether or other such coupling structure and the proximal opening of the sleeve may be supported by a separate structure, such as a sliding seal, which supports the proximal opening of the seal, typically by exerting an outward radially force so as to seal the proximal end of the sleeve against a wall of the gastrointestinal tract or the stomach. Such seals and support members may include expandable rings or other expandable structures, such as those described herein. Preferably, the seal is slidable so as to allow atraumatic movement within the gastrointestinal tract or the stomach.

In some embodiments, one or both of the atraumatic features include expandable members having a collapsed configuration suitable for delivery through the stomach, such as in an endoscopic procedure, and an expanded configuration, so as to distribute anchoring loads to inhibit tissue damage by an end of the elongate element or member and may also prevent passage of the distal feature across the pyloric valve or to help maintain a position of the anchor. The expandable members may include balloons, rigid, or non-rigid members, expandable wire loop structures, sinusoidal-type structures, or any structures that may expand when released from a collapsed configuration, may be expanded by inflation, or by movement of a drawstring, by retraction of a constraining outer sheath, or other expanding mechanism. The distal atraumatic feature may include an expandable structure sized so as to substantially fill the duodenal bulb and support the proximal opening of the sleeve in a position nearest the pyloric valve.

In many embodiments, the elongate element is sufficiently long to prevent end-to-end rotation in the stomach so as to maintain a relatively stable position in the stomach for anchoring the treatment or diagnostic device. Typically, the elongate element is at least 10 cm in length. In a preferred embodiment, when the distal atraumatic feature is disposed in a proximal portion of the duodenum a proximal portion of the anchor engages a distal portion of the stomach wall such that engagement of a proximal and distal portion of the anchor with the tissues of the stomach or gastrointestinal tract prevent the anchor from passing from the stomach through the duodenum. In some embodiments, the length of the elongate element and the distal and proximal features are configured such that displacement of a longitudinal axis of the anchor is limited by the engagement of the proximal and distal portions of the anchor with tissues of the stomach and the gastrointestinal tract so as to substantially maintain a position of the anchor and to maintain a position of the sleeve, and/or the distal feature, thereby maintaining the position of the anchor as well as the flow of ingested matter from the stomach through the sleeve.

In many embodiments, the elongate element includes one or more sensors so as to allow for diagnostic procedures and/or medical monitoring. The elongate element may be sized so that the proximal atraumatic tip passed beyond the pyloric valve and sized so as to anchor at a point in the gastrointestinal tract distal of the pyloric valve, such as at the duodenal-jejunal juncture where the Ligament of Treitz produces a sharp, relatively fixed turn in the small bowel.

Also disclosed are methods for treating a patient having an obesity or diabetes related disorder using the claimed anchor implant. An exemplary method includes deploying an implant within a gastrointestinal tract of the patient so that a proximal end of an anchor of the implant is disposed in the stomach, wherein the anchor comprises an elongate element having a proximal end and a distal end, and an atraumatic feature disposed near each end; supporting a therapeutic device, such as a sleeve, with the anchor so that the sleeve extends along an intestine of the patient, and so that ingested matter enters a lumen of the sleeve from the stomach, the ingested matter being in contact with a wall of the stomach; inhibiting advance of the anchor around a bend of the intestine by engaging a proximal portion of the anchor against a distal surface area of the stomach and by engaging a distal portion for the anchor against a proximal surface area of the intestine and by resisting bending of the elongate element between the proximal and distal ends; and advancing a flow of the ingested matter, such as ingested nutrients and particles of food, along the intestine within the lumen of the sleeve.

These and other embodiments are described in further detail in the following description related to the appended drawing figures.

DETAILED DESCRIPTION OF THE INVENTION

Figure 1A:
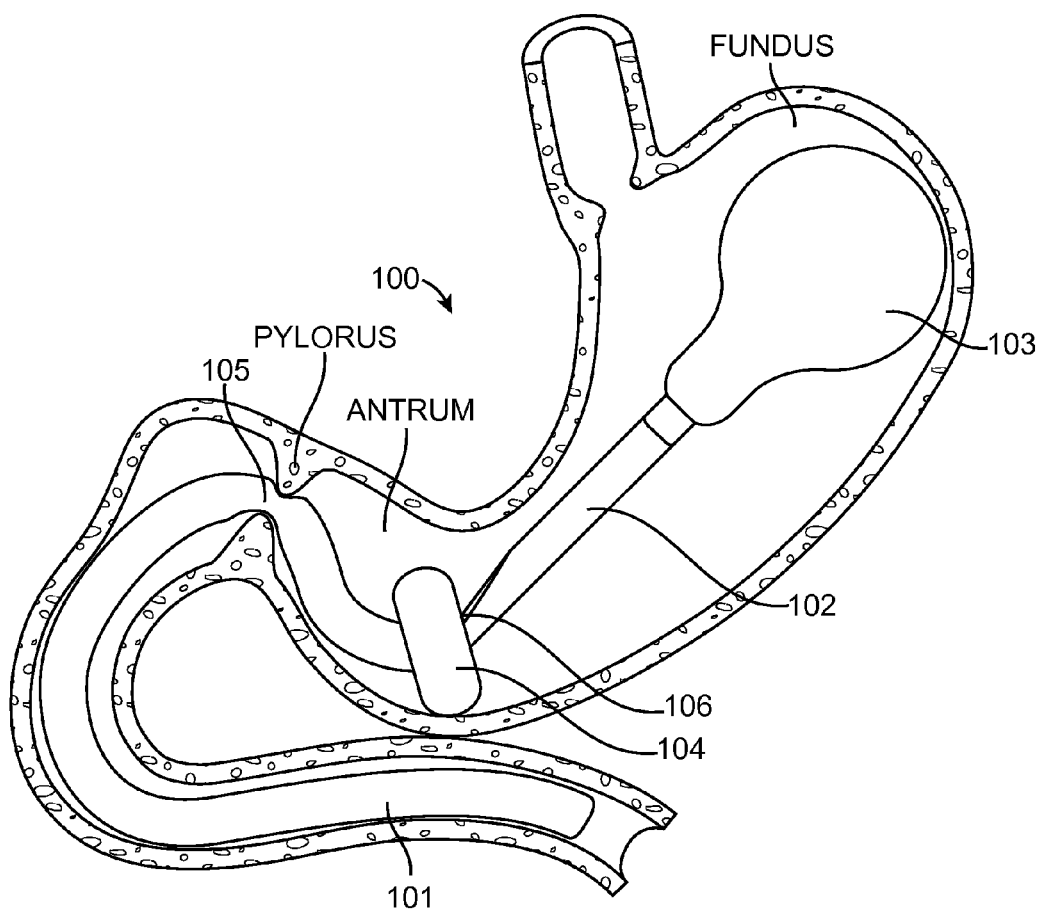
FIG. 1A is a view of a sectioned stomach and small bowel with an intragastric anchor implant, in accordance with many embodiments.

The present invention generally provides improved medical devices, system and methods for treatment of patients. As described herein, the term "proximal" means nearest the point of origin, within the context of the flow of food particles through the digestive system, and "distal" means situated farthest from the point of origin. For example, in reference to the stomach, a "proximal" portion of the stomach refers to the portion nearest the esophagus where the flow of food into the stomach originates, whereas the "distal" portion of the stomach refers to the portion nearest the pyloric valve where the flow of food particles leaves the stomach. Similarly, the "proximal" portion of the duodenum refers to the portion nearest the pyloric valve, from which the flow of food particles entering the duodenum originates.

Exemplary embodiments of the present invention can be used to anchor a treatment device in a stomach of a patient in treating metabolic related disorders such as diabetes, hypertension, and obesity (along with related disorders). Such treatments typically include anchoring a sleeve placed in the gastrointestinal tract in the stomach, such that the sleeve reduces the absorption of ingested matter flowing from the stomach through the gastrointestinal tract. Advantageously, the present invention allow for anchoring of a treatment device, such as a sleeve, in the stomach of a patient while still allowing sufficient flow of food and nutrients through the gastrointestinal tract via the sleeve without requiring stapling, suturing, resection, or other such invasive modification of the gastrointestinal tissues. The invention described herein exploits the geometry of the gastric and intestinal anatomy to maintain an intragastric implant in a relatively fixed position within the gastrointestinal tract without attachment to the gastric wall. Specifically, the present invention is directed to a gastric implant that comprises an intragastric anchor and a therapeutic or diagnostic device coupled to the anchor. The intragastric anchor of the invention limits the movements of a device attached to it to the displacement available to the anchor within the stomach and/or the duodenum.

In one embodiment of the invention, the intragastric anchor has an elongate shape extending along the long axis of the stomach from the antrum to the fundus such that displacement of the anchor along the long axis due to gastric contractility or other causes is limited by the gastric anatomy of the fundus and pylorus. Similarly, the elongate anchor is configured to be longer than the transverse width of the stomach and thus too long to be flipped end over end within the stomach by gastric contractility. Thus, the intragastric anchor provides a relatively stable platform on which to anchor bariatric or other therapeutic or diagnostic devices. Once deployed within the stomach, the anchor is configured to be larger than the pyloric valve to prevent its passing out of the stomach and into the small bowel. This configuration enables the intragastric anchor to maintain a relatively fixed position and orientation within the gastrointestinal tract. The present invention is further directed to a method for anchoring a therapeutic device or a diagnostic device within the stomach in a relatively fixed position, that is with a relatively stable position and orientation, while being free from attachment to the stomach wall, the method comprising positioning an anchor according to the invention in the stomach of a patient between the fundus and the pyloric valve and coupling a therapeutic device or a diagnostic device to the anchor.

In another embodiment, the intragastric anchor has an elongate shape extending from the antrum through the pylorus to the duodenum such that displacement of the anchor along the long axis due to gastric or intestinal motility or other causes is limited by the anatomy of pylorus and proximal duodenum. Similarly, the elongate anchor is configured to be longer than can be accommodated by the relatively fixed curvature of the proximal duodenum. Thus configured a transpyloric intragastric anchor is too long to be fully passed out of the stomach and into the small bowel and may serve as a relatively stable platform on which to anchor bariatric or other therapeutic or diagnostic devices within the gastrointestinal tract. Once deployed across the pylorus, a narrow portion of the anchor is configured small enough, typically 5 mm or smaller, to allow food particles and nutrients to pass around the anchor through the pylorus and into the duodenum. This configuration enables the transpyloric intragastric anchor to maintain a relatively fixed position and orientation within the gastrointestinal tract without compromising the flow of nutrients out of the stomach. The present invention is further directed to a method for anchoring a therapeutic device or a diagnostic device within the stomach in a relatively fixed position, that is with a relatively stable position and orientation, while being free from attachment to the stomach wall, the method comprising positioning an anchor according to the invention across the pylorus of a patient between the antrum and the duodenum; and coupling a therapeutic device or a diagnostic device to the anchor.

Having secured the anchoring implant within the gastrointestinal tract, any number of devices may be attached to it. In one embodiment, the device is a therapeutic device. For example, a bypass sleeve may be secured to extend from the esophagus to the jejunum, supported by a relatively fixed intragastric anchor. Having secured the anchoring implant within the gastrointestinal tract, any number of devices may be attached to it. In one embodiment, the device is a therapeutic device. For example, a bypass sleeve may be secured to extend from the body of the stomach to the jejunum, supported by a geometrically-fixed intragastric anchor. Similarly, a duodenal-jejunal bypass sleeve extending from the duodenal bulb into the jejunum may be supported by such an anchor. Also similarly, devices restricting gastric inflow and/or outflow may be supported by an intragastric anchor.

Similarly, diagnostic devices, such as for example a pH sensor, may be supported within the gastrointestinal tract by an intragastric anchor. By way of example, when configured to maintain a pH sensor within the duodenum, an intragastric anchor may include a duodenal extension, extending from the body of the anchor through the first bend of the duodenum and to the ampulla of Vater to support the sensor in a relatively fixed position within the intestine. To minimize the risk of ductal blockage the sensor is preferably allowed some degree of motion within the small bowel. Furthermore, since the intragastric anchor will move in a restricted fashion in response to normal gastric and intestinal motility and likewise move the pH sensor affixed to it, the pH sensor may be slidably coupled to the intestine by an atraumatic sliding apposition structure. Regular sliding along the intestinal wall reduces the possibility of hyperplastic tissue ingrowth, minimizes pressure on healthy mucosa, minimizes the likelihood of duct blockage, and enhances the removability of the sensor. The combination of elongate intragastric anchor and sliding apposition structure improves upon stenting, stapling, suturing, and other fixation methods for implanted diagnostic devices by avoiding the tendency of such implants to migrate or to become non-removable through tissue ingrowth and scarring.

In a preferred embodiment, the intragastric anchor revolves around bariatric therapy. A specific implementation described in this disclosure mimics the mechanisms by which Roux-en-Y gastric bypass surgery is thought to operate while advantageously avoiding the severe, invasive, and permanent surgical changes to the patient's anatomy associated with such procedures. An anchored bypass sleeve isolates a section of the small bowel from gastric chyme and secretions, delays exposure to digestive enzymes by bypassing the ampulla of Vater, and reduces nutrient absorption by bypassing a section of the small bowel.

Configured to secure an anchored bypass sleeve within the duodenum, the intragastric anchor may support the proximal opening of the sleeve in the duodenal bulb or duodenum distal to the pylorus, or in the antrum or body of the stomach proximal to the pylorus such that it is prevented from migrating distally into the small bowel. Since the intragastric anchor will move in a restricted fashion during normal gastric motility and will likewise move the bypass sleeve affixed to it, the proximal opening of the anchored bypass sleeve is preferably slidably coupled to the surrounding lumen by an atraumatic sliding seal. The combination of elongate intragastric anchor and sliding seal improves upon stenting, stapling, suturing, and other fixation methods by avoiding the tendency of gastrointestinal tract implants to migrate, cause perforations, or to become non-removable through tissue ingrowth and scarring.

One embodiment of an anchored bypass sleeve device includes a radially compliant proximal section of bypass sleeve extending from the duodenum to an intragastric anchor implant in the stomach. The radially compliant section of sleeve maintains outward radial pressure on the pylorus and aids in guiding food particles to the more distal portions of the sleeve. Radial compliance may be inherent in the construction of the proximal sleeve or it may be imparted by an expandable sleeve support such as a sinusoid or strut structure. The distal section of the bypass sleeve extends into the small bowel.

The anchored bypass sleeve is delivered to the target site via a prepositioned guidewire, in parallel with an endoscope, through an overtube slid over an endoscope, or with a flexible delivery enclosure. The device may include multiple radiopaque markers along its length to aid deployment under fluoroscopic guidance. For example, markers may be placed at the distal end of the bypass sleeve, at the distal end of the anchor, at the proximal end of the anchor, and at the sliding seal. Portions of the anchor such as the rigid element may be configured for relative radiopacity.

In a first specific aspect of the present invention, an intragastric anchor implant comprises an elongate anchor adapted to extend substantially from the fundus to the pyloric valve in a patient and a therapeutic or diagnostic device, such as a bariatric sleeve, coupled to the anchor. The elongate anchor will usually be adapted to remain positioned in the stomach without the need for suturing, stapling, or other forms of attachment. The length and geometry of the anchor will typically be selected to assure that the anchor remains within the stomach without being ejected through the pyloric valve or otherwise adversely affecting the patient. The therapeutic or diagnostic device will be either fixedly or movably coupled to the anchor, and may be coupled at one or more points. In the case of a bariatric sleeve, the bariatric sleeve will be configured to act in a manner similar or analogous to the Roux-en-Y gastric bypass, typically having a central passage with an upper or proximal opening positionable in the esophagus and a lower or distal outlet positionable in the intestines, or in some instances within the stomach. In any of the embodiments described herein, the anchor may have a variety of particular configurations and geometries: it may be either rigid, flexible, or have portions of each; it may be either straight, curved, include one or more bends, or have various other combinations of geometries; and/or it may comprise nestable or hinged links in order to have a shape-lock configuration which facilitates introduction and subsequent reconfiguration within the stomach. The elongate anchor will usually have upper and lower atraumatic ends or features, where the atraumatic end may be a bulbous geometry, a looped structure, or the like.

The bariatric sleeve will usually have a resilient sliding seal at its proximal end, which is adapted to slide against or slidably engage the inner wall of the esophagus. The sliding seal may be an inflatable balloon or cuff structure, or it may be a resilient flared structure, or it may be a stented structure to provide a resilient opening force, or the like. Usually, the bariatric sleeve will also slidably extend through the pyloric valve so that both the upper and lower ends of the sleeves may move within the gastroesophageal junction and pyloric valve as the stomach changes positions.

In another aspect of the present invention, a method for treating obesity comprises positioning an anchor across the pylorus of a patient. The anchor will typically be positioned between the antrum and the duodenal bulb and will usually be free from attachment to the intestinal or stomach wall. A bypass sleeve is coupled to the anchor, and the anchor positions a proximal opening of the sleeve in the antrum, duodenal bulb, or duodenum and a distal outlet of the sleeve in the small bowel. The proximal opening of the sleeve is preferably slidably disposed against a lumenal wall to guide food particles into the sleeve and inhibit food bypass.

FIG. 1A describes an intragastric anchor implant 100 supporting an intestinal bypass sleeve 101 that is substantially impenetrable to nutrients and food particles, in accordance with many embodiments. The sleeve is configured to line the intestine such that nutrients and food particles pass through the sleeve lumen and are prevented from contacting the intestinal wall while passing inside the sleeve. A preferred embodiment of the sleeve is configured to line the duodenum and proximal jejunum at least to the ligament of Treitz. Alternate embodiments may include shorter or longer bypass sleeves. An embodiment of the intragastric anchor implant includes proximal and distal atraumatic tips or features, 103 and 104 respectively, connected by a substantially rigid element 102. In an embodiment in which atraumatic features 103 and 104 are balloons, rigid element 102 may serve as a conduit to distribute pressurized fluid between the balloons as well as acting as preventing the anchor's passage out of the stomach in the event of accidental balloon deflation. A preferred embodiment of the rigid element is at least 10 cm long such that it will be unable to pass through the tight and relatively fixed turns of the proximal duodenum, although alternate embodiments may employ rigid elements that are shorter and longer than 10 cm. Some embodiments of the rigid element may be configured for substantial radiopacity such that the position of the rigid element within an anatomical lumen may be confirmed fluoroscopically. These embodiments may include barium, tantalum, gold, metallic particles, or any suitable radio-opaque material in their construction.

The embodiment of the intragastric anchor implant depicted in FIG. 1A is configured to geometrically limit movement of the distal atraumatic feature and sleeve opening relative to the pylorus by extending substantially between the antrum and fundus of the stomach. Although this embodiment includes a toroidal distal atraumatic feature 104 which supports and holds open the proximal sleeve opening 106, alternate embodiments may include U-shaped distal features, multiple balloons, or any other suitable form which includes a space which holds open the proximal end of an intestinal bypass sleeve and be connects it to the anchor implant 100.

The distal atraumatic feature is configured to be engaged by peristaltic action of the antrum such that it is pulled towards the pylorus while being sufficiently large, approximately 25 mm in diameter although larger and smaller configurations are possible, not to pass through the pylorus. A proximal portion 105 of the intestinal bypass sleeve 101 is configured to slidably engage the gastrointestinal tract such as one or more of the pylorus, bulb of the duodenum, duodenum, and jejunum. The proximal portion of the intestinal bypass sleeve may be configured to retain sufficient compressive strength to slide back and forth through the pyloric valve as gastric peristalsis displaces the intragastric anchor implant within the stomach.

A preferable embodiment of a sleeve would include a portion that is capable of smoothly changing diameter to accommodate stomach and small bowel peristalsis as well as the opening and closing of the pyloric sphincter forming a seal such that food particles exit the stomach through the proximal opening 106 of the intestinal bypass sleeve 101. To achieve such compressive strength and the ability to change diameters a portion of the sleeve as shown in FIG. 3D may be constructed of a braided material embedded in an elastomer such as silicone, polyurethane, thermoplastic elastomer such as Santoprene, or any suitably compliant material. The braided material may be polypropylene monofilament, stainless steel, nickel-titanium alloy, fluoropolymer, or any suitable braid material. More preferably a braid-reinforced proximal portion of the sleeve may be configured to provide sufficient radial compliance to expand when the pyloric sphincter relaxes while exerting minimal surface pressure on the sphincter when it is closed. A bypass sleeve thus constructed will also offer significantly improved resistance to twisting and kinking along its length within the small bowel, preventing possible blockages.

The embodiment of an intragastric anchor implant depicted in FIG. 1 includes a toroidal distal atraumatic feature 104 angled with respect to the main axis of the anchor towards the pylorus such that the bypass sleeve exits the atraumatic feature more directly in the direction of the pylorus. Another embodiment of an intragastric anchor implant may include a distal atraumatic feature rotated 90 degrees such that its central axis is orthogonal to the main axis of the intragastric implant.

Figure 1B:
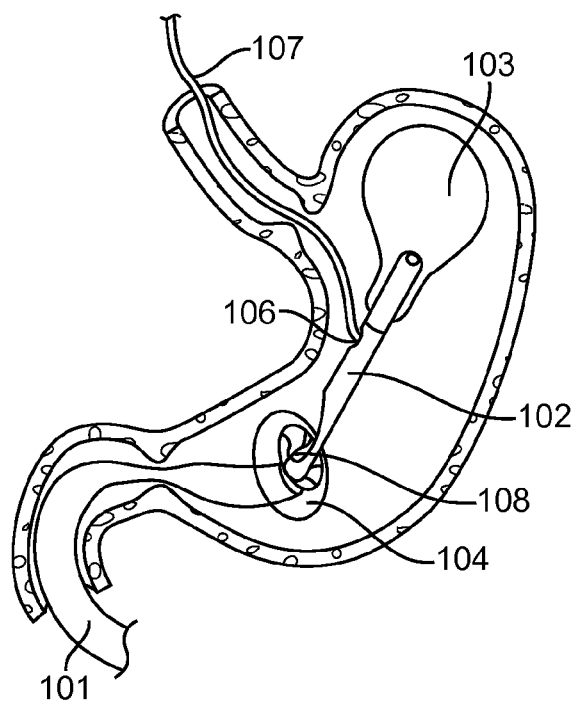
FIG. 1B is a view of a sectioned stomach and small bowel with an inflatable embodiment of an intragastric anchor implant and detachable fill-tube, in accordance with many embodiments.

FIG. 1B depicts an embodiment of an intragastric anchor implant supporting an intestinal bypass sleeve attached circumferentially to a substantially rigid element 102 which includes a lumen 108 to which bypass sleeve 101 is connected and through which chyme (partially-digested food particles) may pass. A rigid element 102 included in any embodiment of an intragastric anchor implant may include a one-way valve and port 106 through which air, carbon dioxide, saline, or another suitable fluid may be introduced via a fill tube 107 into proximal and distal atraumatic features 103 and 104 when configured as balloons.

Figure 1C:
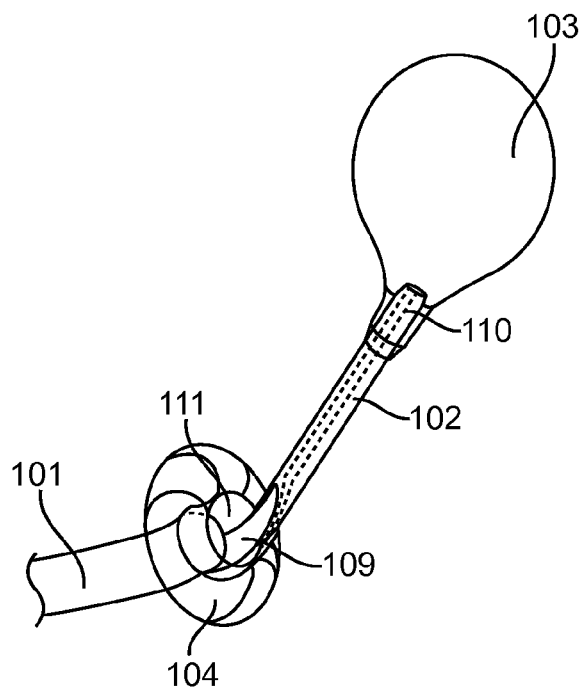
FIG. 1C is a view of an intragastric anchor implant with a rigid element conforming to an acutely-angled toroidal balloon, in accordance with many embodiments.

FIG. 1C depicts an embodiment of an intragastric anchor implant supporting an intestinal bypass sleeve 101 attached to the central opening 111 of a toroidal distal feature balloon 104 which is itself attached to a flattened, spoon-shaped section 109 of rigid element 102. The sleeve 101, balloon 104, and rigid element 102 may be attached with UV curing glue, silicone glue, RF welding, or any other suitable technique. The flattened-section 109 may extend proximally to make room for food particles to reach the mouth of the bypass sleeve 101. The rigid element may include a lumen 110 to serve as a conduit distributing pressure between the balloons. The sleeve opening supported by the distal balloon may be angled acutely relative to the main axis of the intragastric anchor implant.

Figure 1D:
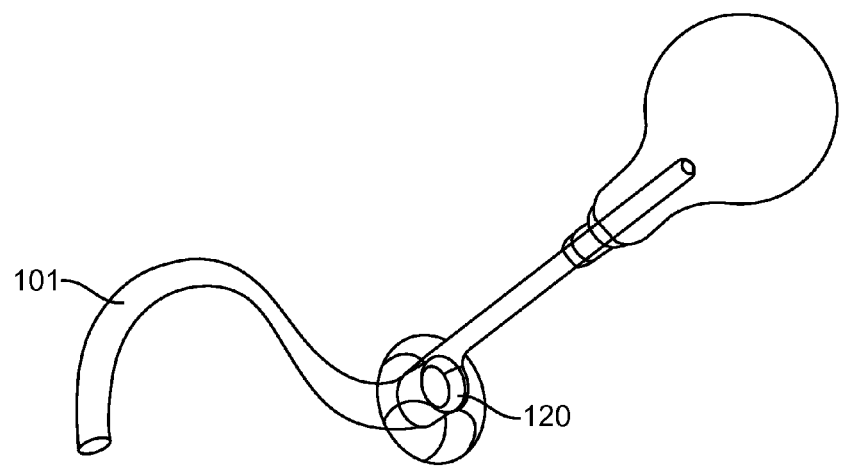
FIG. 1D is a view of an intragastric anchor implant with a rigid element conforming to an obtusely-angled toroidal balloon, in accordance with many embodiments.

FIG. 1D depicts an embodiment of an intragastric anchor implant supporting an intestinal bypass sleeve 101. The sleeve opening 120 supported by the distal balloon may be angled obtusely relative to the main axis of the intragastric anchor implant to separate the sleeve opening 120 from the rigid member and improve exposure of the sleeve opening to gastric peristalsis carrying food particles.

Figure 1E:
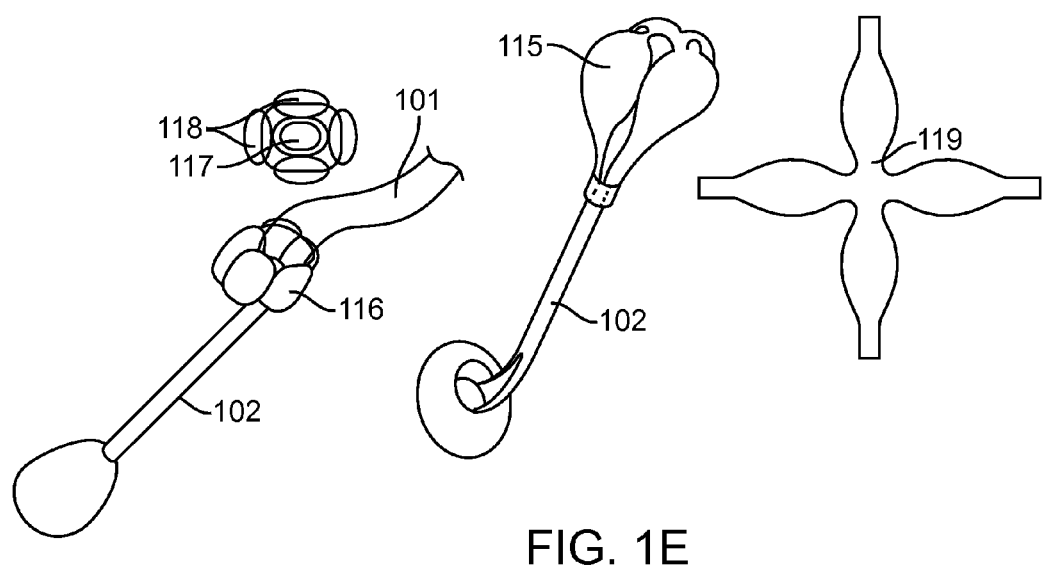
FIG. 1E depicts multi-chamber balloon configurations for intragastric anchor implants, in accordance with many embodiments.

FIG. 1E depicts various examples of embodiments of both the proximal 115 and distal 116 balloons configured to be manufactured by RF welding or similar techniques starting from a flat pattern 119 of multiple layers of material such as polyurethane thermoplastic. Chambers 118 in a distal balloon may be arranged around an intestinal bypass sleeve opening 117 such that they support it when inflated. Such balloons may be attached to a rigid element 102 via UV curing glue, heat-staking, or any other suitable attachment method.

Figure 2:
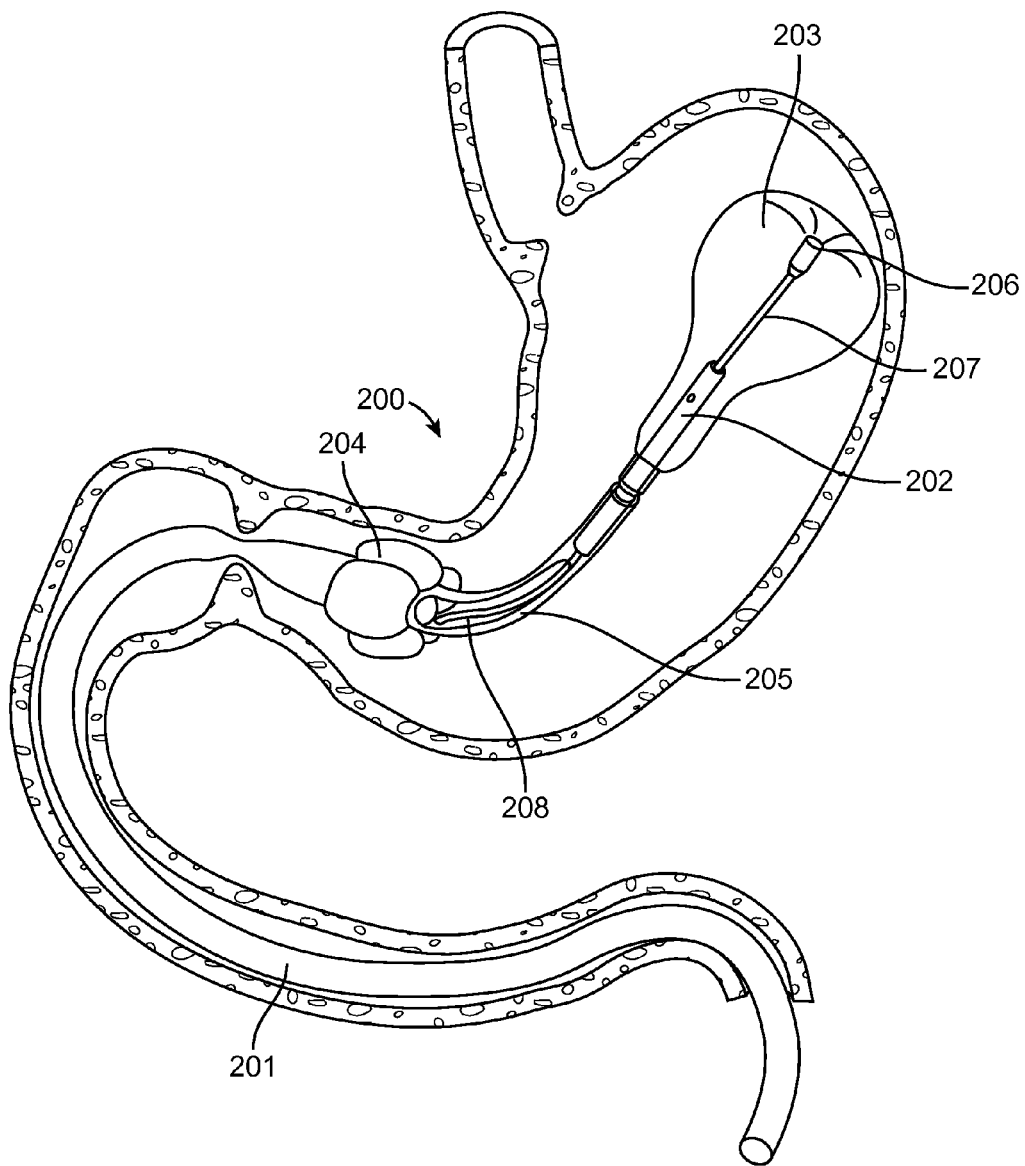
FIG. 2 is a view of a sectioned stomach and small bowel with an intragastric anchor implant with a flexible section between proximal and distal atraumatic features or tips, in accordance with many embodiments.

FIG. 2 depicts an embodiment of an intragastric anchor implant 200 with a flexible section 205 connecting distal and proximal atraumatic feature balloons, 204 and 203 respectively, supporting a therapeutic device, such as an intestinal bypass sleeve 201 as shown in this embodiment. The flexible section 205 may be constructed of flexible material such as elastomer, polymer, or fiber, or may be constructed with a hinge or plurality of hinged or linked joints. This flexible configuration allows the distal balloon 204 of an intragastric anchor implant 200 to rotate to face the pylorus, accommodating the curvature of the stomach, while the entire structure retains sufficient stiffness to limit the movement of the distal balloon and sleeve opening relative to the pylorus. The distal balloon 204 may include a smooth outer surface or it may be ridged and include several sub-chambers. A preferred embodiment of an intragastric anchor implant may include a fill-valve 206 connector for a detachable fill tube mounted on the proximal balloon. Flexible connecting tubes 207 and 208 may connect the fill-valve to rigid element 202 and distal atraumatic feature 204.

Figure 3A:
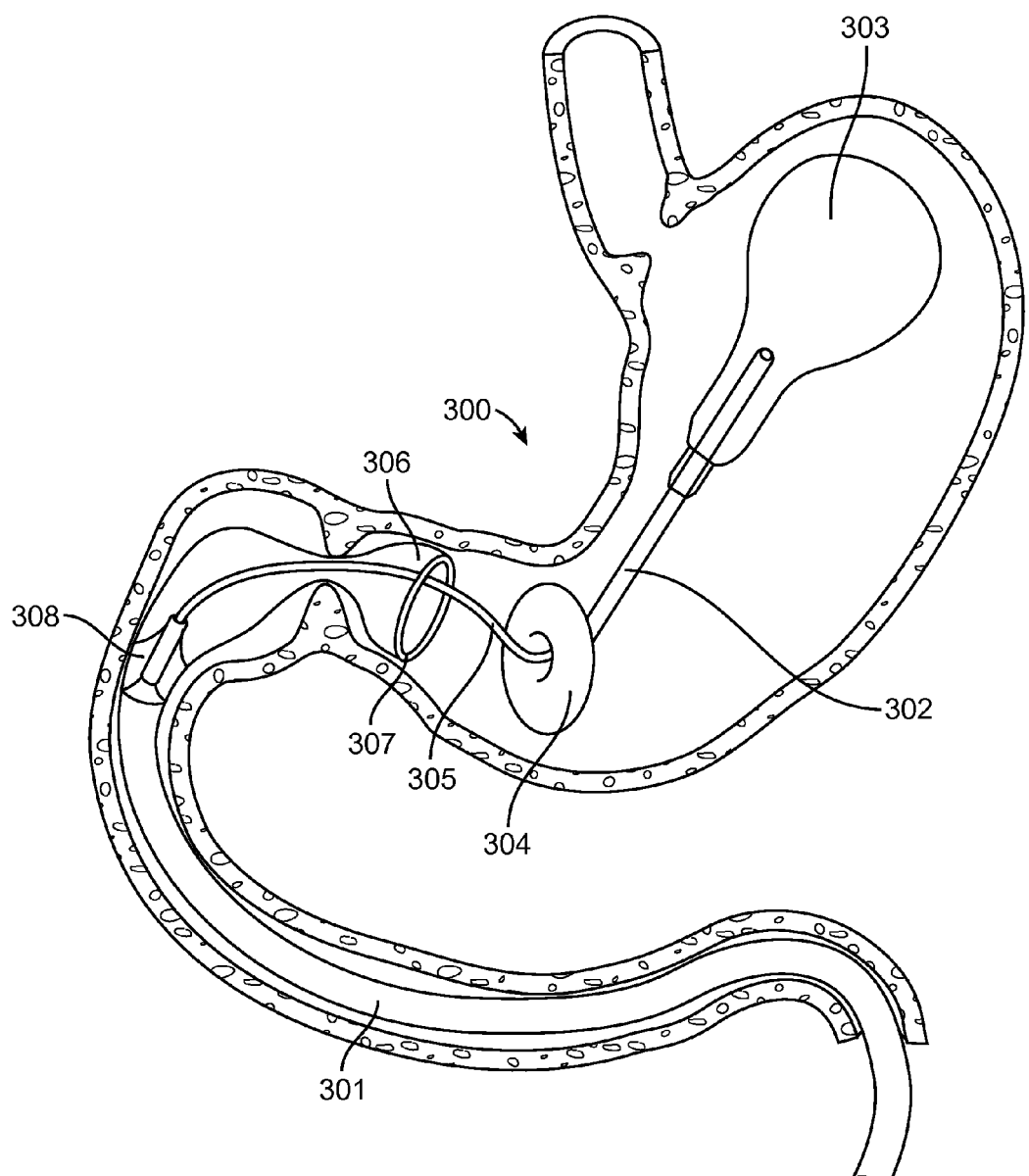
FIG. 3A is a view of a sectioned stomach and small bowel with an intragastric anchor implant supporting a sleeve with an antral opening via a flexible connector, in accordance with many embodiments.

FIG. 3A depicts an embodiment of an intragastric anchor implant 300 supporting an intestinal bypass sleeve 301 via a flexible connector 305. The flexible connector may connect the proximal end, outer surface, or inner surface of the bypass sleeve 301 to a rigid element 302 or to distal atraumatic feature 304. In a preferred embodiment the connector connects the rigid element 302 to the inner surface of the bypass sleeve at a point distal to the sleeve's sliding seal 306 via a coupling structure 308 such that the sleeve proximal opening is free to expand with sliding contact against the surrounding stomach, pylorus, or intestinal wall. In the embodiment depicted in FIG. 3A, the length of the flexible connector 305 and distance from the sleeve connection point are sized to maintain the sleeve opening in a variable but relatively constant position within the antrum portion of the stomach. In alternate embodiments, the connector length and connection point may be sized to maintain the position of a slidably-coupled sleeve opening within the pylorus, duodenal bulb, duodenum, or any advantageous position within the gastrointestinal tract. In the embodiment depicted in FIG. 3A, the proximal opening 306 of the bypass sleeve 301 is configured to slidably couple to the mucosal surface of the antrum such that substantial contact is maintained as the intragastric anchor implant is displaced within the stomach by gastric and intestinal motility. The friction of sliding contact may be reduced by coating a portion of the external surface of the bypass sleeve 301 with a hydrophilic polymer, parylene, or other suitable friction-reducing coating. In the embodiment depicted in FIG. 3A, the proximal opening of the bypass sleeve 301 is configured with a radiused edge 307 such that the sleeve presents an atraumatic surface compatible with sliding contact. Alternate embodiments may position a slidably coupled proximal sleeve opening within the duodenal bulb, duodenum, or any advantageous position within the gastrointestinal tract.

Figure 3B:
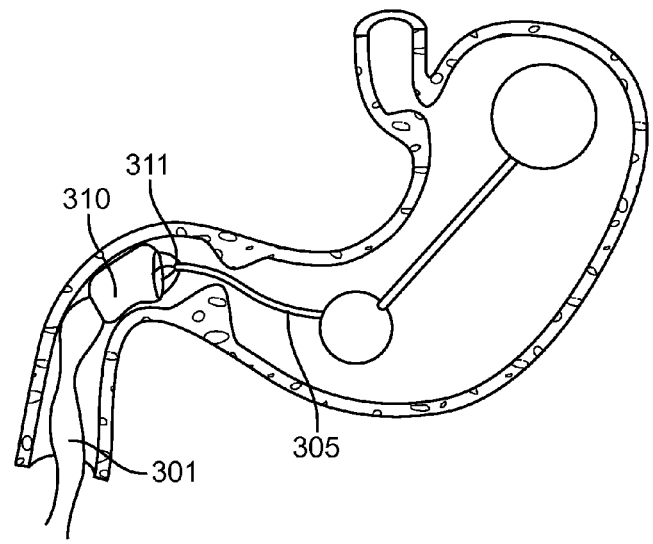
FIG. 3B is a view of a sectioned stomach and small bowel with an intragastric anchor implant supporting a sleeve with a duodenal opening via a flexible connector, in accordance with many embodiments.

FIG. 3B depicts an embodiment of an intragastric anchor implant supporting an intestinal bypass sleeve with a flexible connector 305. The connector may be constructed of a polymeric elastomer, fiber reinforced elastomer, polymer monofilament, or any suitable material. In this embodiment, a proximal portion 310 of the sleeve 301 is configured to be slidably coupled to the inner surface of the duodenum and the connector 305 attaches to the sleeve's proximal opening with a coupling element 311 leaving the opening substantially patent such that the passage of nutrients and food particles is substantially unimpeded. The coupling element may be an integrally molded part of connector 305 or may be constructed of nickel-titanium alloy or stainless steel wire struts, or any suitable material of sufficient strength to resist forces imparted by peristalsis while being sufficiently compressible to allow the bypass tube and anchor assembly to be delivered in a small diameter package.

Figure 3C:
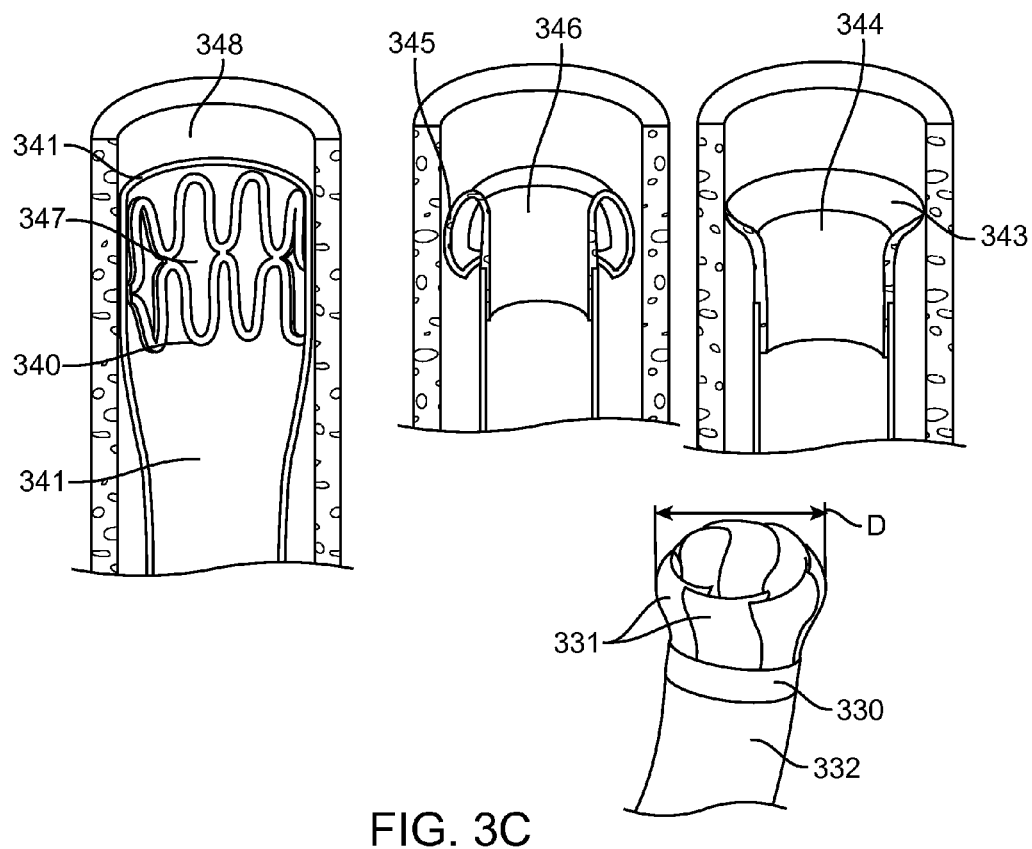
FIG. 3C depicts sliding seal embodiments for sleeves, in accordance with many embodiments.
Figure 3D:
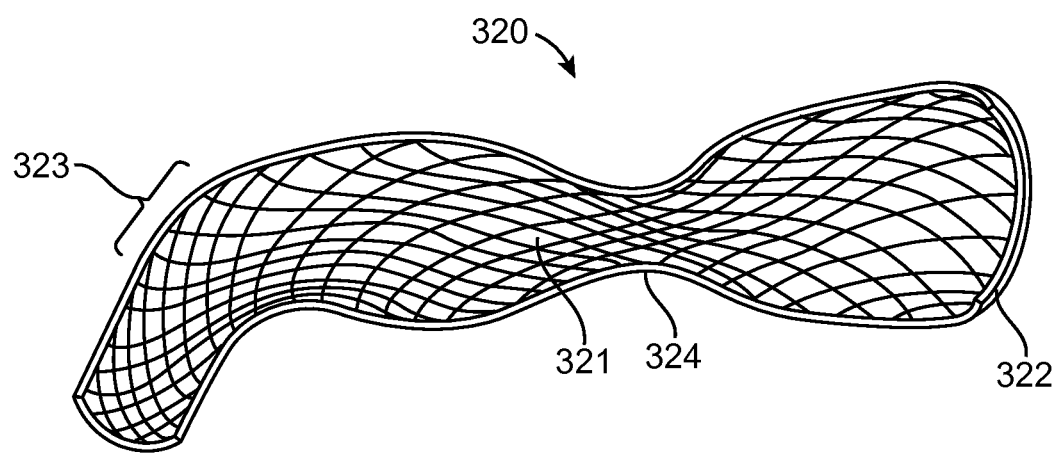
FIG. 3D depicts a sliding seal for sleeves with a composite structure, in accordance with many embodiments.

FIG. 3C depicts embodiments of a slidably coupled bypass sleeve 342 configured for atraumatic sliding upon the surface of an anatomical lumen while accommodating varying lumen diameters and shapes. In these embodiments, a sliding seal section of the intestinal bypass sleeve 342 is configured for substantial apposition against and atraumatic sliding upon the surface of anatomical lumen 348. In order for the opening of a bypass sleeve to conform to the internal topography of a section of the gastrointestinal tract, it may be configured to have a mechanical compliance similar to or less than that of the lumenal wall against which it will slide while at the same time generating enough outward radial pressure to maintain substantial apposition against that wall. This may be achieved with a stent-like structure, such as compressible ring 340, incorporated into the proximal sleeve which may also include a radiused proximal edge 341. The compressible ring 340 may include at least one sinusoidal element to allow compression and expansion such that outward radial pressure may be applied to an anatomical lumen so as to create a sliding seal when combined with a flexible circumferential tube 347 made of material such as polypropylene, fluoropolymer film or the like. The ring may be made of polymer such as polypropylene or fluoropolymer, nickel-titanium alloy, stainless steel, or any suitable material. An alternate embodiment of a sliding seal section of a bypass sleeve includes a radiused low durometer elastomeric cuff 345 attached to a bypass sleeve opening 346, Another alternate embodiment includes a tapered low durometer elastomeric wiper 343 attached to the proximal sleeve opening 344, or any suitable structure that provides appropriate compliance and sleeve apposition.

A preferred embodiment of a sliding seal, as shown in FIG. 3C, employs overlapping leaflets 331 attached to a coupling ring 330 which provides circumferential mechanical support and which may attach to intestinal bypass sleeve 332. The leaflets, while fixed to coupling ring 330 at their bases, may slide past one another along the rest of their lengths to increase or decrease the effective diameter of the sealing surface. The leaflets may be configured with outward curvature such that effective diameter D is larger than the diameter of the coupling ring and may interfere somewhat with an anatomical lumen to provide a slideably coupled seal. The leaflets may be made of flexible material such as thermoplastic elastomer, silicone, fluoropolymer, polypropylene, or any suitable material.

Figure 5:
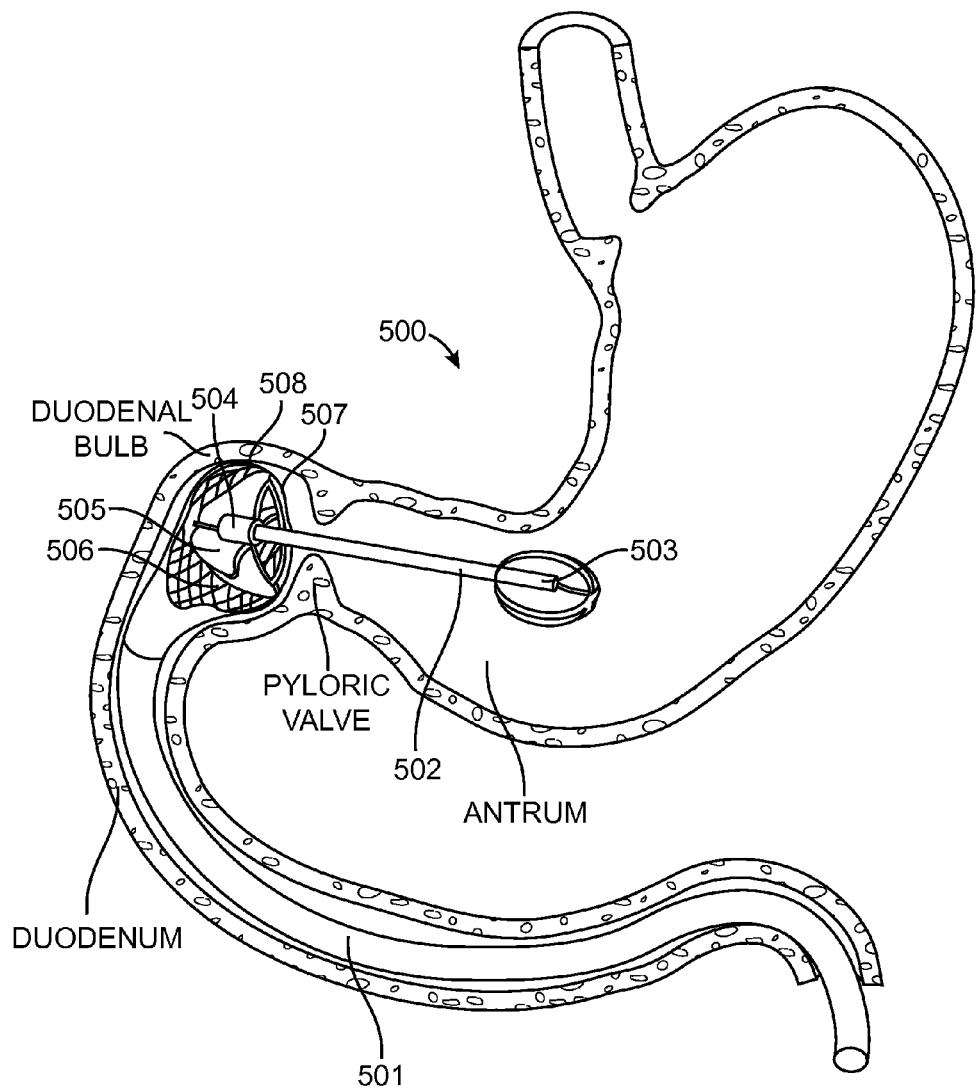
FIG. 5 is a view of a sectioned stomach and small bowel with an intragastric anchor implant with a rigid element passing through the pylorus, in accordance with many embodiments.

A preferred embodiment of a sliding seal section of intestinal bypass sleeve 320, which typically includes a proximal opening of the intestinal bypass sleeve, incorporates a compliant composite structure as shown in FIG. 3D and in FIG. 5 (in sectioned and partially-sectioned cutaway views, respectively) in which a fibers in a tubular braid 321 are embedded in an elastomeric matrix such as silicone rubber, polyurethane, thermoplastic elastomer such as Santoprene, or any suitable elastomeric matrix material. Such a structure enables a bypass sleeve of varying diameters to be constructed such that a larger diameter may form a duodenal or antral sliding surface while the entire structure may be contracted into a smaller diameter for delivery into a target site within the gastrointestinal tract, maintaining substantially smooth inner and outer surfaces. Similarly, a smaller diameter section forming a pyloric sliding surface 324 may be defined and set into the elastomeric composite structure, limiting the reaction force exerted on particular sections of the gastrointestinal tract. Sliding surfaces defined by the smaller diameter section may include pyloric and duodenal sliding surfaces. A relatively smaller diameter section at the proximal opening of the bypass sleeve may also be set into the elastomeric composite structure such that an atraumatic radiused edge 322 of a sliding seal is formed. Such an atraumatic leading edge may also be formed through molding, heat-setting, or any suitable process. A bend 323 may also be set into such an elastomeric composite structure such that the flexible sleeve tends to settle into specific bends in the gastrointestinal tract such as the first bend of the duodenum. Sliding surfaces constructed in this manner may also include a coating of hydrophilic polymer, parylene, or other suitable friction reducing coating.

Figure 4:
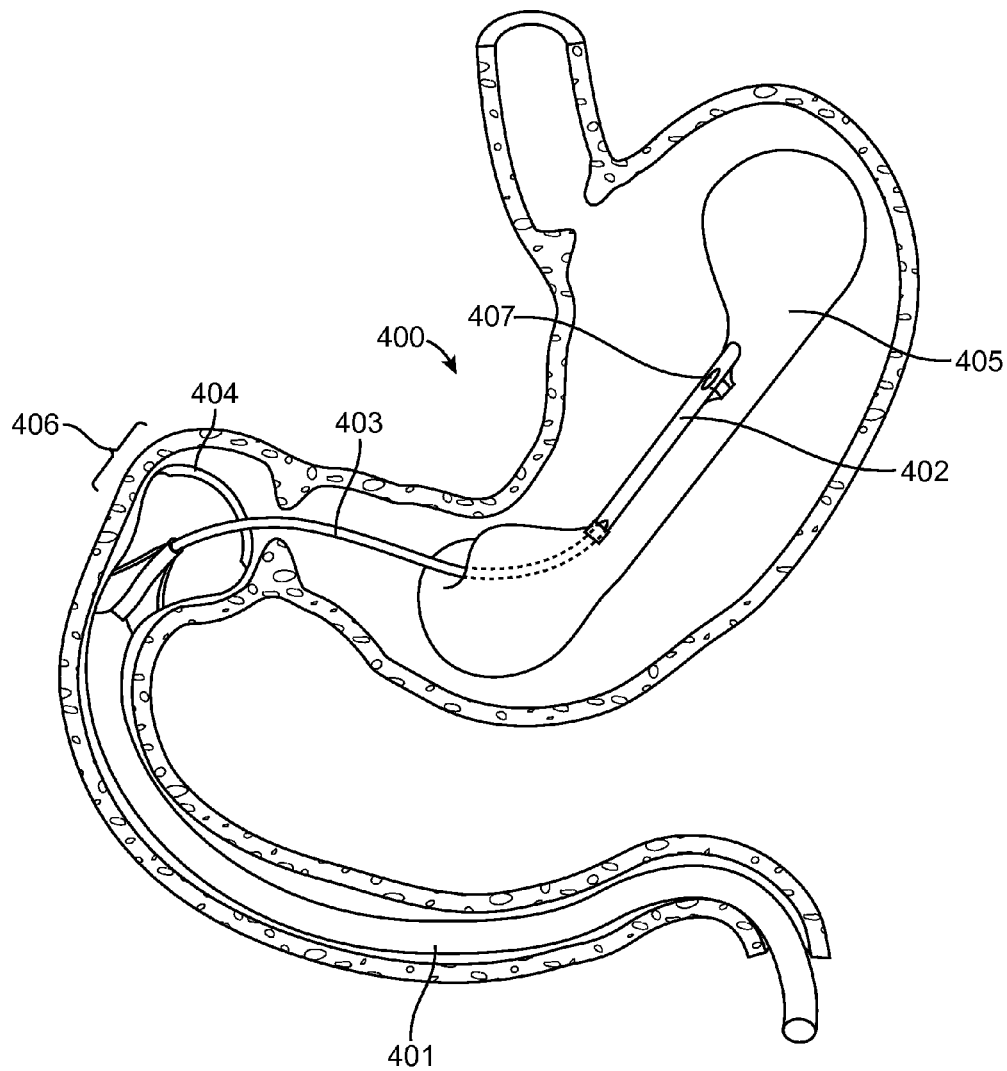
FIG. 4 is a view of a sectioned stomach and small bowel with an inflatable embodiment of an intragastric anchor implant, in accordance with many embodiments.

FIG. 4 depicts an embodiment of an inflatable intragastric anchor implant 400 supporting via a flexible tether 403 an intestinal bypass sleeve 401 having a proximal end (shown in sectioned cutaway view) configured as a sliding seal 406 with a curved opening edge 404 configured for sliding and positioned within and slidably coupled to the duodenal bulb and duodenum. As shown in FIG. 4, rigid element 402 may be attached to an outer surface of inflatable portion 405, although the rigid element may also be attached to an inner surface of the inflatable portion or in an intermediate position. The rigid element 402 and may include an inflation port 407 with a one-way valve to retain pressure within the implant. The rigid element is configured to be at approximately 10 cm long to prevent the intragastric anchor implant from exiting the stomach should the inflatable portion 405 deflate, although longer and shorter embodiments of the rigid element are possible. Tether 403 may connect directly to the rigid element as shown in FIG. 4, or alternately may connect to the inflatable portion.

FIG. 5 depicts an embodiment of an intragastric anchor implant 500 configured to position a substantially rigid element 502 through the pyloric valve such that it straddles the antrum and proximal duodenum and supports an intestinal bypass sleeve 501 that is substantially impenetrable to nutrients and food particles. The sleeve 501 is configured to line the intestine such gastric chyme passes through the sleeve lumen and is prevented from contacting the intestinal wall while passing inside the sleeve. A preferred embodiment of the sleeve is configured to line the duodenum and proximal jejunum, such as a 40 cm to 80 cm portion of the small bowel, at least to the ligament of Treitz. Alternate embodiments may include shorter or longer intestinal bypass sleeves. A preferred embodiment includes a rigid element 502 that is at least 10 cm long such that it will be unable to pass through the tight and relatively fixed turns of the proximal duodenum, although alternate embodiments may employ rigid elements that are shorter or longer. A preferred embodiment of the rigid element 502 is approximately 3 to 5 mm in diameter, although practicable embodiments of larger and smaller diameters are possible depending upon material selection. The rigid element 502 may be constructed of acid-resistant materials such as polypropylene, fluoropolymer, nickel-titanium alloy, stainless steel, or any suitable material. Some embodiments of the rigid element 502 may be configured for substantial radiopacity such that the position of the rigid element within a biological lumen may be confirmed fluoroscopically. These embodiments may include barium, tantalum, gold, metallic particles, or any suitable radio-opaque material in their construction. Since an intragastric anchor implant, although remaining in a relatively stable position, will be subject to movement imparted by gastric and intestinal motility it is advantageous for the rigid element 502 to have a substantially smooth and even surface such that it may slide relatively unimpeded against pyloric tissue. Alternate embodiments of the anchor may include a friction-reducing coating such as a hydrophilic polymer, parylene, or the like, on the outer surface of the rigid element 502 to reduce the possibility of mucosal erosions in the pylorus and surrounding tissues. The rigid element 502 is located between proximal and distal atraumatic features, 503 and 504 respectively, which spread the mechanical loads imparted by gastric motility over relatively large surface areas.

Figure 8:
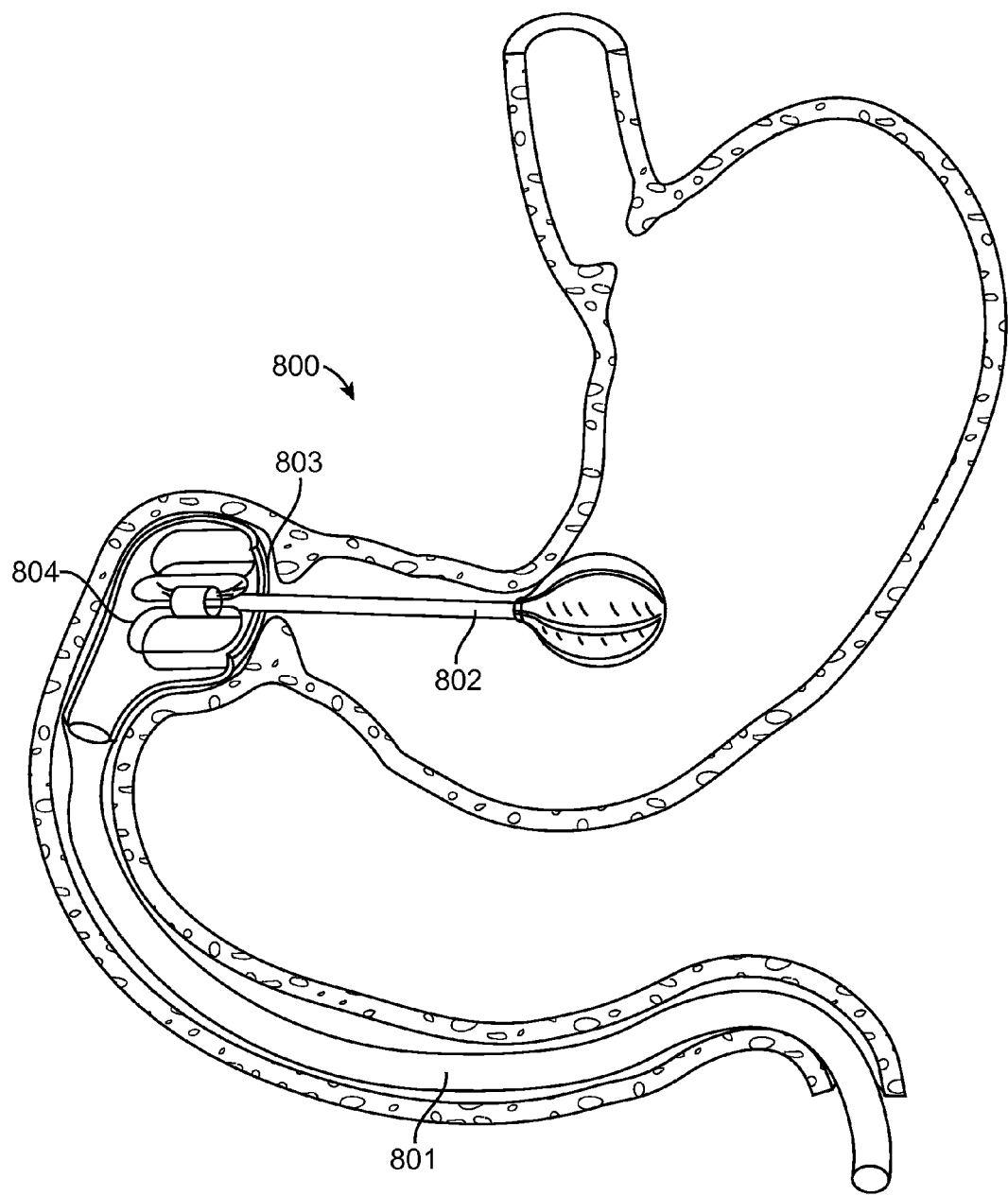
FIG. 8 is a view of a sectioned stomach and small bowel with an intragastric anchor implant with an atraumatic feature including loops, in accordance with many embodiments.

Embodiments of these atraumatic features, 503 and 504, may include pressurized fluid-filled balloons, or non-pressurized hollow or solid compliant projections including ribs, fins, rods, domes, bulbs, prismatic shapes, or other flexible features capable of spreading mechanical loads through mechanical deflection over a relatively large area. The compliant projections may be constructed of acid-resistant low durometer elastomer such as silicone rubber, polyurethane, Santoprene, and the like, or they may be constructed of loops, arcs, braids, or networks of polymer such as polypropylene or fluoropolymer or of springy metal such as superelastic nickel-titanium alloy or stainless steel. Wire embodiments of the atraumatic features may be encased in acid-resistant flexible membrane such as silicone elastomer, thermoplastic elastomer such as Santoprene, polyurethane, PTFE, and the like to protect tissue or they may be exposed, particularly in the case of a distal atraumatic feature 504 which may be contained within an intestinal bypass sleeve 501. Alternately the proximal and distal atraumatic features may be rigid as the proximal atraumatic feature 1003 depicted in FIG. 10B and configured to distribute mechanical loads over relatively large surface areas without substantially deforming. The proximal atraumatic feature resides in the stomach and serves to shield gastric tissue from the rigid element's proximal end. In the embodiment depicted in FIG. 5, the distal atraumatic feature 504 resides in the duodenal bulb or proximal duodenum and serves to connect the intragastric anchor implant to the bypass sleeve as well as shielding the small intestine from the distal end of the rigid element. The distal atraumatic feature may be configured to substantially fill the duodenal bulb as shown in FIG. 8 or to be suspended within the bypass tube's proximal opening, contacting the bypass tube only at a few connection points with fins 505 as shown in FIG. 5 or with struts 1006 as shown in FIG. 10B, or any suitable connection element.

The embodiment of the intestinal bypass sleeve shown in the partially-sectioned cutaway view in FIG. 5 is configured to slidably couple with the duodenum. As shown in FIG. 5, this coupling with the duodenal wall is achieved by a sliding seal 507 forming the proximal portion of the intestinal bypass sleeve 501 constructed with braid 506 embedded in silicone elastomer, thermoplastic elastomer such as Santoprene, or other suitable flexible matrix material set into a fully expanded state which is slightly larger in diameter than the expected diameter of the proximal duodenum or duodenal bulb. Compliance fins 505 may also provide radial expansion force to aid in coupling sliding seal 508 to an anatomical lumen. In an embodiment of the invention including a sliding seal made as a composite structure with braided fibers embedded in an elastomeric matrix, a contact zone of larger diameter than the majority of the intestinal bypass sleeve 501 and a curved proximal opening edge 507 configured for sliding may be defined in manufacturing. This larger diameter contact zone forms the sliding seal which maintains a constant gentle pressure against the intestinal wall such that the contact zone conforms to differences in diameter and shape as it slides back and forth within the duodenum in response to gastric and intestinal motility.

As shown in FIG. 5, a proximal section of an intestinal bypass sleeve may be pre-formed into an curved or bent configuration such that the proximal section of the sleeve will tend to settle into the first bend of the duodenum. A preferred embodiment includes a proximal portion of the bypass sleeve formed of flexible mesh or braided material 506 embedded in an elastomeric matrix such as silicone, polyurethane, thermoplastic elastomer such as Santoprene, or the like. The braid serves to maintain smooth, wrinkle-resistant bends and accommodates changes in diameter while also helping to spread the thrust load produced by stomach motility, such as peristalsis, acting upon the intragastric anchor implant.

Figure 6:
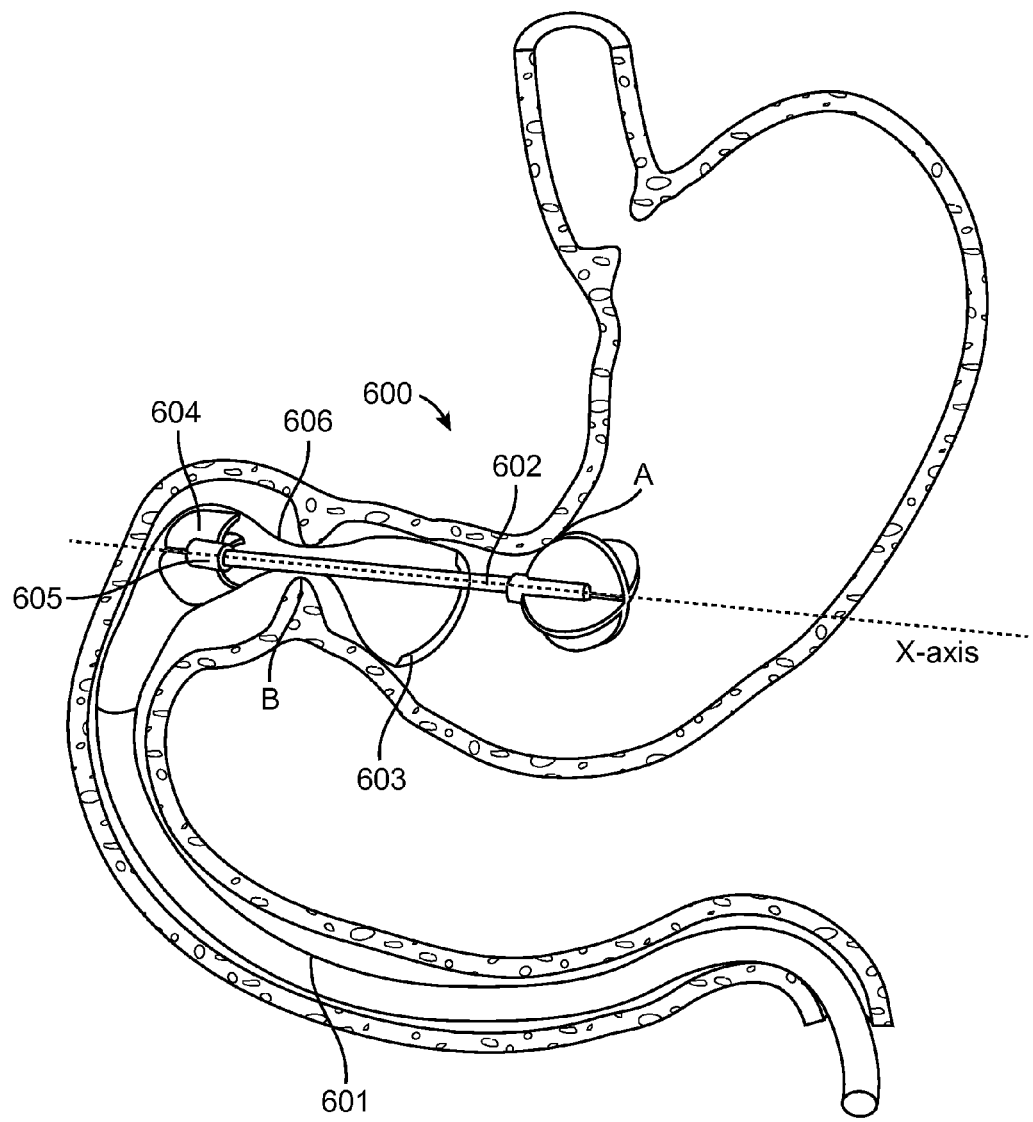
FIG. 6 is a view of a sectioned stomach and small bowel with an intragastric anchor implant with an antral sliding seal, in accordance with many embodiments.

FIG. 6 depicts an embodiment of an intragastric anchor implant 600 supporting an intestinal bypass sleeve 601 (shown in partially-sectioned view) with a proximal opening configured as a sliding seal 603 slidably coupled to the antrum and distal stomach. The intragastric anchor implant may include a rigid element 602 which may be coupled to the bypass sleeve 601 by flexible internal ribs 604 formed of elastomeric material such as Santoprene or silicone, flexible polymer such as polypropylene or fluoropolymer, metal such as nickel-titanium alloy, or any suitable compliant material. The elastomeric coupler serves as a distal atraumatic feature 605 for the end of the rigid element such that forces imparted by gastric and duodenal motility are broadly distributed to the duodenum. A radially compliant connecting structure 606 connects sliding seal 603 to atraumatic feature 605, passing through the pyloric valve with rigid element 602.

FIG. 6 further illustrates a mechanism by which this embodiment of the anchor implant, as well as many of the other embodiment described herein, substantially maintains its anchoring position within the stomach. As shown in FIG. 6, a distal portion of the anchor implant near the distal feature is engaged with the tissue at the pyloric valve at Point A and a proximal portion of the anchor, the proximal feature, is engaged with a distal portion of the stomach wall at point B such that a longitudinal axis of the anchor, the X-axis, is limited in its range of movement. By engaging a tissue of the patient with a proximal portion and a distal portion of the anchor, the movement of the anchor is limited such that the anchor is prevented from rotating to an angle that would allow the anchor to pass through the proximal duodenum. Additionally, the length of the elongate element may be sufficiently rigid to prevent bending or curvature that would allow passage of the element through the proximal duodenum. Thus, by engaging the tissues of the patient as described, the claimed implant and elongate element allow for anchoring without the use of invasive techniques such as suturing of tissues. Furthermore, as the above mechanisms limit the displacement of the longitudinal axis the anchor may be configured to maintain a desired angle or axis within the stomach so as to achieve a desired flow of ingested matter or optimal anchoring position for a given application.

Figure 7:
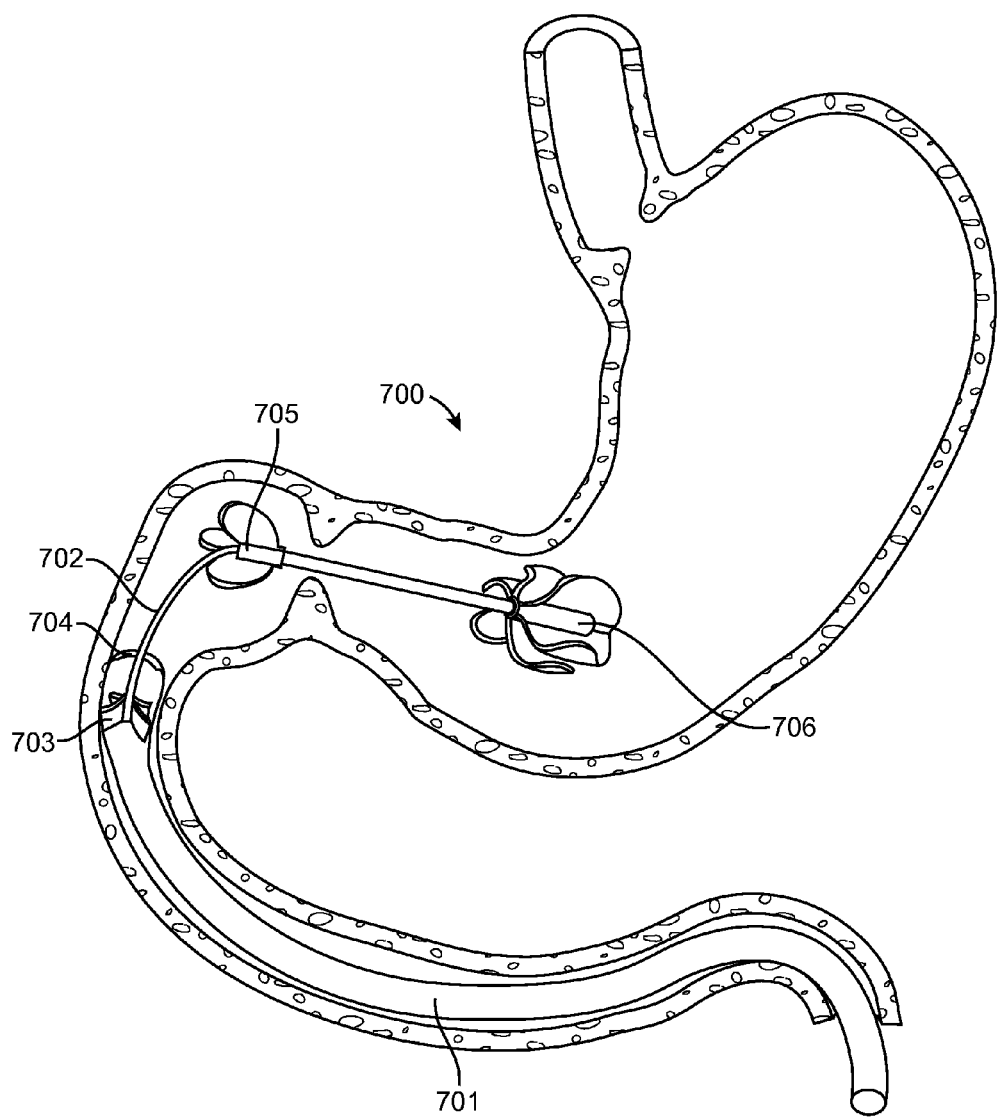
FIG. 7 is a view of a sectioned stomach and small bowel with an intragastric anchor implant with a duodenal sliding seal, in accordance with many embodiments.

FIG. 7 depicts an embodiment of an intragastric anchor implant 700 supporting an intestinal bypass sleeve 701 with a flexible connector 702 such that the opening of the sleeve 701 remains slidably coupled in relatively constant position within the duodenum distal to the duodenal bulb. A flexible connector 702 may be constructed of polymeric elastomer, a fiber reinforced elastomer, a polymer monofilament, or any suitable material or combination of materials. The flexible connector 702 may be configured with sufficient rigidity to transmit compressive mechanical loads as well as tensile loads or it may be configured such that it transmits only tensile loads. A connector 702 may be coupled to a bypass sleeve with a compliant coupling structure 703 allowing temporary compression to a smaller diameter for deliverability and a substantially open lumen such that nutrients and food particles may pass relatively unimpeded. The connector coupling structure 703 may include an elastomeric polymer fin structure, a superelastic nickel-titanium wire structure, or employ any suitably flexible material. The coupling structure 703 may support a sliding seal configured to slideably couple the proximal opening of intestinal bypass sleeve 701 to an anatomical lumen. The distal atraumatic feature 705 covers the rigid element's distal end providing relatively large, compliant surfaces within the duodenum while retaining a relatively open structure such that nutrients and food particles may pass through to the sleeve opening relatively unimpeded. A proximal atraumatic feature 706 may be configured with folded-over fins to present a larger compliant surface area to the surrounding tissues. The atraumatic features or caps, 705 and 706, may be made of any suitable elastomeric material or may include a combination of materials such as silicone and superelastic nickel-titanium, silicone and stainless steel, silicone and polymer monofilaments such as polypropylene, or any suitable compliant material or combination of materials. Alternate embodiments may include at least one fluid-pressurized balloon or non-pressurized bulb as one or both of the atraumatic features.

FIG. 8 depicts an embodiment of an intragastric anchor implant 800 supporting an intestinal bypass sleeve 801 (shown in cutaway view) that is slidably coupled with the duodenum and duodenal bulb via sliding seal 803. In this embodiment, the anchor is coupled to the bypass sleeve 801 via slender loops 804, such as wire loops, which serve as an atraumatic feature to distribute and transfer mechanical loads from the anchor to the bypass sleeve and duodenum while presenting a very small cross-sectional area and little resistance to the passage of nutrients and food particles. The slender loops 804 may also be configured to interfere with the surrounding bypass sleeve 801 such that they provide radial compliance to the sliding seal 803 to aid in maintaining apposition of the proximal sleeve opening to the duodenal wall. Alternately the slender loops may be configured to connect only to a portion of the bypass sleeve 801 such as the proximal opening or a portion distal to the opening, allowing the unconnected portions of the loop structure free to move within the bypass sleeve 801. In a preferred embodiment, the slender loops 804 are made of superelastic nickel-titanium alloy whereas alternate embodiments may employ stainless steel alloys, polymer monofilaments, thermopolymer such as polypropylene, fluoropolymer, thermoplastic elastomer such as Santoprene, or any suitable material.

Figure 9A:
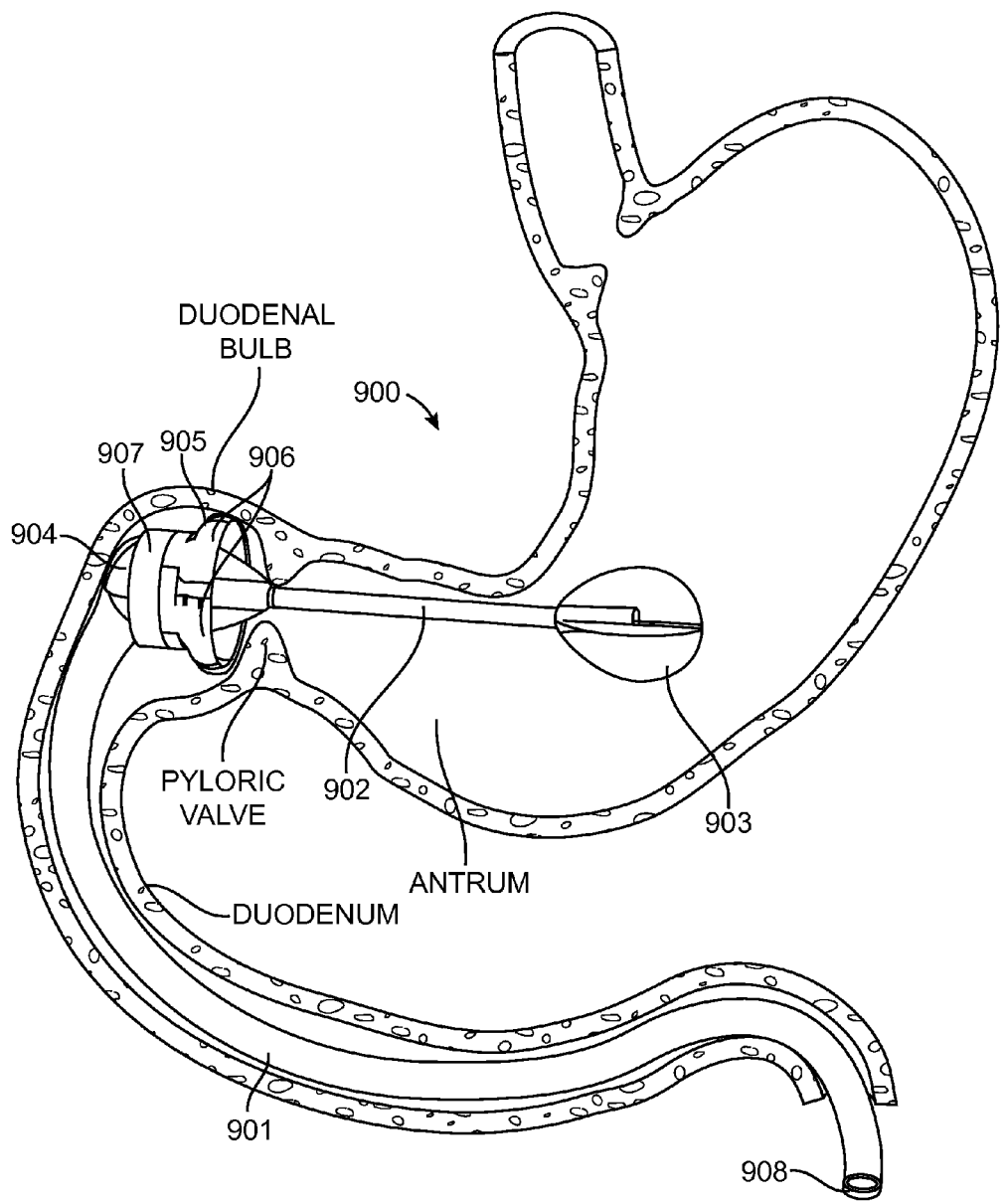
FIG. 9A is a view of a sectioned stomach and small bowel with an intragastric anchor implant with a sliding seal including leaflets, in accordance with many embodiments.
Figure 9B:
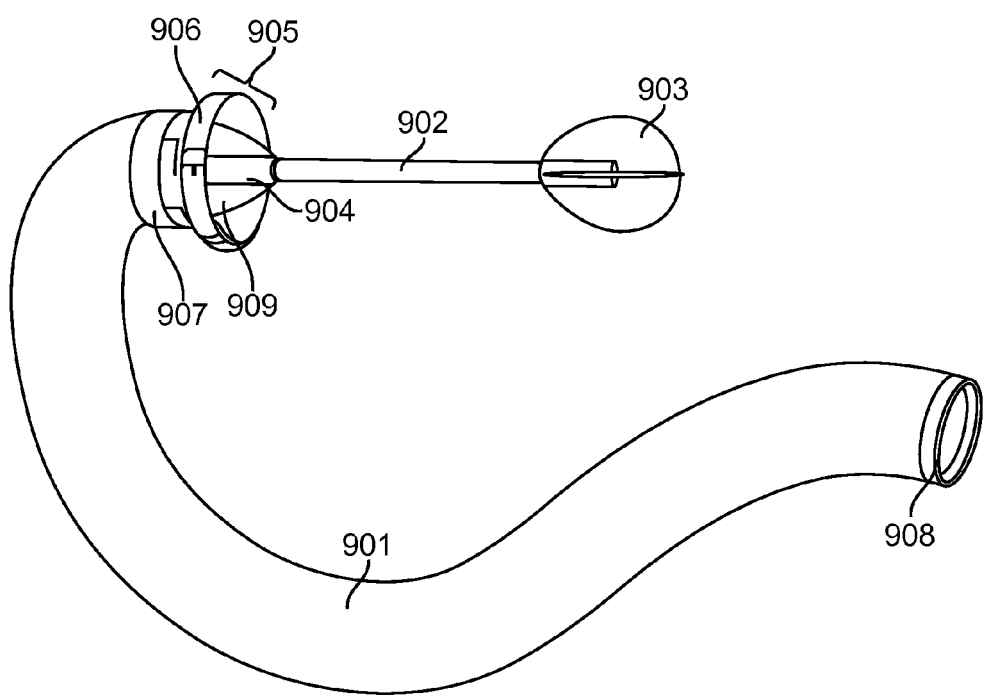
FIG. 9B is a view of an intragastric anchor implant with a sliding seal including leaflets, in accordance with many embodiments.

FIGS. 9A and 9B depict an embodiment of an intragastric anchor implant 900 supporting an intestinal bypass sleeve 901. The implant includes a rigid element 902 configured to pass from the antrum section of the stomach through the pyloric valve and into the duodenal bulb. Proximal and distal atraumatic features, 903 and 904 respectively, serve to spread and transfer mechanical loads preventing tissue erosion and reducing the likelihood of perforation. A sliding seal 905 which slideably couples the proximal opening of the intestinal bypass sleeve 901 to the intestinal lumen may include a plurality of overlapping leaflets 906 configured to conform the sliding seal's diameter to the intestinal lumen's diameter. The leaflets 906 and atraumatic features may be made of a flexible thermoplastic elastomer such as Santoprene, silicone, thermoplastic polymer such as polypropylene, fluoropolymer, or any suitable material. Alternately, they may include multiple materials such as polypropylene and Santoprene, fluoropolymer and nickel-titanium alloy, or any suitable combination of materials that results in appropriate compliance and conformability. The distal atraumatic feature 904 may include a coupling ring 907 configured to aid coupling of the intestinal bypass sleeve 901 to the anchor implant assembly via thermal bonding such as heatstaking, insert molding, or other suitable connection means. The coupling ring 907 may be coupled to the distal atraumatic feature 904 via fins 909 (as shown in FIG. 9B), loops, struts, or other suitable connection elements. A preferred embodiment of the intragastric anchor implant includes an intestinal bypass sleeve 901 made of polypropylene film and a distal feature 904 made of melt-bonding compatible material such as polypropylene polymer or Santoprene thermoplastic polymer. Some embodiments of the intestinal bypass sleeve 901 may include near the distal opening a stiffening element 908 configured to engage intestinal peristalsis to apply distal axial tension to the bypass sleeve 901 and aid in deployment and extension of the bypass sleeve 901 into the intestine. In alternate embodiments, stiffening element 908 may be configured to also prop open a portion of the sleeve 901 and locally maximize its cross-sectional area. The stiffening element 908 may be heatstaked to the sleeve 901, insert molded with the sleeve, bonded with adhesive or may employ any suitable attachment technique.

Figure 10A:
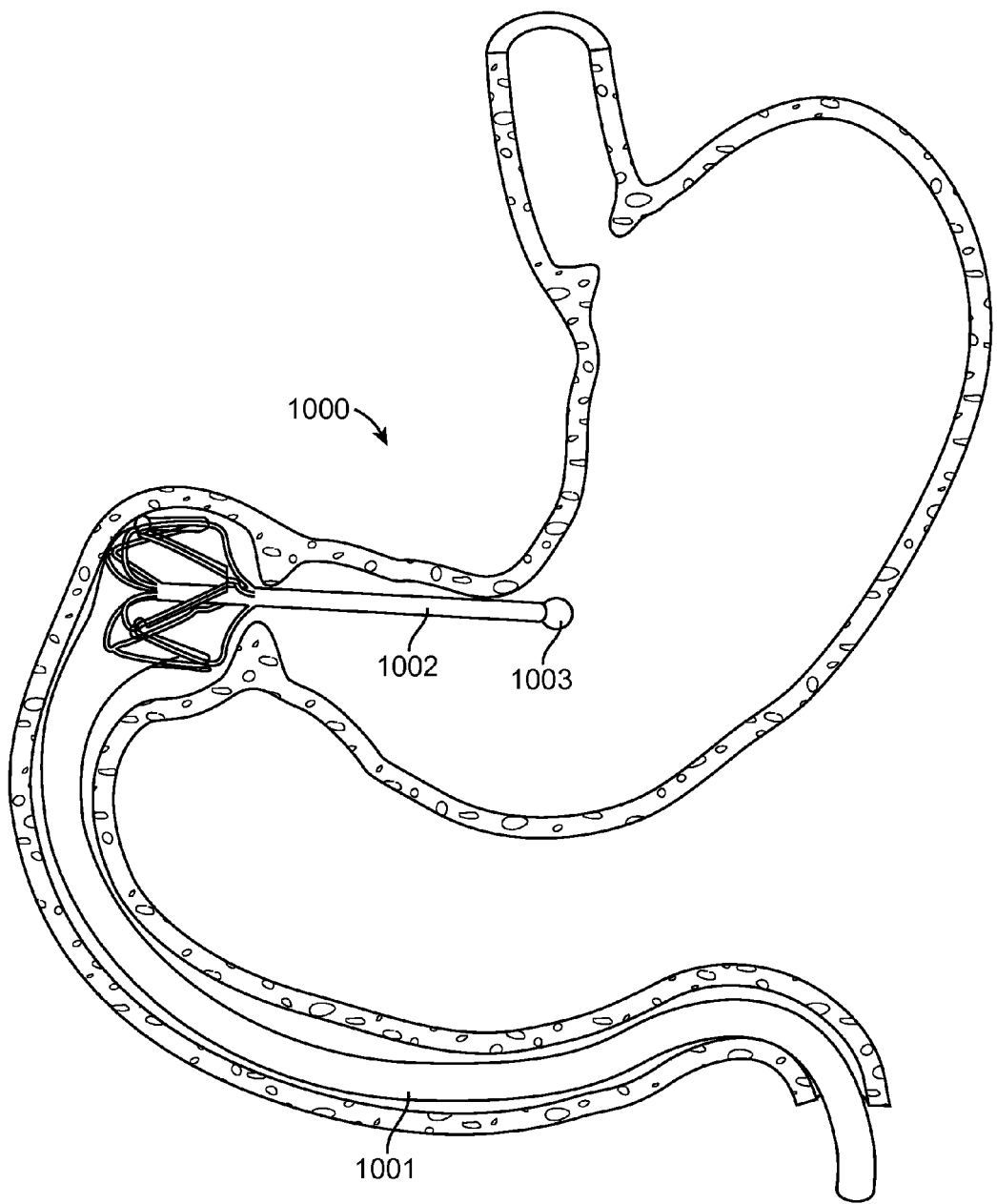
FIG. 10A is a view of a sectioned stomach and small bowel with a one-piece intragastric anchor implant, in accordance with many embodiments.
Figure 10B:
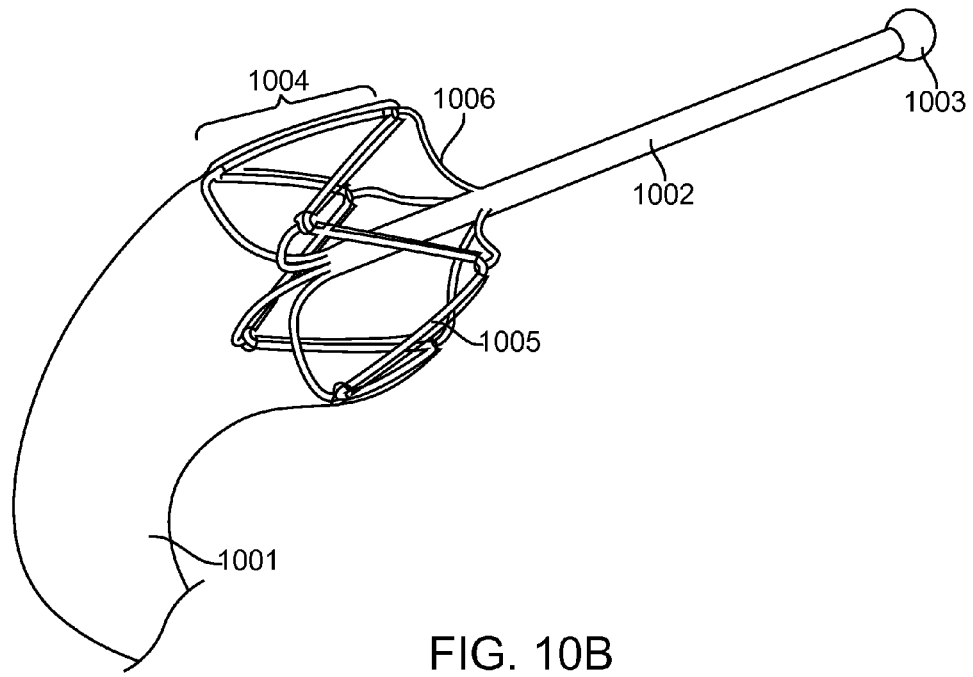
FIG. 10B is a view of a one-piece intragastric anchor implant, in accordance with many embodiments.
Figure 10C:
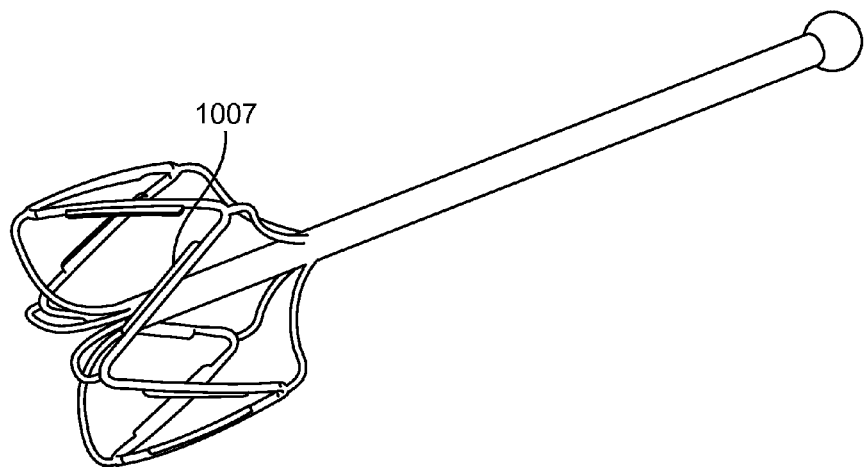
FIG. 10C is a view of a one-piece intragastric anchor implant with attachment tabs, in accordance with many embodiments.

FIGS. 10A, 10B, and 10C depict an embodiment of an intragastric anchor implant 1000 with a sliding seal 1004 configured to directly support the proximal opening of an intestinal bypass sleeve 1001. The sliding seal 1004 in this embodiment may include an expandable sleeve support 1005 configured to expand radially from a collapsed configuration to an expanded configuration, the support slidably coupling the proximal sleeve opening against an anatomical lumen wall when in the expanded configuration. The expanded sleeve support 1005 creates a substantially continuous circumferential seal that causes most nutrients and food particles exiting the stomach to proceed down the lumen of the intestinal bypass sleeve. The expandable sleeve support 1005 may include a sinusoid, diamond, multi-link, or any suitable expandable ring configuration. The expandable sleeve support may be coupled to a rigid element 1002 via struts 1006, fins, or other suitable connecting structures. In a preferred embodiment, flexible struts 1006 connect the rod to at least one apex of an expandable sleeve support sinusoid ring such that the struts to allow the sinusoid to expand and compress radially while maintaining a connection to the rigid element 1002. In a more preferred embodiment, the struts 1006 retain a distal slope such that an expanded sleeve support distal to a narrowed section of lumen such as a sphincter may be radially compressed by withdrawing the rigid element 1002 proximally such that the struts press against the narrowed lumen and flex radially towards the rigid element, drawing the sleeve support inward. The proximal end of the rigid element 1002 may include an atraumatic proximal feature 1003 with an enlarged radius of curvature configured so as to provide a blunt, atraumatic surface. Although the embodiment shown in FIGS. 10A and 10B depicts an intragastric implant 1000 in which rigid element 1002, proximal 1003 atraumatic feature, struts 1006 and expandable sleeve support 1005 are a single-piece structure made of a single material such as polypropylene or fluoropolymer, alternate embodiments may include multiple components made of different materials such as struts or an expandable sleeve support made of nickel-titanium or stainless steel alloy. Fabricating the anchor implant from a single-piece of material is advantageous as it allows the implant to resist wear, breakage and fatigue from the cyclical movements exerted on the anchor implant by gastric motility over the life of the implant while also reducing its manufacturing cost.

FIG. 10C depicts an embodiment of an intragastric anchor implant whereby the expandable sleeve support includes tabs 1007 to which the proximal opening of intestinal bypass sleeve 1001 may be attached via thermal bonding, riveting, clamping, heatstaking, gluing, or other suitable means of attachment.

Figure 11A:
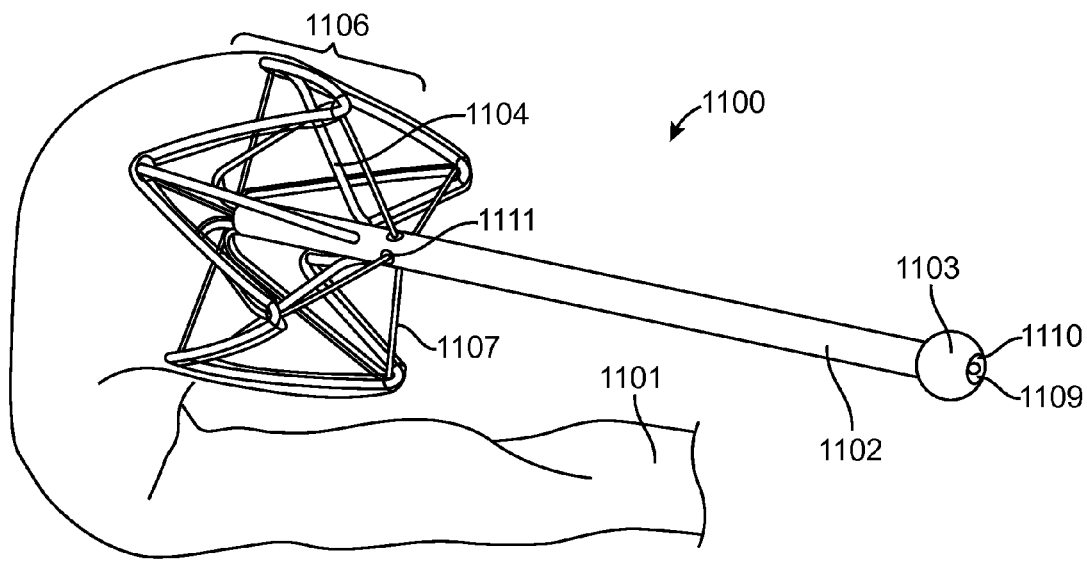
FIG. 11A is a proximal view of an intragastric anchor implant with struts angling in opposite directions, in accordance with many embodiments.
Figure 11B:
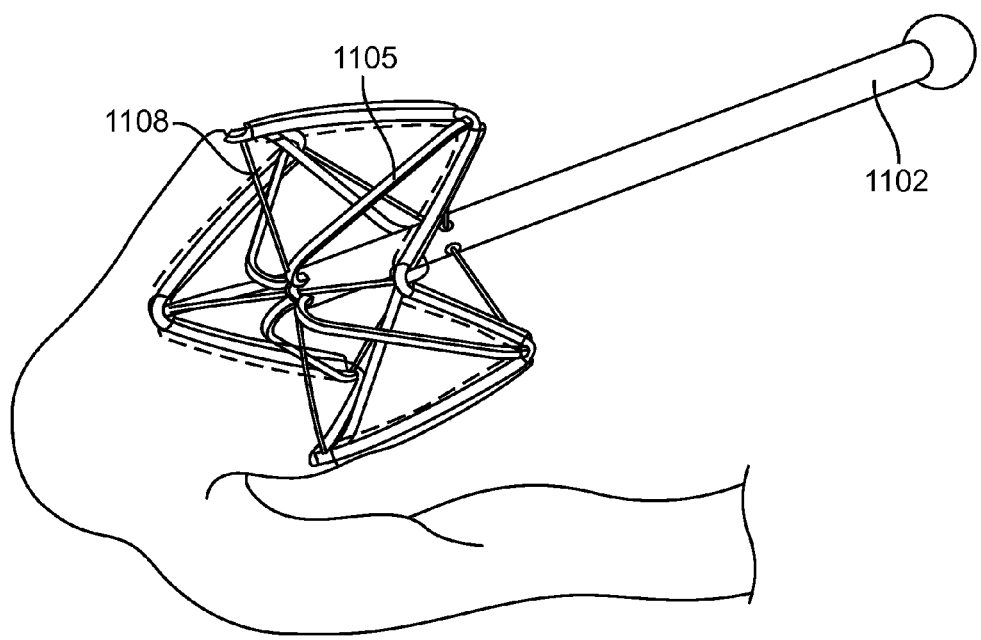
FIG. 11B is a distal view of an intragastric anchor implant with struts angling in opposite directions, in accordance with many embodiments.

FIGS. 11A and 11B depict an alternate embodiment of an expandable sleeve support 1100 includes struts 1104 and 1105 angled in opposite directions connecting the rigid element 1102 to alternating expandable sleeve support 1106 sinusoidal troughs. This configuration allows expansion of the sinusoidal ring without translation relative to the rigid element which is advantageous in that relative to other embodiments it reduces the overall length of the expanding support.

Drawstrings are commonly employed in removable stents as a means of compressing the stent diameter such that it may be withdrawn from an anatomical lumen. As depicted in FIGS. 11A and 11B, an alternate embodiment of an expandable sleeve support includes at least one drawstring, 1107, attached to each proximal sinusoid apex and running through at least one lateral opening 1111 in the rigid element 1102 and through a central lumen 1010. An alternate embodiment may also include a drawstring 1108 attached to each distal sinusoid apex and running through central lumen 1110. Each drawstring may be withdrawn through the central lumen to compress the expandable sleeve support 1106 by pulling on drawstring loop 1109. The drawstring loop may be actuated by pulling into a lumen of a support structure such as the working channel of an endoscope, the tip of which may support the rigid element 1102 providing a counterforce for tension on the drawstring loop which is transmitted to and compresses the expandable sleeve support 1106 reducing its diameter in preparation for removal of the device from an anatomical lumen. The device may be removed by applying a loop snare to the rigid element distal to atraumatic proximal feature 1103.

Figure 12:
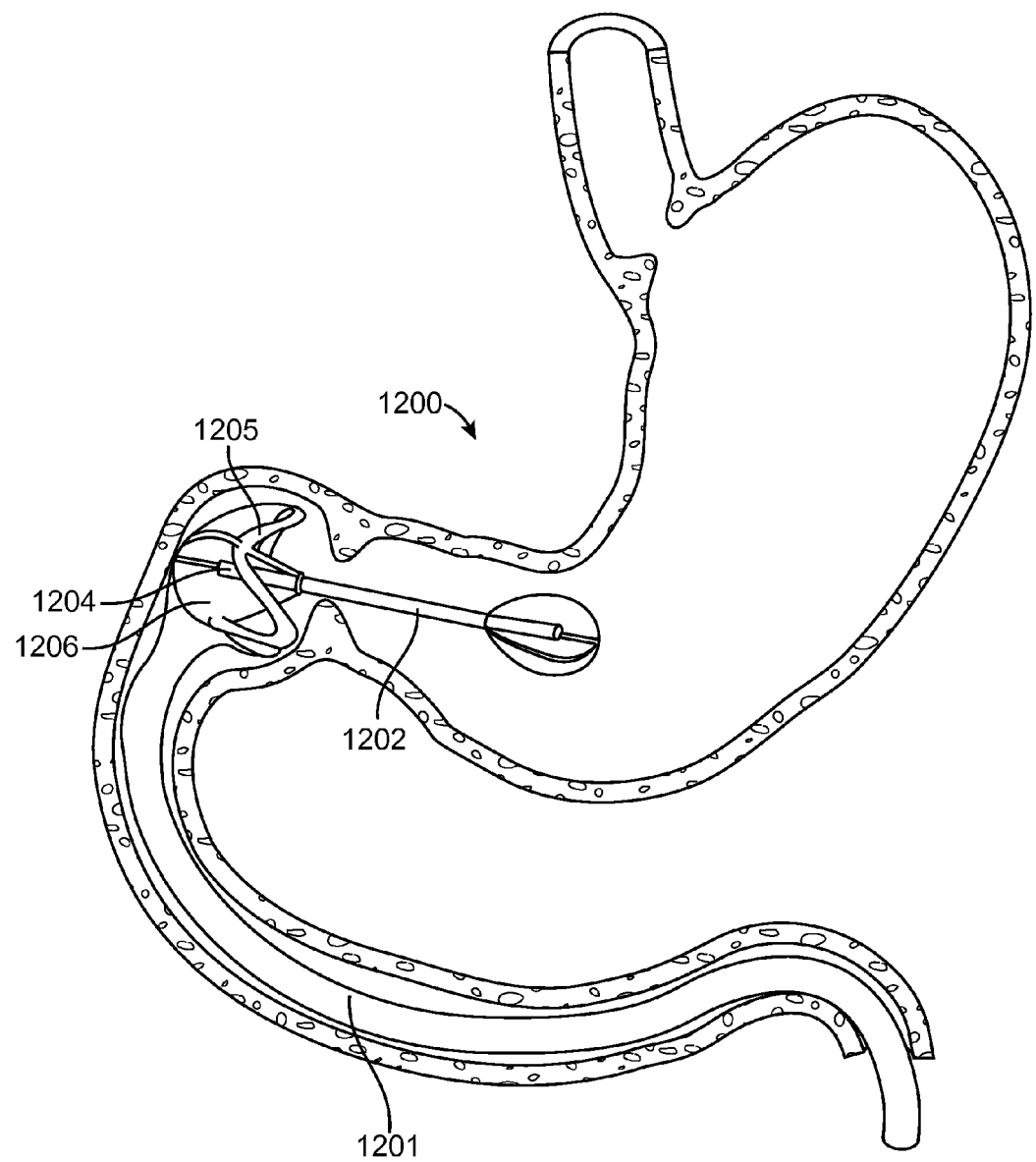
FIG. 12 is a view of a sectioned stomach and small bowel with an intragastric anchor implant with a single-piece atraumatic feature-expandable sleeve support, in accordance with many embodiments.

FIG. 12 depicts an alternate embodiment of an intragastric anchor implant 1200 including an atraumatic distal feature 1204 that includes an expandable sleeve support 1205 to which intestinal bypass sleeve 1201 is attached. In a preferred embodiment, the distal atraumatic feature 1204 and expandable sleeve support are made of flexible polymer as a single piece and the expandable sleeve support 1205 is configured to collapse and compress when the anchor implant is proximally retracted and withdrawn from a luminal narrowing such as the pylorus. The feature and sleeve support may be made of silicone, polypropylene, thermoplastic elastomer such as Santoprene, silicone, fluoropolymer, or any suitable flexible material. In an further preferred embodiment, the distal atraumatic feature 1204 includes radial fins 1206 or struts which are sized to interfere with the lumen into which the feature is placed.

Figure 13:
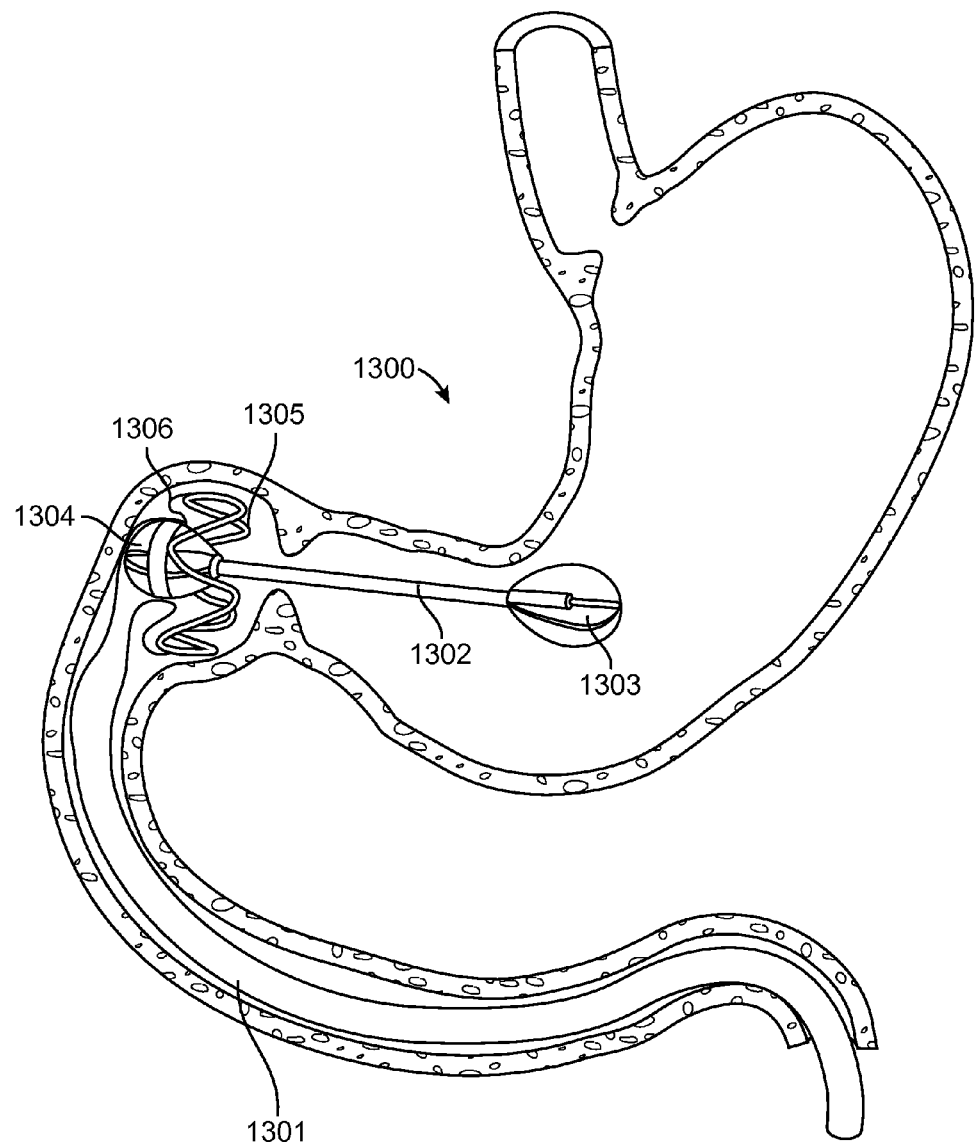
FIG. 13 is a view of a sectioned stomach and small bowel with an intragastric anchor implant with a flexibly-attached sleeve support, in accordance with many embodiments.

FIG. 13 depicts an alternate embodiment of an intragastric anchor implant 1300 in which an expandable sleeve support 1305 is flexibly attached to distal atraumatic feature 1304 via a flexible coupling section 1306. The expandable sleeve support 1305 slidably couples with an anatomical lumen such as the intestine to form a sliding seal and, with the flexible coupling section, guides food particles into intestinal bypass sleeve 1301 while allowing rigid element 1302 with attached proximal and distal atraumatic features, 1303 and 1304 respectively, to move relatively freely with respect to the expandable sleeve support 1305 in response to gastric and intestinal motility. Expandable sleeve support 1305 may be made of nickel-titanium alloy, stainless steel, polymer such as polypropylene or fluoropolymer, or any suitable material. Flexible coupling section 1306 may be made of polymer film such as polypropylene or fluoropolymer, or elastomer such as silicone or thermoplastic elastomer such as Santoprene. An embodiment of the intragastric anchor implant, as shown in FIG. 13, may include a drawstring configured to radially compress expandable sleeve support 1305. A preferred drawstring embodiment may be configured similarly to drawstring 1107 in FIG. 11A such that the drawstring is directed through a lumen in the rigid element 1302 such that the expandable sleeve support 1305 may be radially compressed by pulling the drawstring from a point on the anchor implant proximal to the pylorus. This method of compressing an expandable sleeve support distal to a narrowed section of anatomical lumen such as the pylorus is advantageous in that no additional compression aid need be passed through the pylorus in order to collapse and withdraw the device.

Figure 14A:
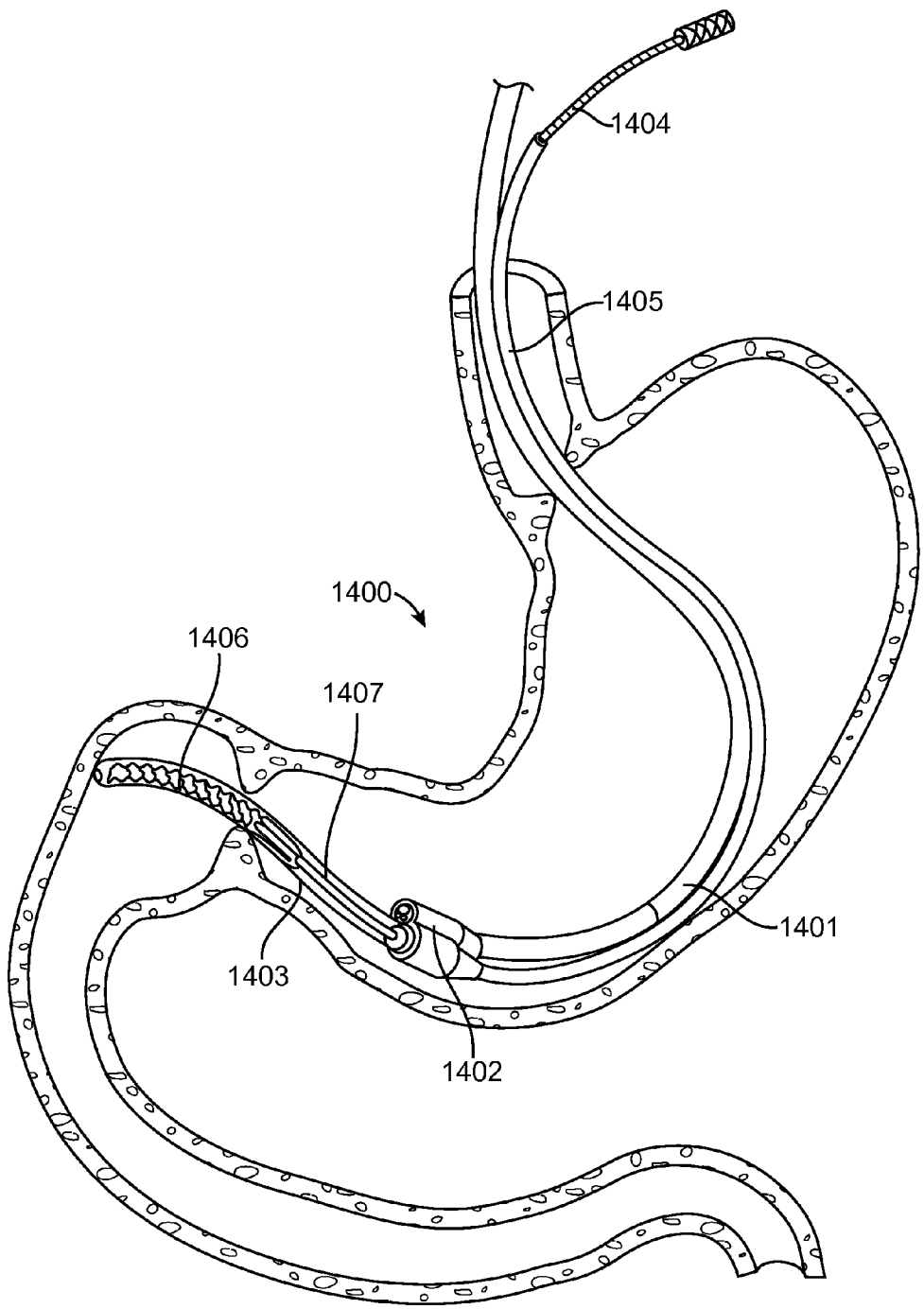
FIG. 14A is a view of a sectioned stomach with a parallel endoscopic delivery system for an intragastric anchor implant, in accordance with many embodiments.

FIG. 14A depicts an embodiment of a parallel endoscopic delivery system 1400 for deployment of an intragastric anchor implant, in accordance with many embodiments. The delivery system 1400 is advanced into the stomach in parallel with an endoscope 1401, which is placed into a long position along the greater curvature of the stomach. Endoscope connector 1402 attaches the delivery system to the distal end of the endoscope via an elastic loop into which the endoscope tip has been inserted. The endoscope connector 1402 may be made of thermoplastic elastomer, silicone, polymer, or any suitable material. A delivery enclosure 1403 contains an intragastric anchor implant 1407 with an attached intestinal bypass sleeve 1406 compressed axially and radially and contained within the delivery enclosure 1403. The delivery enclosure 1403 is located distally to endoscope connector 1402 such that it may be visualized through the endoscope as the entire assembly is advanced and the delivery enclosure 1403 is placed through the pylorus. In a preferred embodiment, the delivery enclosure includes an optically transparent or translucent wall such that the implant itself is visible to the endoscopist as it is advanced and deployed. Parallel placement of the endoscope and delivery enclosure 1403 allows continuous visual monitoring of the intragastric anchor implant is as it is delivered and deployed. A flexible pushrod 1404 runs through a housing 1405 and is used to transmit axial force to push the intragastric anchor implant 1400 out of delivery enclosure 1403, deploying it into the duodenum and stomach.

Figure 14B:
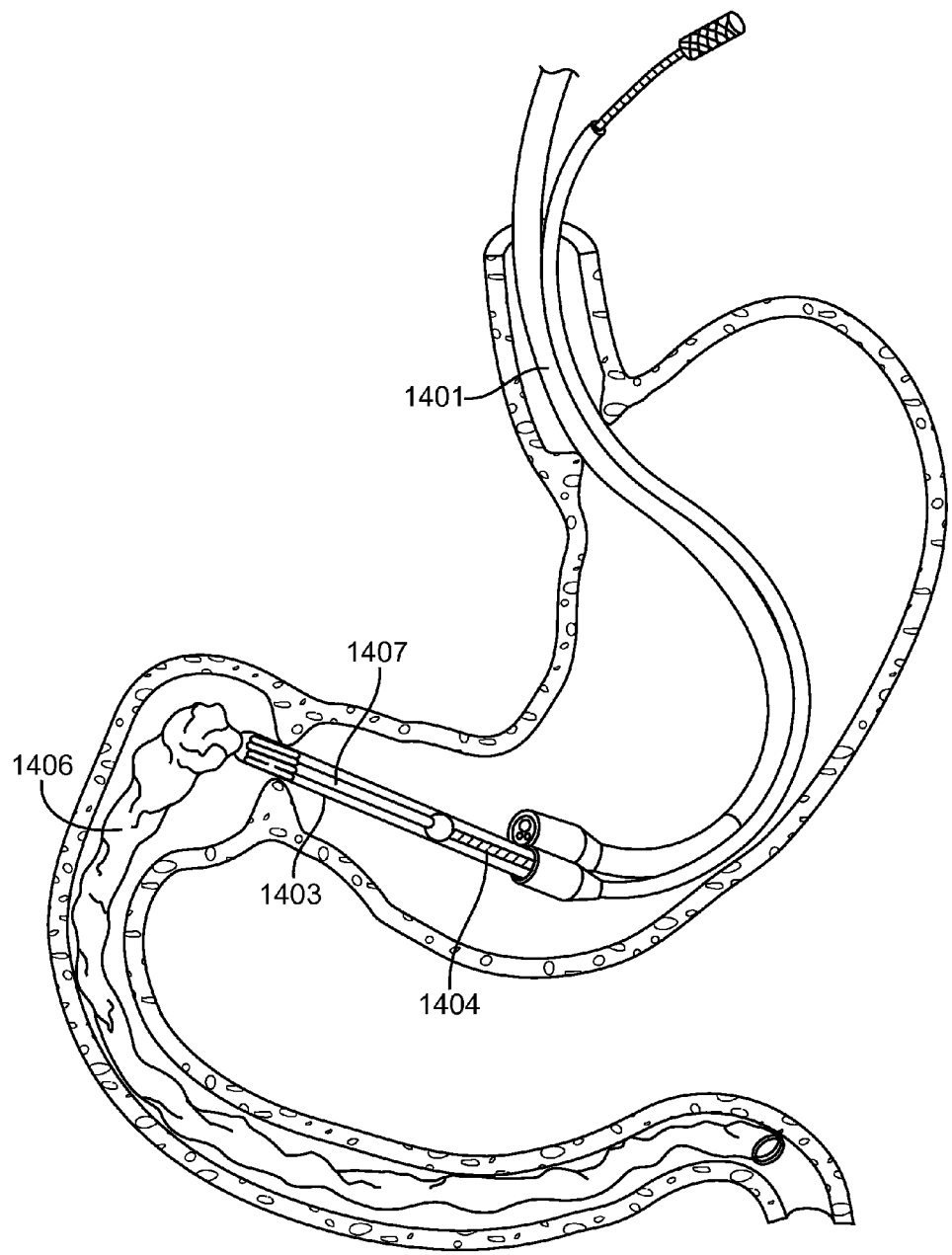
FIG. 14B is a view of a sectioned stomach with a parallel endoscopic delivery system for an intragastric anchor implant extending a sleeve, in accordance with many embodiments.
Figure 14C:
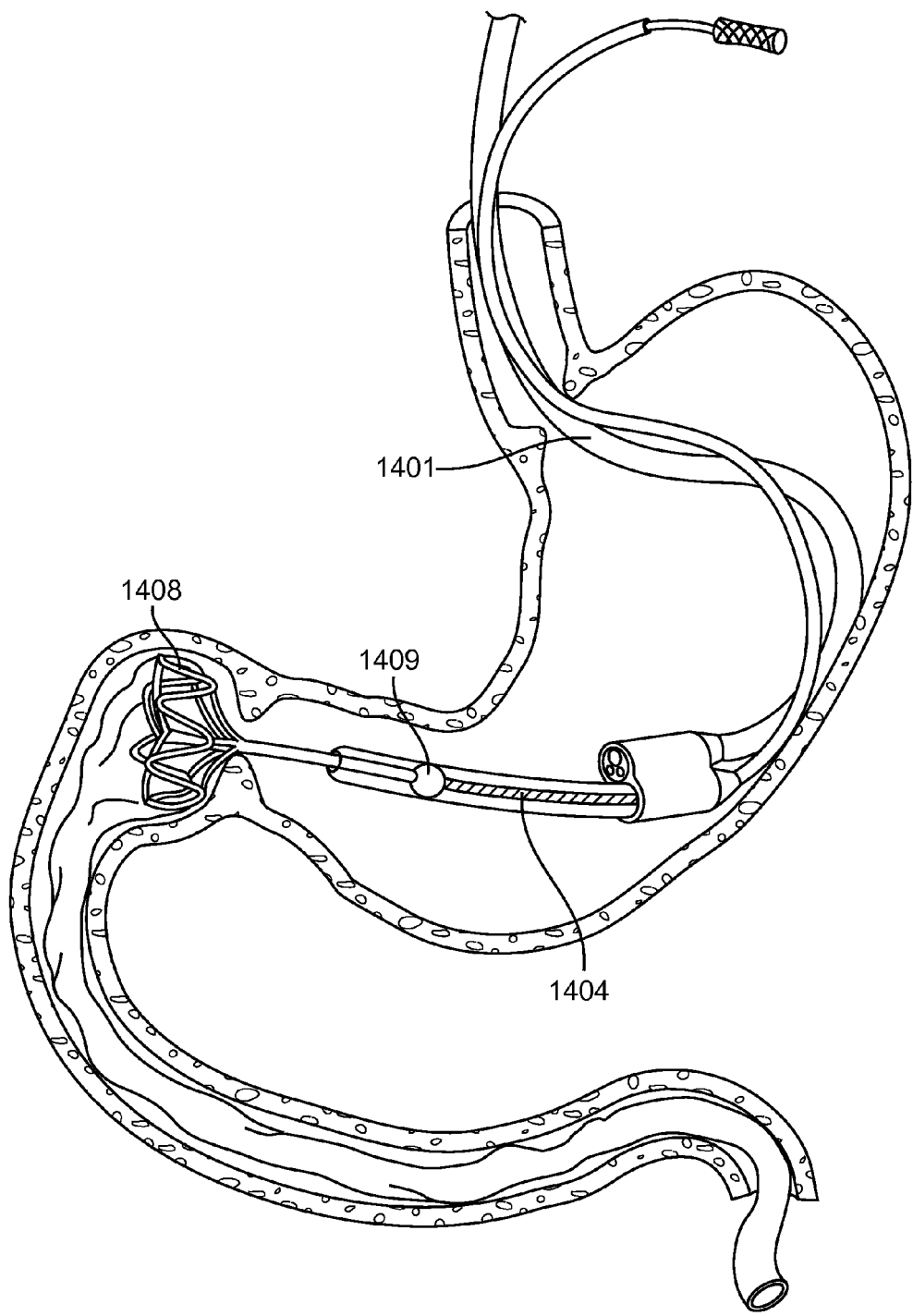
FIG. 14C is a view of a sectioned stomach with a parallel endoscopic delivery system for an intragastric anchor implant deploying an expandable sleeve support, in accordance with many embodiments.

As shown in FIG. 14B, deployment of intragastric anchor implant 1407 through parallel endoscopic delivery system 1400 may proceed with advancement of pushrod 1404 so that bypass sleeve 1406 is advanced out of delivery enclosure 1403. The endoscopist may advance the bypass sleeve 1406 in increments, viewing progress through endoscope 1401, allowing intestinal peristalsis to engage and extend the sleeve 1406 distally within the duodenum and jejunum. Bypass sleeve extension may be confirmed fluoroscopically or radiographically. As shown in FIG. 14C, the anchor implant's distal atraumatic feature 1408 may be advanced out of the delivery enclosure and expanded once the bypass sleeve 1406 has completed its distal extension. The delivery system 1400 and endoscope 1401 may then be withdrawn while pushrod 1404 is advanced further to deploy the anchor implant's proximal atraumatic feature 1409. Full and correct deployment may be confirmed endoscopically before the endoscope 1401 and delivery system are withdrawn from the patient's gastrointestinal tract.

Figure 15A:
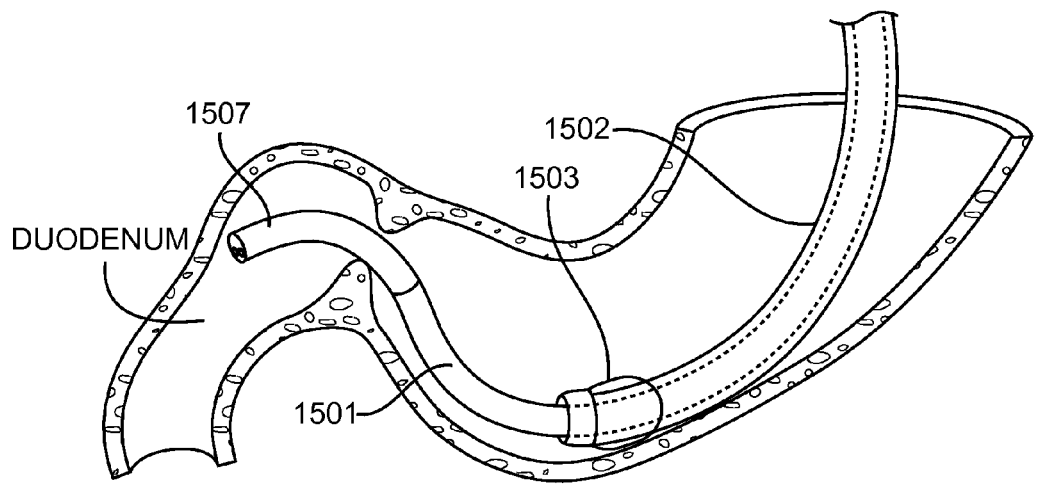
FIG. 15A is a view of a sectioned distal stomach with an endoscope and overtube, in accordance with many embodiments.
Figure 15B:
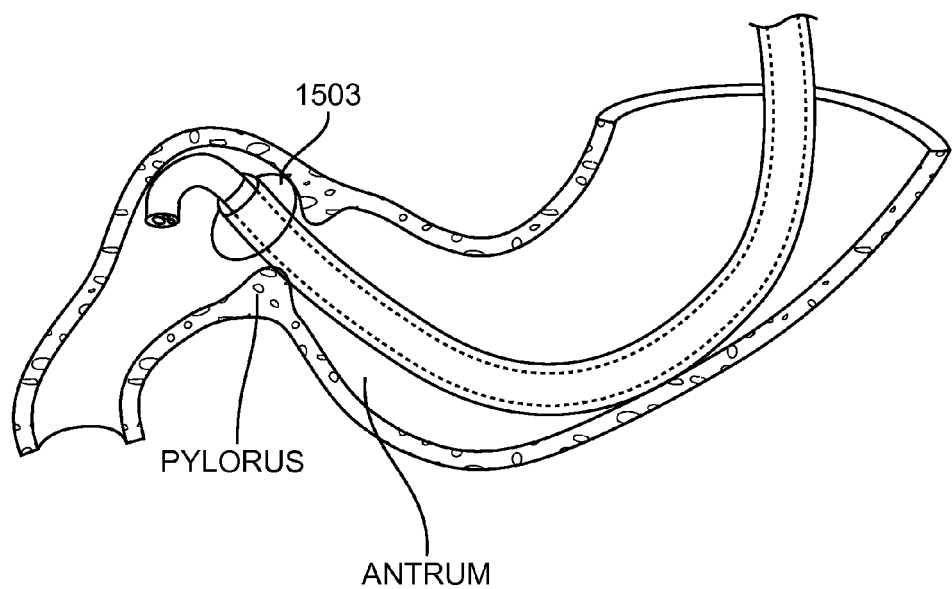
FIG. 15B is a view of a sectioned distal stomach and intestine with an endoscope and overtube with inflated balloon, in accordance with many embodiments.
Figure 15C:
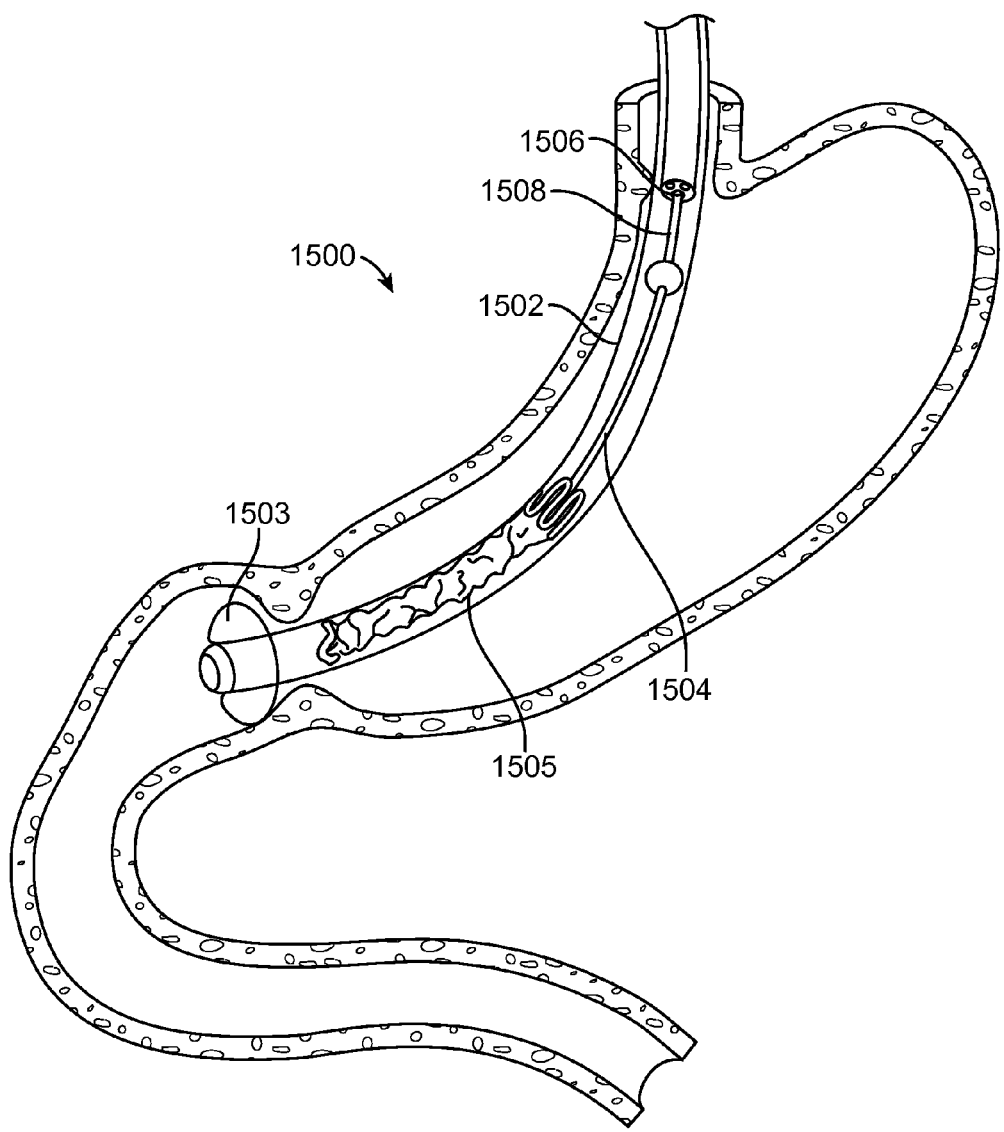
FIG. 15C is a view of a sectioned stomach and intestine with an intragastric anchor implant being delivered distally through an endoscope overtube, in accordance with many embodiments.
Figure 15D:
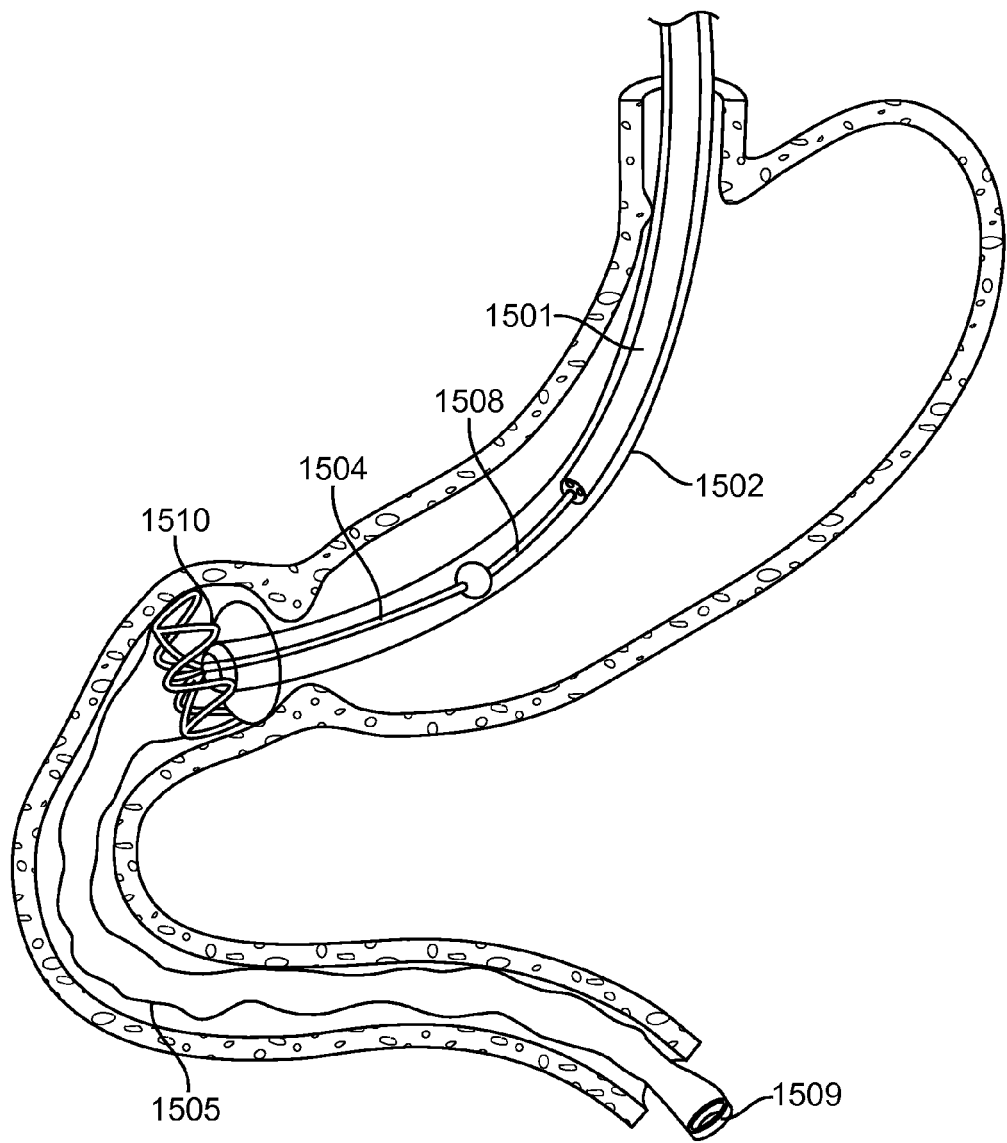
FIG. 15D is a view of a sectioned stomach and intestine with an intragastric anchor implant being delivered distally through an endoscope overtube, in accordance with many embodiments.

FIGS. 15A, 15B, 15C, and 15D depict an embodiment of an alternate, coaxial, delivery system 1500 for an intragastric anchor implant in which an endoscope 1501 with an overtube 1502 including distal balloon 1503 is delivered into the stomach and inserted through the pylorus. As shown in FIG. 15A, the endoscope is initially inserted into the stomach orally and its tip 1507 is guided through the pylorus and into the duodenum while the overtube 1502 remains positioned proximally to the pylorus. The overtube 1502 is then slid distally over the endoscope through the pylorus and distal balloon 1503 is inflated distal to the pylorus as shown in FIG. 15B. The endoscope 1501 is then withdrawn and overtube 1502 is partially withdrawn as shown in FIG. 15C placing the stomach and the overtube 1502 into a relatively straightened position, thus reducing the radius of curvature of the overtube. A straighter overtube 1502 may be advantageous in reducing the force required to advance an intragastric anchor implant through the overtube's central lumen. Intragastric anchor implant 1504 with intestinal bypass sleeve 1505 is introduced into the proximal opening of overtube 1502 and advanced distally in a compressed configuration while the endoscope 1501 is reintroduced and is used to advance the anchor implant. In a specific embodiment of the delivery system, a pushrod 1508 may run through the endoscope's tool channel 1506 and frangibly engage the anchor implant so as to enable the endoscopist to advance the anchor implant while maintaining a relatively steady endoscope position. The pushrod 1508 may also be advantageous in maintaining a physical space between the anchor implant and the tip of the endoscope which may aid in anchor implant deployment by enabling advancement of the implant separate from advancement of the endoscope 1501 as shown in FIG. 15D and by enhancing visibility through the endoscope. FIG. 15D depicts an intragastric anchor implant 1504 partially advanced out of overtube 1502 such that intestinal bypass sleeve 1505 has become uncompressed and has extended distally into the intestine and compressible ring 1510 has expanded into the expanded configuration, no longer constrained by the overtube 1502 in the constrained configuration. In the expanded configuration, compressible ring 1510 is in substantial apposition and sliding contact with the lumen of the duodenum. Fluid such as water or saline may be flushed through the endoscope or overtube to aid in the extension of the bypass sleeve. A radiographic contrast agent such as barium may be included in the fluid to aid in fluoroscopic visualization of sleeve extension. Some embodiments of the intestinal bypass sleeve may include stiffening element 1509 near the distal opening, the stiffening element configured to engage intestinal peristalsis to apply distal axial tension to the bypass sleeve 1505 and aid in deployment and extension of the bypass sleeve into the intestine. In alternate embodiments, stiffening element 1509 may be configured to also prop open a portion of the sleeve 1505 and locally maximize its cross-sectional area. Stiffening element 1509 may be configured for substantial radiopacity such that full sleeve extension may be confirmed fluoroscopically and may include barium, tantalum, gold, metallic particles, or any suitable radio-opaque material in its construction. The stiffening element 1509 may be heat staked to the sleeve, thermally bonded with the sleeve, insert molded with the sleeve, bonded to the sleeve with adhesive or may employ any suitable attachment technique.

Figure 16A:
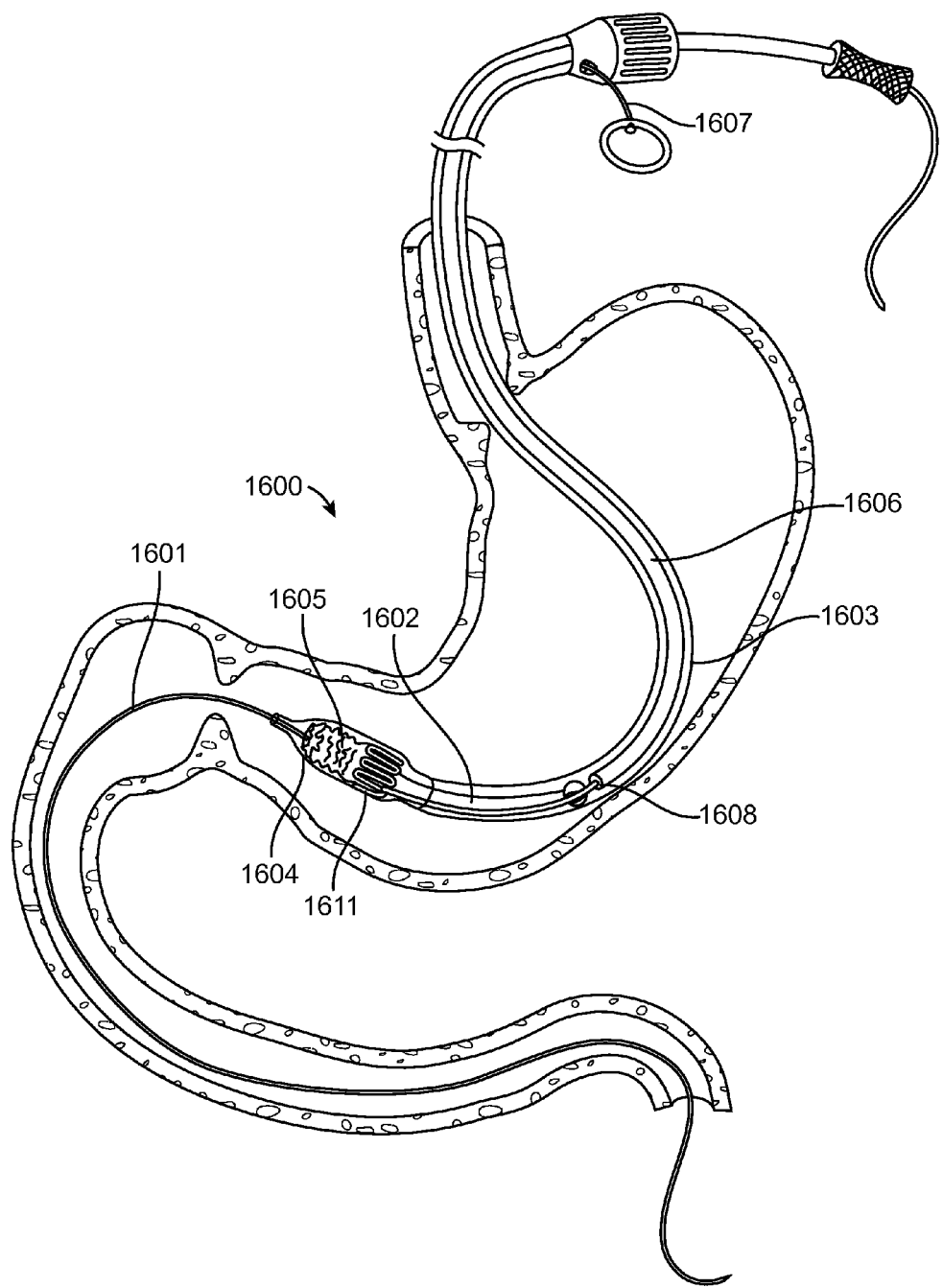
FIG. 16A is a view of a sectioned stomach and intestine with an over the wire intragastric anchor implant delivery system, in accordance with many embodiments.
Figure 16B:
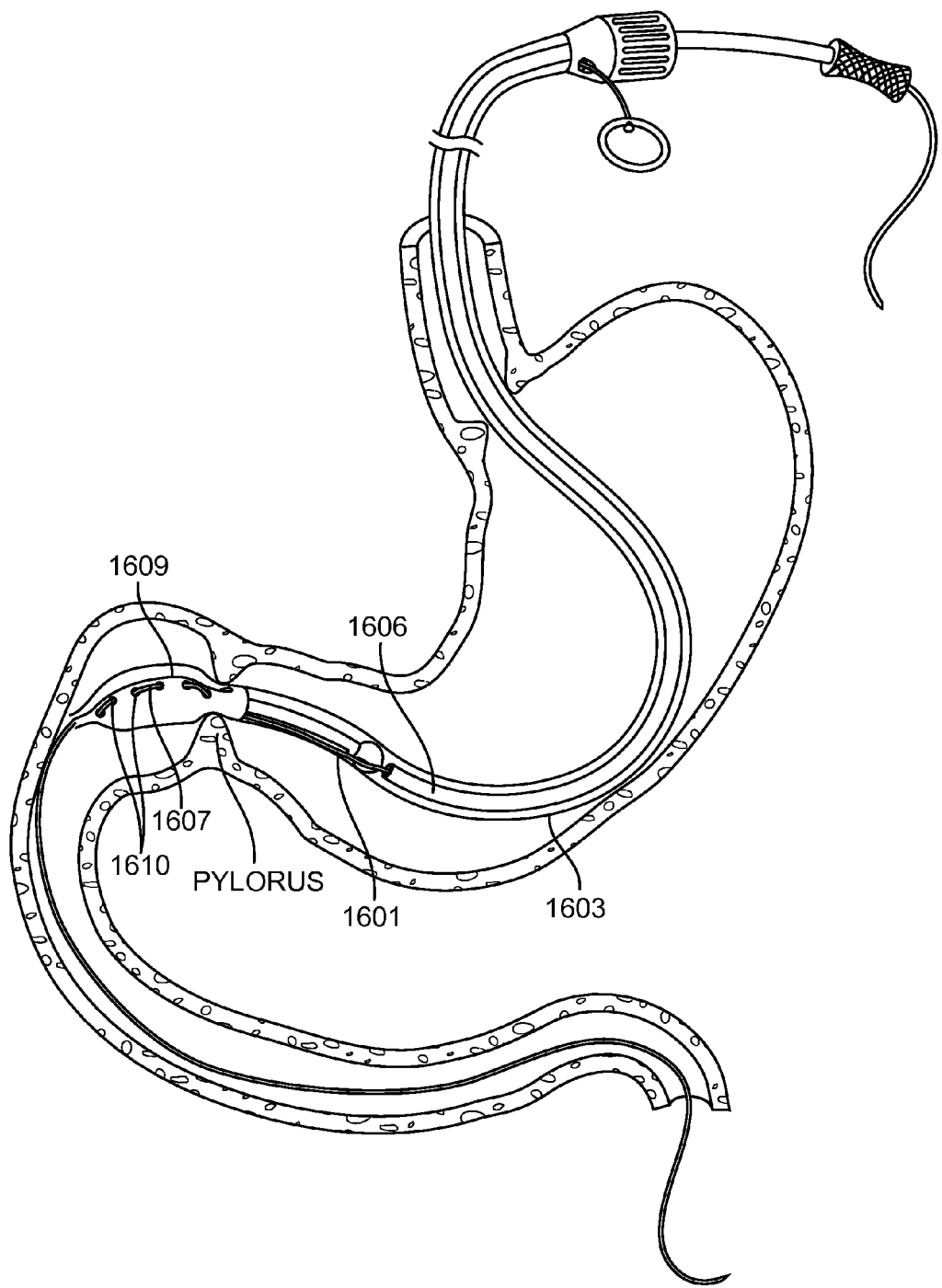
FIG. 16B is a view of a sectioned stomach and intestine with an intragastric anchor implant delivery system with a split introducer, in accordance with many embodiments.

FIGS. 16A, 16B and 16D depict an alternate delivery system 1600 for an intragastric anchor implant 1602 in which a flexible sheath 1603 encloses a compressed anchor implant and intestinal bypass sleeve 1605. An endoscope is initially placed into the duodenum and a guidewire 1601 is advanced distally into the duodenum and jejunum through the endoscope's working channel per standard endoscopic practice. As shown in FIG. 16A the flexible sheath may be delivered over guidewire 1601 and may include an introducer tip 1604 whose distal end tapers to a relatively small diameter, preferably approximately to the diameter of the guidewire, to ease passage through narrowed lumens such as the pylorus. The guidewire may pass through the introducer tip 1604, through the intestinal bypass sleeve 1605 and compressible ring 1611, and through the central lumen of the flexible sheath and through the lumen 1608 of the plunger 1606 such that the entire assembly may be advanced over the guidewire 1601.

As shown in FIG. 16B, the introducer tip 1604 may include at least one split 1609 along a portion of its length such that it may expand radially to allow the anchor implant to exit when advanced distally relative to the introducer tip. The split may be held together with a tether 1607 such as suture, monofilament, wire, or the like, threaded through openings 1610 along adjacent edges of the split such that removal of the tether allows the introducer tip 1604 to open and expand. Alternately, the split may be held together with frangible connections such as perforations, scoring, thermal bonds, adhesive, or any suitable connection means. In some embodiments, the introducer tip may be larger in diameter than the flexible sheath 1603, such that it may help to retain the sheath's position within the gastrointestinal tract when fully advanced past a narrow section of lumen such as the pylorus. When advanced relative to the flexible sheath 1603 plunger 1606 transmits axial force to the anchor implant to advance it distally and deploy it. The plunger may include a lumen 1608 along a portion of its length through which a guidewire 1601 extends.

Figure 16C:
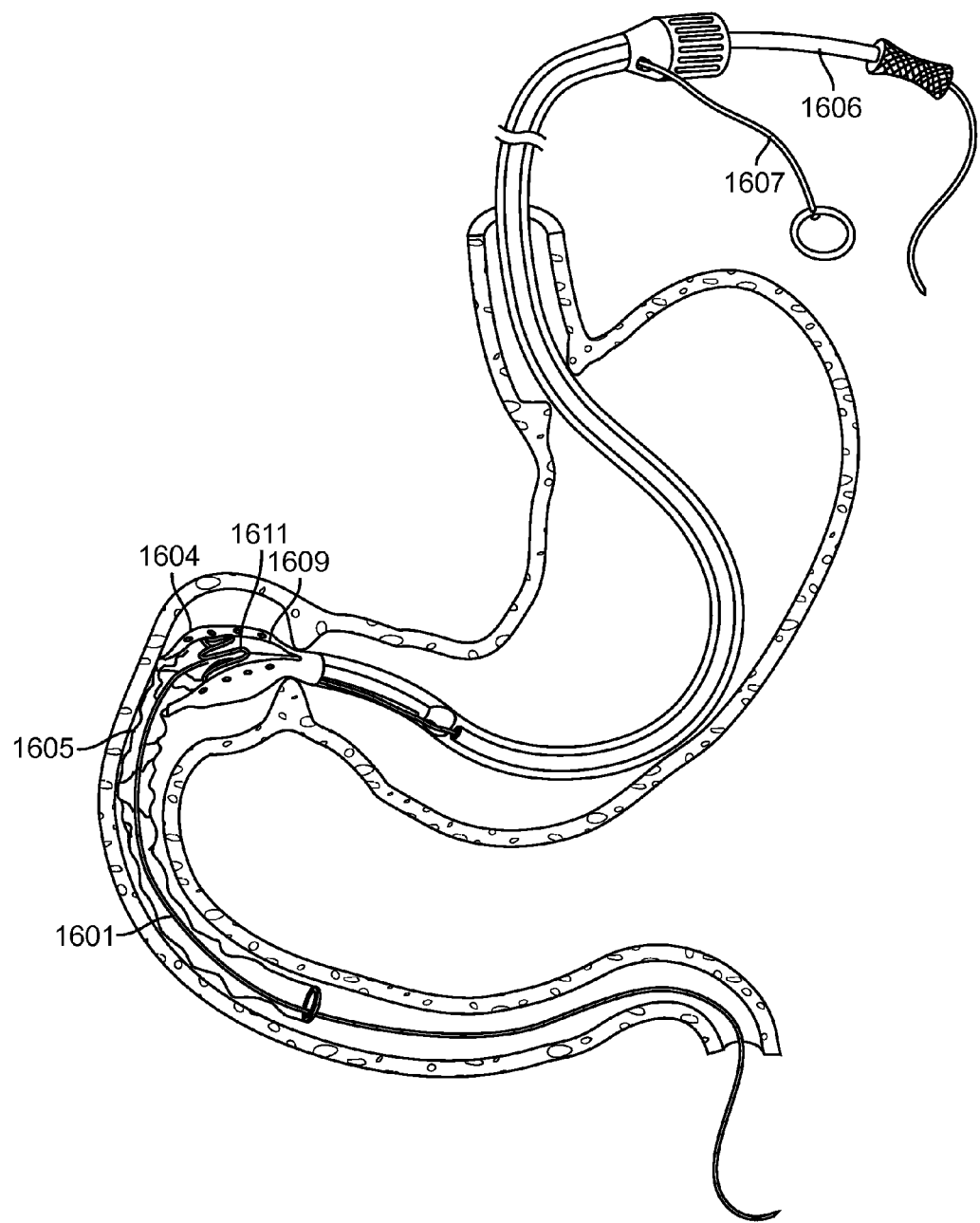
FIG. 16C is a view of a sectioned stomach and intestine with an intragastric anchor implant delivery system with a split introducer releasing a sleeve and expandable sleeve support, in accordance with many embodiments.

As shown in FIG. 16C, split 1609 in introducer tip 1604 is disconnected such that it may expand radially when tether 1607 is withdrawn relative to the flexible sheath 1603, allowing compressible ring 1611 to expand and intestinal bypass sleeve 1605 to expand radially and to longitudinally extend along and over guidewire 1601. The flexible sheath and introducer t may be withdrawn over plunger 1606 to fully release intragastric anchor implant 1600, leaving the guidewire temporarily in place while intestinal peristalsis applies distal axial tension to the bypass sleeve and extends it to its full length. The presence of the guidewire during bypass sleeve deployment may be advantageous in preventing kinking and longitudinal folding.

Figure 17A:
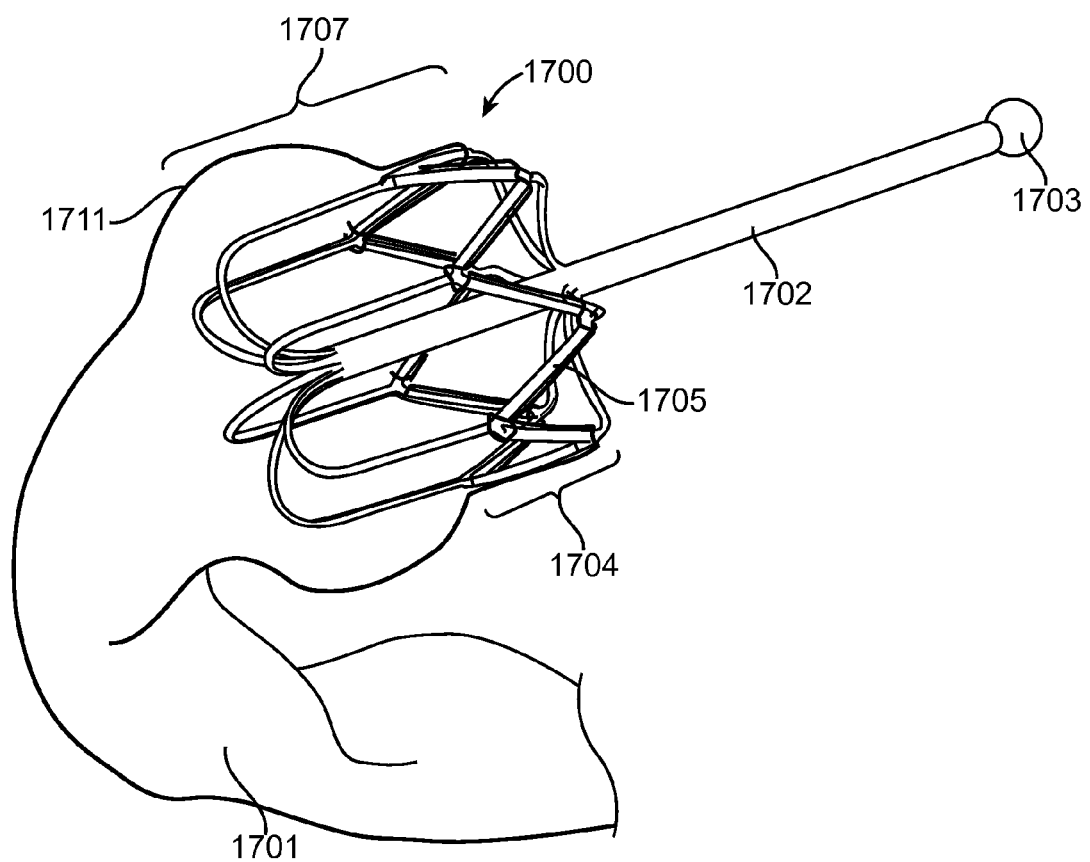
FIG. 17A is a view of a with an intragastric anchor implant having space-filling struts, in accordance with many embodiments.
Figure 17B:
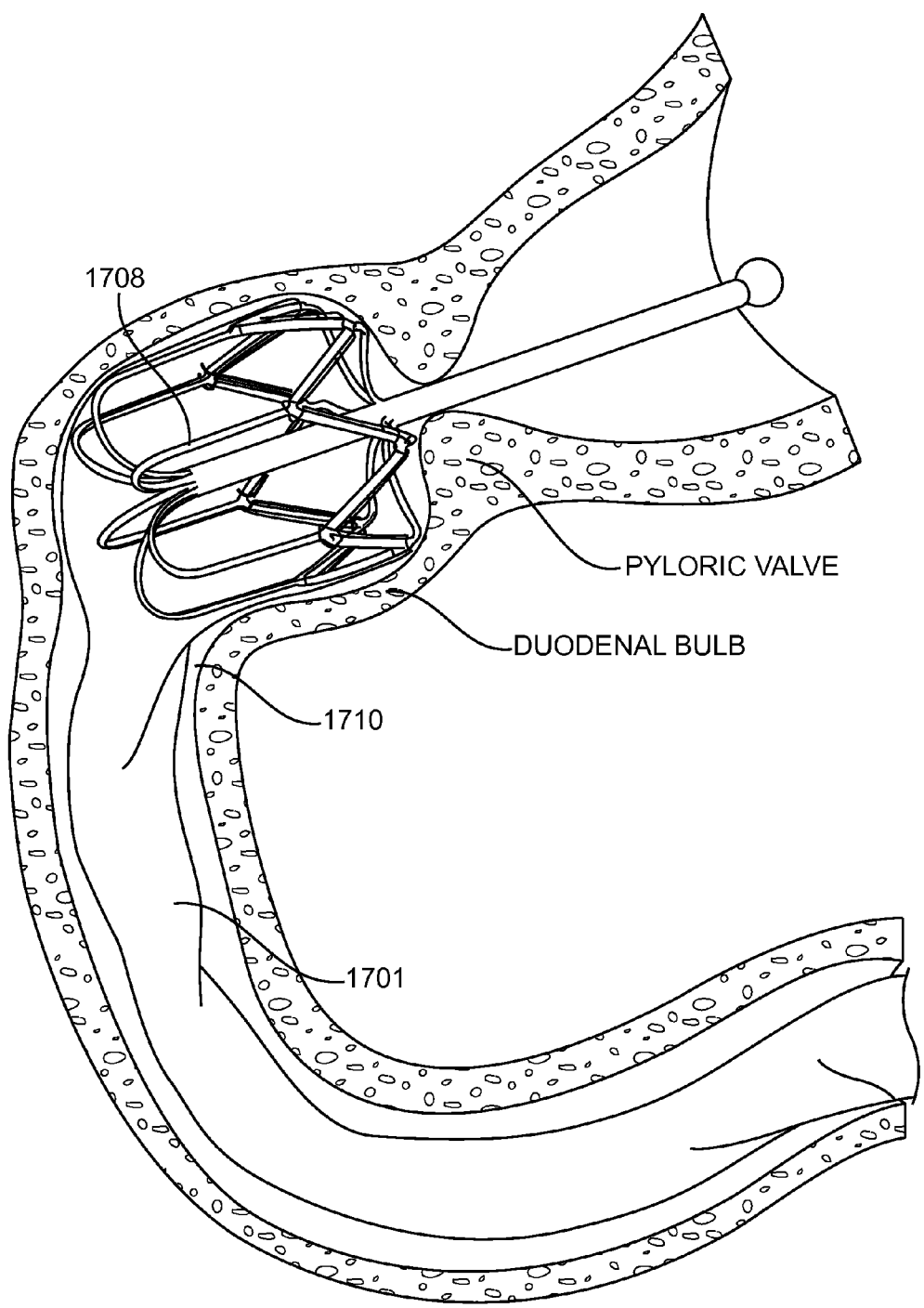
FIG. 17B is a view of a sectioned stomach and intestine with the intragastric anchor implant with space-filling struts, in accordance with many embodiments.

FIGS. 17A and 17B depict a preferred embodiment of an intragastric anchor implant 1700 with a rod 1702 separating a proximal atraumatic tip 1703 and a distal atraumatic tip 1707 which is configured to substantially fill the duodenal bulb. The distal atraumatic tip 1707 may include on a proximal section a sliding seal 1704 configured to directly support the proximal opening of an intestinal bypass sleeve 1701 in close proximity to the pyloric valve. The sliding seal in this embodiment may include an expandable sleeve support 1705 configured to expand radially and slidably couple the proximal sleeve opening against an anatomical lumen wall, creating a substantially continuous circumferential seal that causes most nutrients and food particles exiting the stomach to proceed down the lumen of the intestinal bypass sleeve 1701. The expandable sleeve support 1705 may include a sinusoid, zig-zag, diamond, multi-link, a plurality of flexible arms, or any suitable expandable ring configuration. The distal atraumatic tip 1707 may also include space-filling struts 1708 configured to support sleeve 1701 and maintain a patent path for nutrients and food particles through the sleeve as they negotiate the first turn of the duodenum 1710. Sleeve 1701 may include a section of enlarged diameter 1711 immediately distal to sliding seal 1704. This enlarged section may enable sleeve 1701 to accommodate a tight turn such as the first bend of the duodenum 1710 while maintaining a patent path for chyme through the distal atraumatic tip 1707 without pinching or obstruction.

Figure 18A:
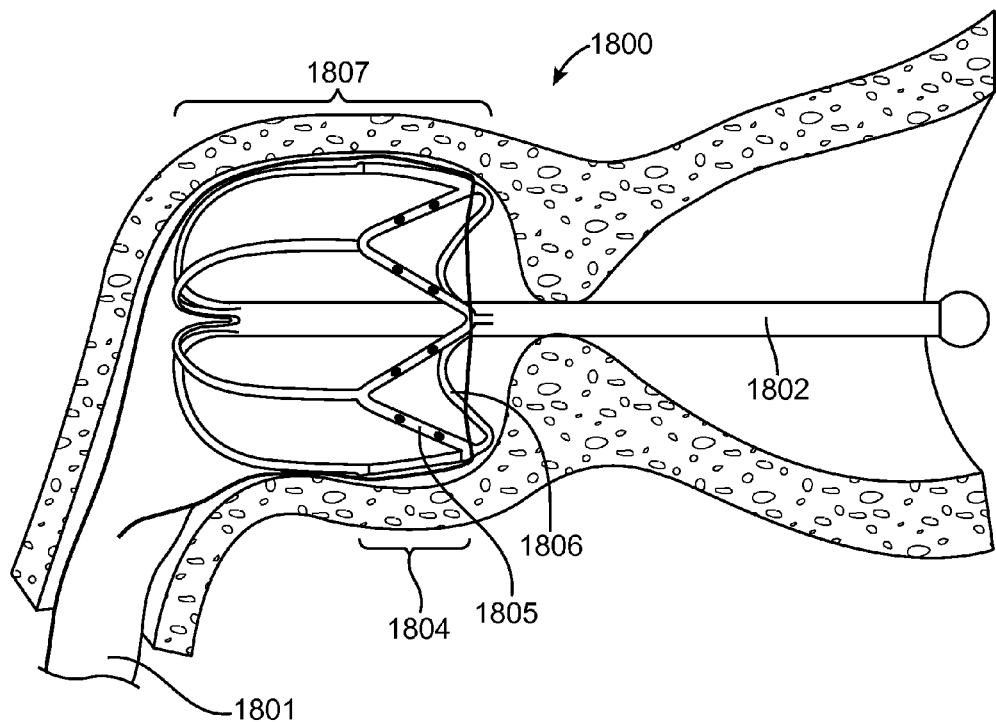
FIG. 18A is a view of a sectioned stomach and intestine with an intragastric anchor implant having a recurve strut configuration, in accordance with many embodiments.
Figure 18B:
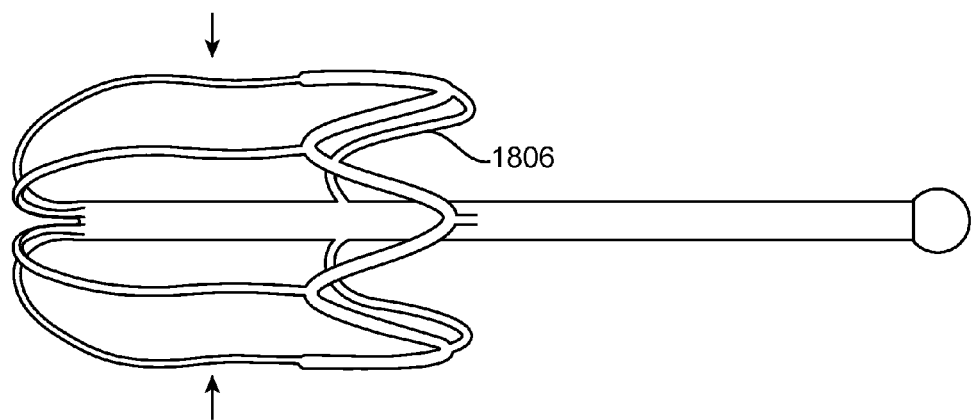
FIG. 18B is a view of the intragastric anchor implant with the recurve strut configuration under compression, in accordance with many embodiments.
Figure 18C:
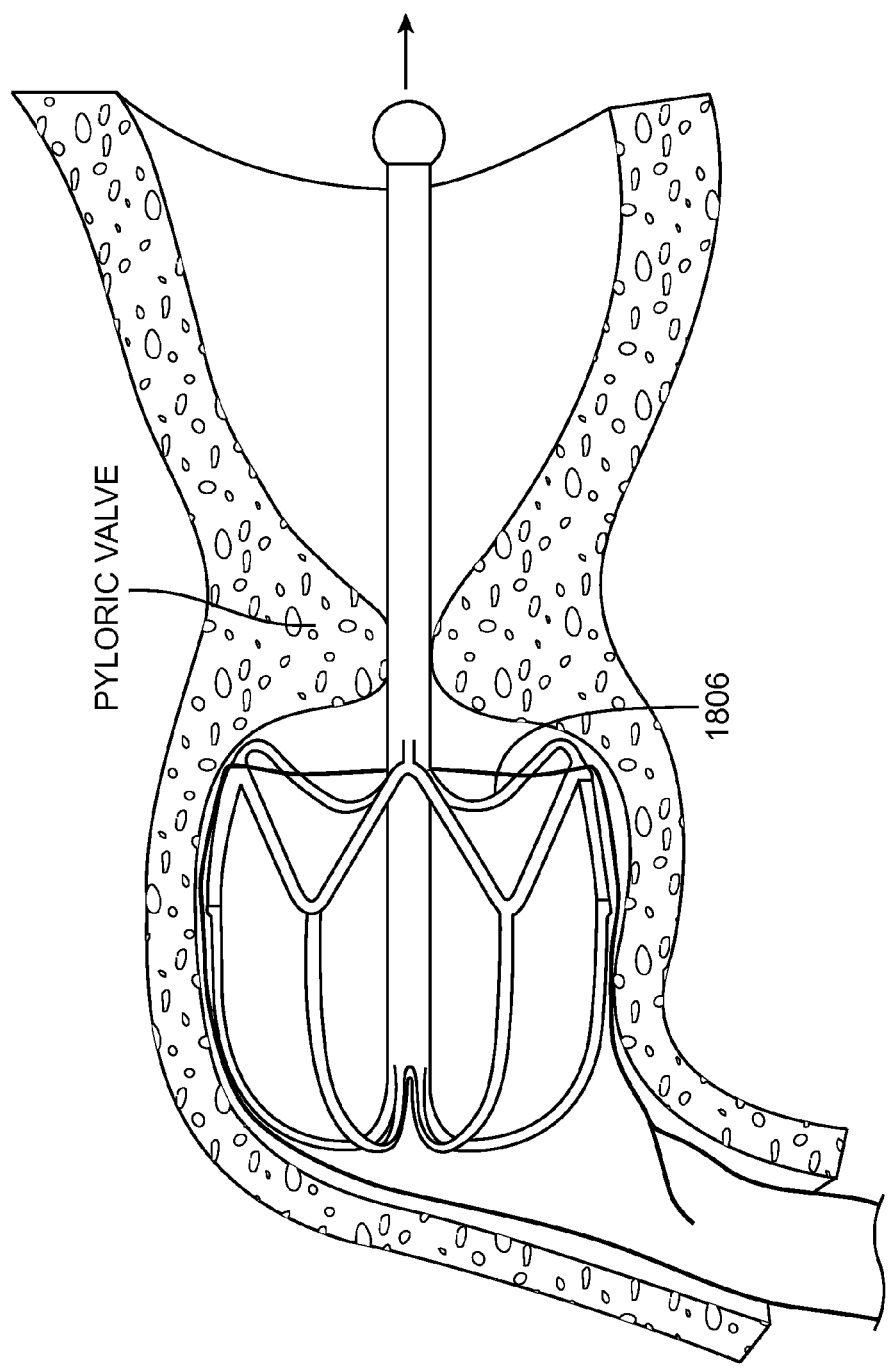
FIG. 18C is a view of a sectioned stomach and intestine with the intragastric anchor showing flexure of the recurve strut configuration, in accordance with many embodiments.

FIGS. 18A, 18B, and 18C depict an embodiment of an intragastric anchor implant 1800 with connecting struts 1806 which angle distally at rod 1802 and curve proximally to reach the edge of expandable sleeve support 1805. As shown in FIG. 18A, this recurve strut configuration enables sliding seal 1804 to be positioned immediately adjacent to the pyloric valve.

As shown in FIG. 18B, distal atraumatic tip 1807 may be compressed radially for delivery by flexing connecting struts 1806 proximally. This compression configuration is advantageous in that it produces an effectively flat surface at the proximal end of the atraumatic tip which may be placed directly against the pyloric valve. Additionally, proximal tension on the rod 1802 will tend to expand the distal atraumatic tip 1807, helping to seat it against the duodenal lumen.

As shown in FIG. 18C, when the anchor implant 1800 is withdrawn the connecting struts 1806 may flex distally as they are pressed against the pyloric valve, presenting a tapered, conical surface in aggregate which will tend to radially compress the distal atraumatic tip 1807 as the struts 1806 pass through the pyloric valve.

Figure 19:
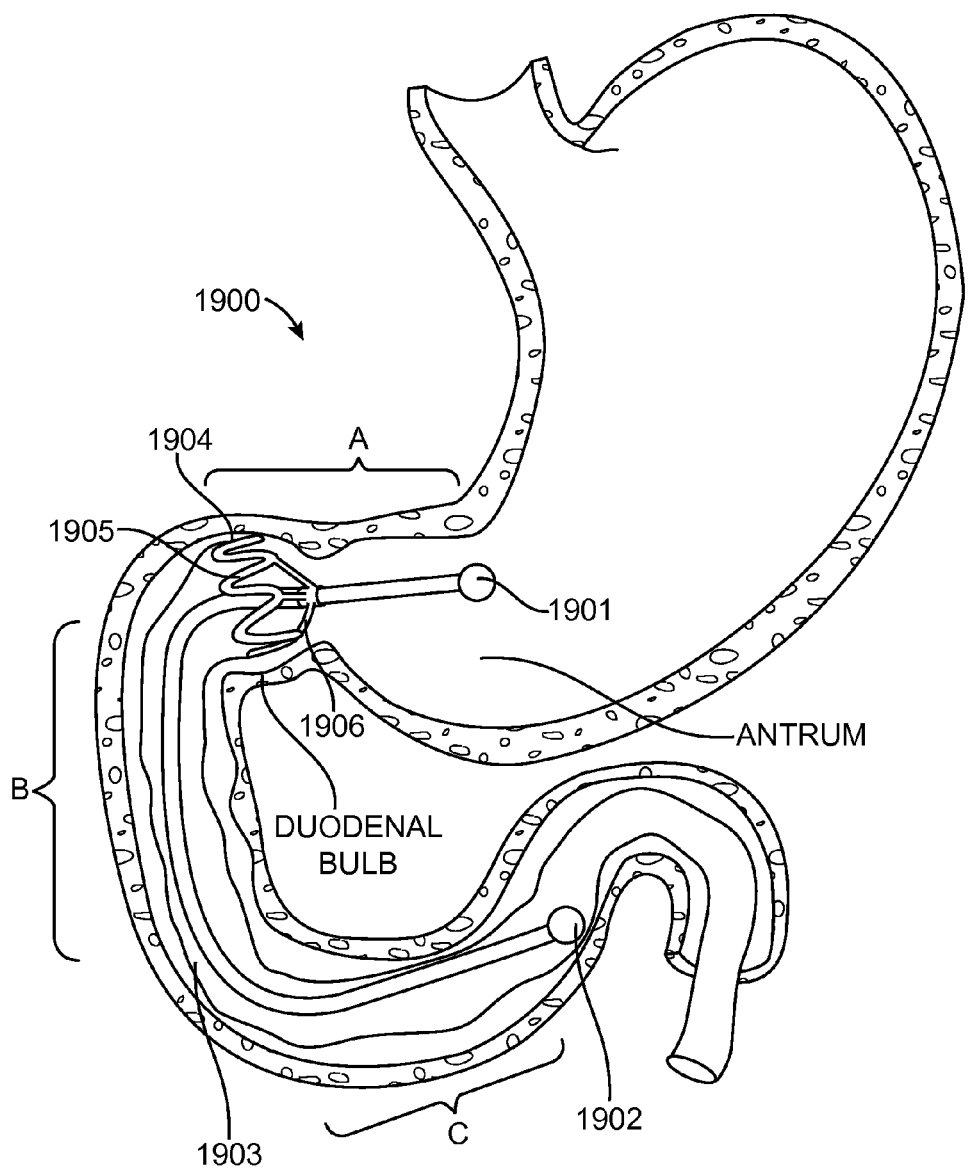
FIG. 19 is a view of a sectioned stomach and intestine with a C-shaped intragastric anchor implant, in accordance with many embodiments.

FIG. 19 depicts a gastroduodenal anchor 1900 with a proximal atraumatic feature 1901 and a distal atraumatic feature 1902 and a sliding seal 1904 disposed therebetween supporting an intestinal bypass sleeve 1903. As shown, the sliding seal 1904 may be configured as a radially expandable structure supporting the proximal end of the intestinal bypass sleeve 1903 to allow atraumatic movement within the gastrointestinal tract. Typically, the sliding seal 1904 is adapted to sit in or near the duodenal bulb. The elongate element extending between the proximal and distal atraumatic features may be either rigid, flexible, or have portions of each; it may be either straight, curved, include one or more bends, or have various other combinations of geometries. For example, as shown in FIG. 19, the elongate element may include two bends or curved portions so as to conform to the shape approximate shape of the gastrointestinal tract and improve anchoring and comfort for the patient. Although the proximal and distal atraumatic features are shown as bulbous features and the sliding seal is shown as an expandable structure, it is appreciated these features may include any of the atraumatic features and sliding seals described herein.

The anchor may be configured in various shapes as desired. For example, as shown FIG. 19, the gastroduodenal anchor 1900 may be configured in a C-shape that includes three sections: a Section A that is substantially parallel with the lumen of the proximal duodenum and antrum, a Section B that is substantially parallel with the descending duodenum, and a Section C that is substantially parallel with the third part of the duodenum and extends into the fourth part of the duodenum. In some embodiments, the bypass sleeve 1903 surrounds a portion of at least one anchor section, other embodiments in which the sleeve lies alongside the anchor sections are within the scope of this invention. At least one sliding seal 1904 may be configured to directly support the proximal opening of intestinal bypass sleeve 1903 via an expandable sleeve support 1905. The anchor 1900 supports sliding seal 1904 largely within the duodenal bulb, however other embodiments are possible in which the sliding seal is located in the antrum of the stomach, or more distally in the duodenum. A connecting structure 1906 may attach one anchor section to an expandable sleeve support 1905.

Figure 20:
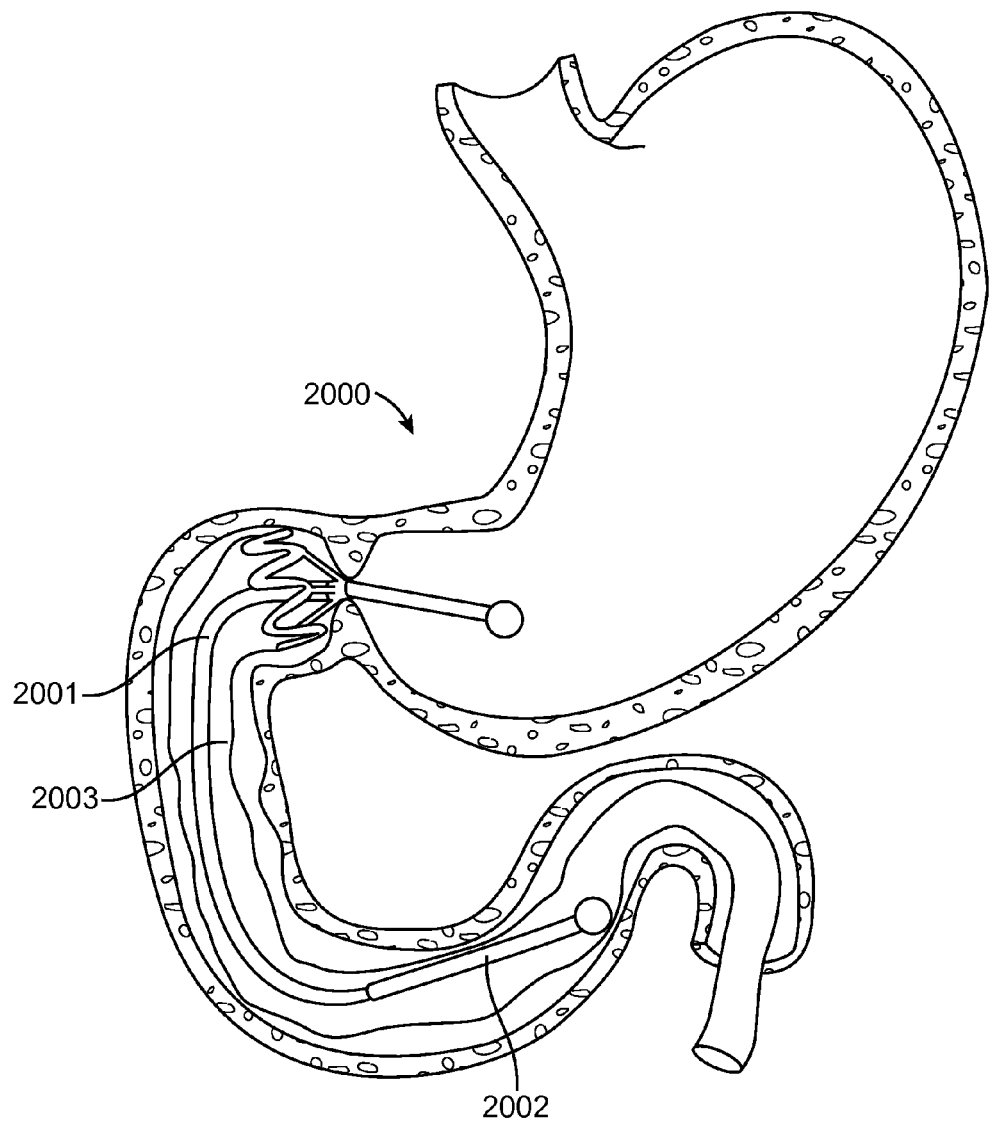
FIG. 20 is a view of a sectioned stomach and intestine with an intragastric anchor having a flexible portion, in accordance with many embodiments.

FIG. 20 depicts a gastroduodenal anchor 2000 including a relatively flexible section 2001 that may deflect to conform to the approximate shape of the duodenum and a relatively rigid section 2002 that resists deformation. The duodenal anchor may extend from the pylorus to the distal duodenum. Rigid section 2002 should be approximately 30 mm to 80 mm in length to prevent passage through the tight turn and relatively fixed geometry of the duodenal-jejunal juncture. Flexible section 2001 is configured to provide longitudinal support to intestinal bypass sleeve 2003 holding its proximal opening in the proximal duodenum or gastric antrum.

Figure 21:
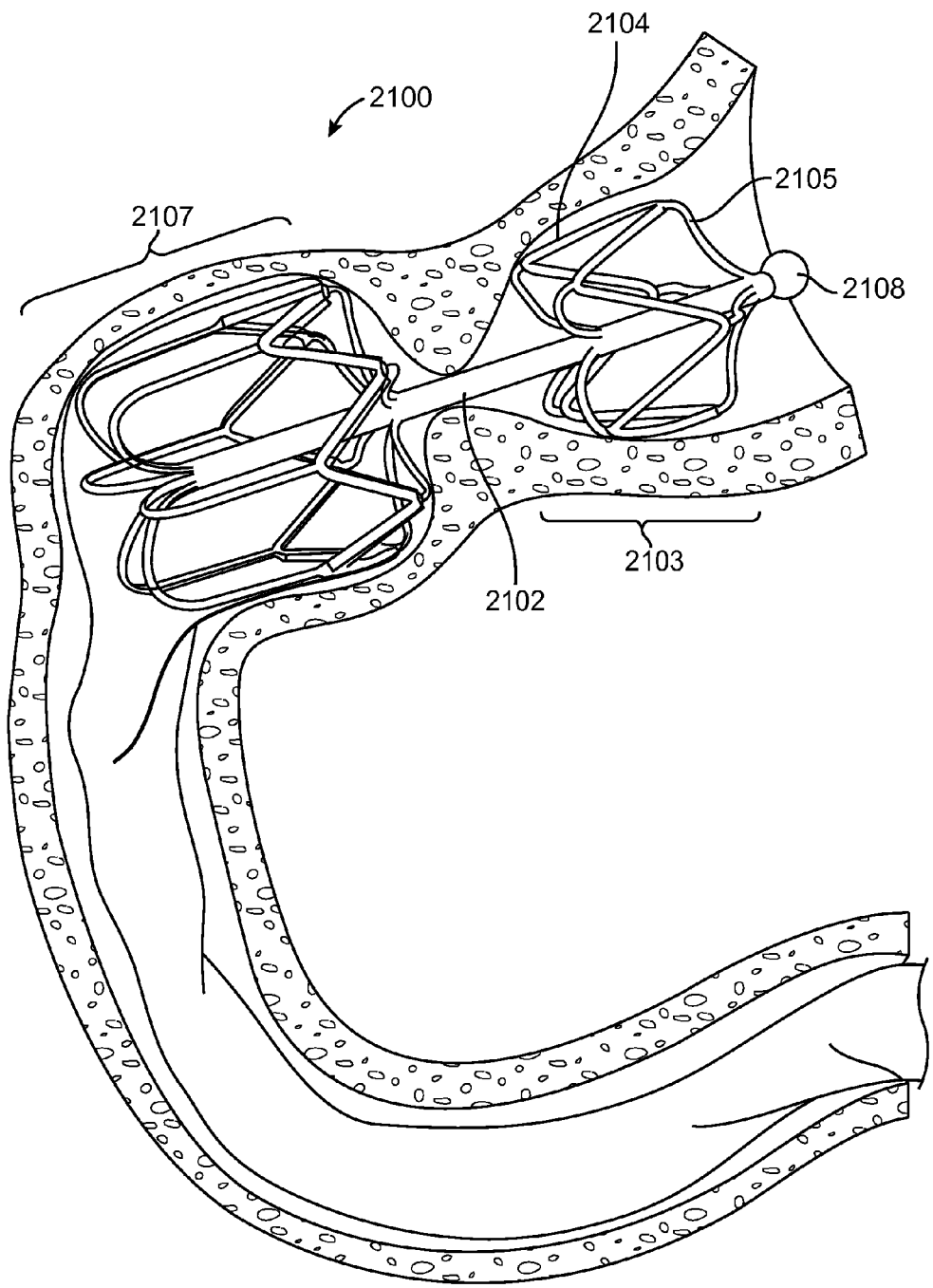
FIG. 21 is a view of a sectioned stomach and intestine with an intragastric anchor having a proximal atraumatic tip and a proximal and distal expandable structure, in accordance with many embodiments.

FIG. 21 depicts an embodiment of an intragastric anchor implant 2100 with a rod 2102 separating a proximal atraumatic tip 2103 and a distal atraumatic tip 2107. The proximal atraumatic tip 2103 may include an expandable 2104 structure which may increase its surface area and serve to spread mechanical loads. The expandable structure may include supporting struts 2105 which are biased distally such that the expandable structure may radially compress as it is withdrawn through narrow portions of the GI tract. The proximal atraumatic tip may also include a snaring feature 2108 which may easily be endoscopically snared such that tension may be applied to the anchor implant 2100 such that it may be withdrawn from the GI tract.

Figure 22A:
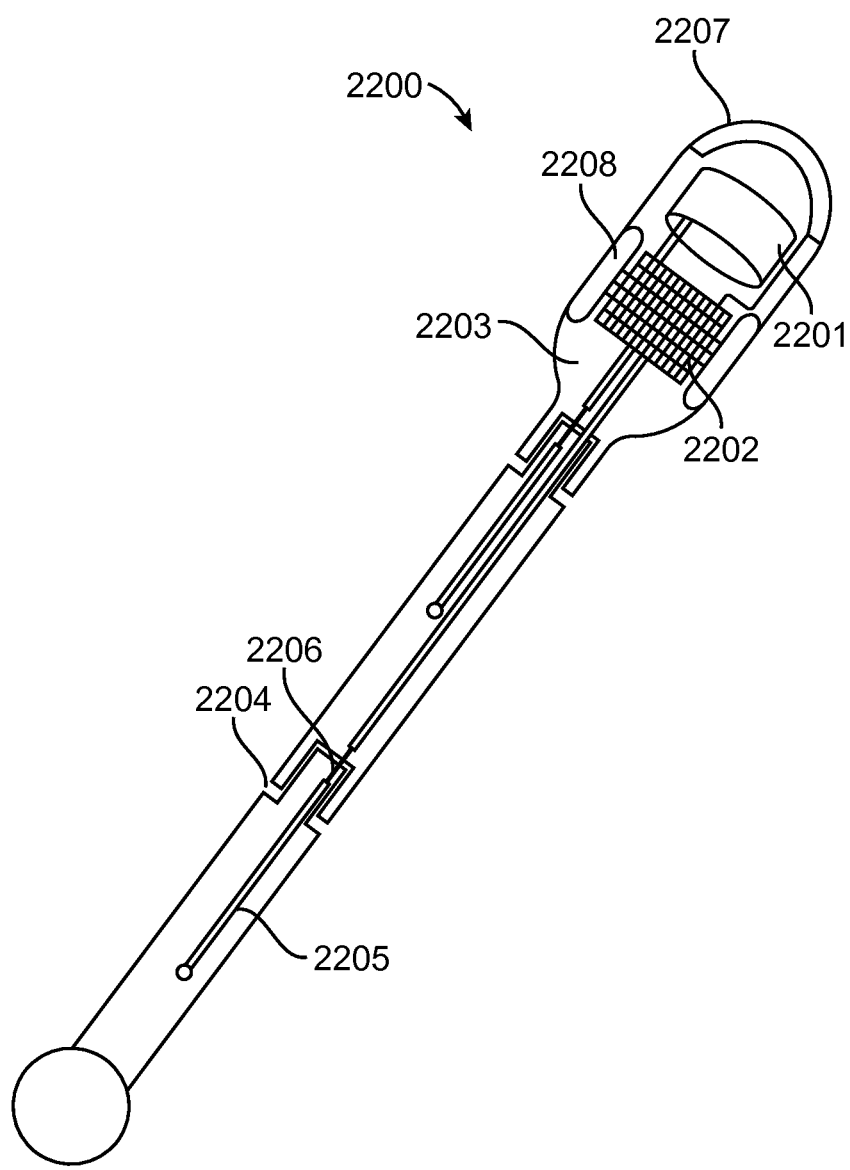
FIG. 22A is a view of a an intragastric anchor having at least one sensor, in accordance with many embodiments.

In certain circumstances it may be advantageous to implant an intragastric anchor without an intestinal bypass sleeve. Such an anchor may serve as a platform to support one or more sensors such as a camera, pH sensor, pressure sensor, or any type of sensor which might be advantageous to place within the GI tract. In its simplest form, a platform anchor may consist of a distal atraumatic tip and proximal atraumatic tip separated by a rod whereby either atraumatic tip, the rod, or a combination thereof may contain sensors, power supplies, or control electronics. In a more preferable embodiment, as shown in FIG. 22A, the platform anchor implant 2200 may be frangible into two or more segments after a desired period of time, de-anchoring the anchor implant such that relatively small segments of the anchor that may pass naturally out of the GI tract.

Figure 22B:
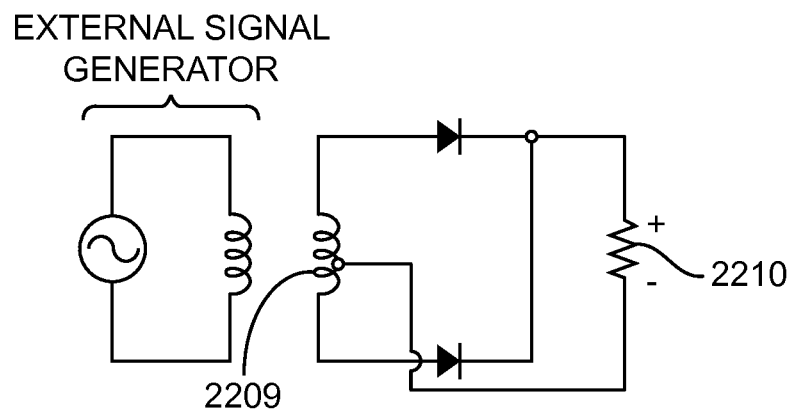
FIG. 22B is a diagram showing an inductive coupling between a transmitter and an intragastric anchor having at least one sensor, in accordance with many embodiments.

Electrolytic erosion may be employed to selectively time the de-anchoring of an anchor implant. As shown in FIG. 22A, at least one segment 2203 may include a local power source 2201 which may be a chemical battery such as a button battery, or which may be an inductive coil 2209 configured to be energized by an inductively-coupled external transmitter (as shown schematically in FIG. 22B). The local power source 2201 may provide electrical power to at least one sensor 2208 and may also provide power for de-anchoring through electrolytic erosion. The time of de-anchoring may be determined by electronics 2201 which may include at least one on-board microprocessor or de-anchoring may be initiated externally via induction whereby at least one segment contains a coil or antenna capable of inductive coupling. Segment joints 2204 may be held together by a small-gauge insulated wire 2205 such as 0.005 inch diameter stainless steel anchored to a segment at a distal portion of the wire. An uninsulated portion 2206 of insulated wire 2205 at or near a joint may be exposed to GI tract fluid such that an electrically conductive path 2210 is formed between the uninsulated portion of the wire 2206 and a relatively large electrode 2207 located on another part of the anchor implant. The joint may be separated by electrolytic erosion of the uninsulated section of wire by applying a voltage of +2.5V with a current of 5 mA to it relative to the large electrode 2207 for several minutes. Multiple joints may be separated approximately simultaneously or sequentially.

Figure 22C:
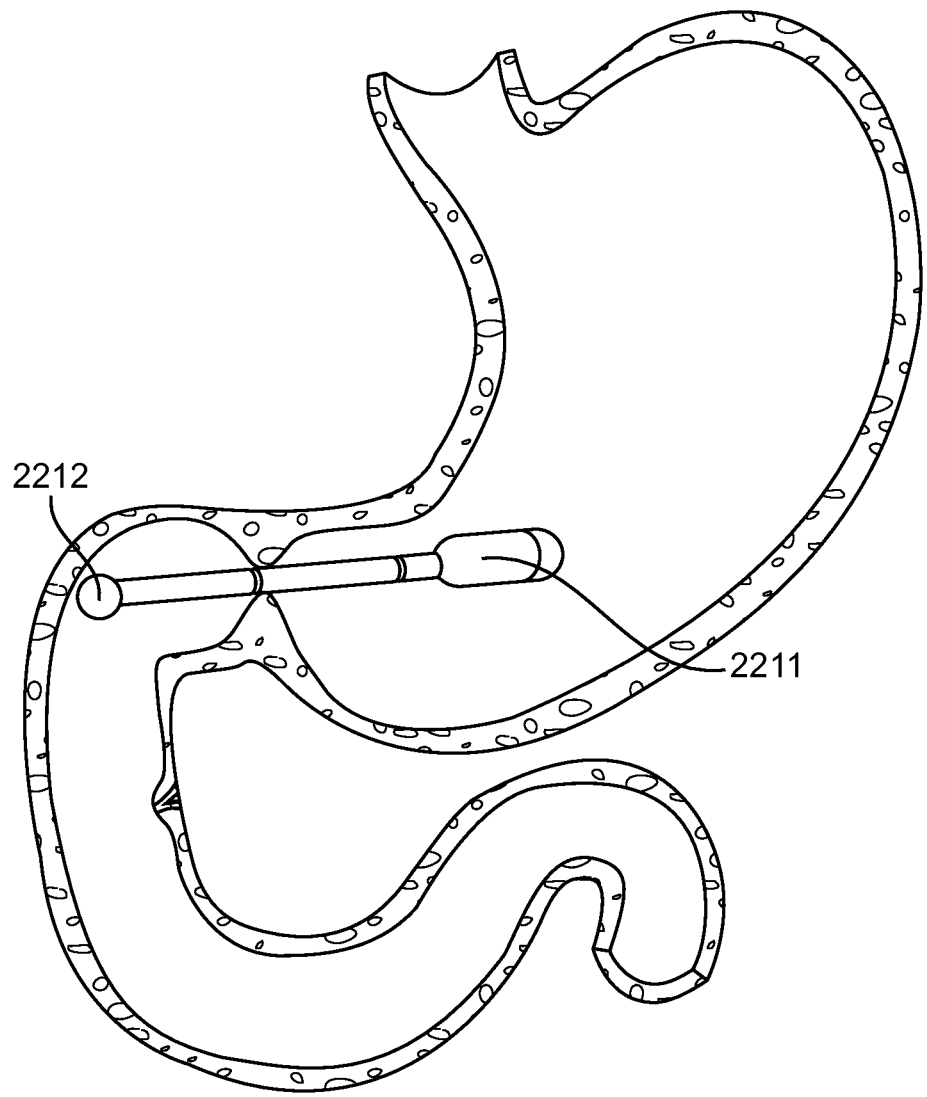
FIG. 22C is a view of a sectioned stomach and intestine with a frangible intragastric anchor having a at least one sensor, in accordance with many embodiments.

As depicted in FIG. 22C, a frangible anchor implant may be sized to anchor a sensor package across the pyloric valve. In such a configuration it may be advantageous to include sensors such as a camera or a pH sensor at the proximal atraumatic tip 2211, or at the distal atraumatic tip 2212.

Figure 22D:
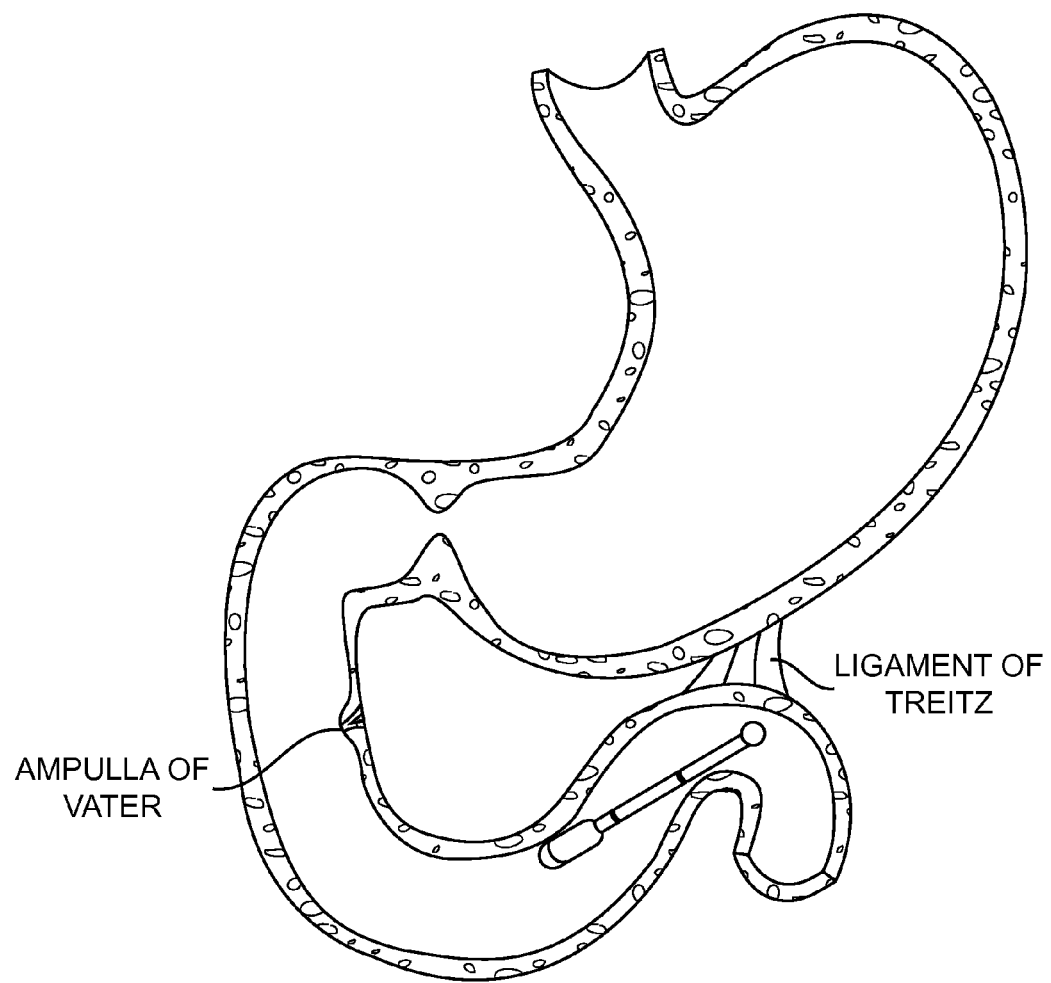
FIG. 22D is a view of a sectioned stomach and intestine with a frangible intragastric anchor having a at least one sensor sized for passing out of the stomach and anchoring at the duodenal-jejunal juncture, in accordance with many embodiments.

As depicted in FIG. 22D, a frangible anchor implant may be configured to pass out of the stomach and geometrically anchor at the duodenal-jejunal juncture where the Ligament of Treitz produces a sharp, relatively fixed turn in the small bowel. This position, distal to the Ampulla of Vater, may be advantageous for sensor placement as the characteristics of pancreatic and bile juices may be monitored.

Although the exemplary embodiments have been described in some detail for clarity of understanding and by way of example, a variety of additional modifications, adaptations and changes may be clear to those of skill in the art. One of skill in the art will appreciate that the various features described herein may be combined with one another or substituted with one another. Hence, the scope of the present invention is limited solely by the appended claims.

What is claimed is:

1. A method for treating and/or diagnosing a patient, said method comprising:
    providing an anchor having a proximal atraumatic feature at a proximal end and a distal atraumatic feature at or adjacent a distal end with an elongate element extending therebetween, wherein the anchor includes a first radially expandable structure between the proximal and distal end of the elongate element and proximal of the distal atraumatic feature;
    positioning the anchor within the gastrointestinal tract such that the distal atraumatic feature is within or adjacent the duodenum;
    deploying the anchor within a gastrointestinal tract of the patient, by expanding the first radially expandable structure; and
    inhibiting advancement of the deployed anchor around a bend of the gastrointestinal tract by engaging a proximal portion of the anchor against a first surface area of a mucosa of the gastrointestinal tract and by engaging a distal portion of the anchor against a second surface area of a mucosa of the gastrointestinal tract distal of the first mucosal surface area, and by resisting bending of the elongate element extending between the proximal and distal ends such that the distal atraumatic feature is maintained within the duodenum; and
    supporting an intestinal bypass sleeve of the implant with the anchor so that the sleeve extends along an intestine of the patient while a proximal opening of the intestinal bypass sleeve is maintained within the duodenum so that a flow including ingested matter enters a lumen of the sleeve from a stomach of the patient, the flow being in contact with a wall of the stomach of the patient.

2. The method of claim 1, the method further comprising:
    directing the flow of ingested matter into the sleeve by radially supporting a proximal opening of the sleeve with the first radially expandable structure and circumferentially engaging a wall of the sleeve against an inner wall of the gastrointestinal tract with the radially expandable structure of the anchor.

3. The method of claim 2, wherein the first radially expandable structure comprises a slidable seal that is slidable within the gastrointestinal tract in or adjacent a duodenal bulb of the gastrointestinal tract.

4. The method of claim 2, wherein the distal atraumatic feature comprises a second radially expandable support structure.

5. The method of claim 2, wherein the distal atraumatic feature comprises the first radially expandable support structure.

6. The method of claim 3, wherein supporting the proximal opening of the sleeve comprises expanding the first expandable structure within the gastrointestinal tract within the duodenum in or adjacent the duodenal bulb.

7. The method of claim 6, wherein directing a flow through the sleeve further comprises:
    urging the proximal opening of the sleeve toward a pyloric valve of the gastrointestinal tract by supporting the proximal opening of the sleeve with a circumferential seal biased in the proximal direction.

8. The method of claim 7, wherein urging the proximal opening of the sleeve toward the pyloric valve comprises supporting the proximal opening with a proximal portion of the first expandable member while a distal portion of the expandable member engages a distal portion of the duodenal bulb.

9. The method of claim 6, wherein anchoring the sleeve further comprises:
    expanding a second radially expandable structure proximal of the first radially expandable structure so as to engage a tissue proximal of a pyloric valve of the gastrointestinal tract to inhibit distal movement of the anchor along the gastrointestinal tract of the patient.

10. The method of claim 2, wherein when the first expandable structure is expanded in a duodenal bulb of the gastrointestinal tract, the second expandable structure is positioned adjacent the first expandable structure proximal of a pyloric valve of the gastrointestinal tract.

11. The method of claim 2, wherein the first expandable support structure is disposed on the elongate element of the anchor between proximal and distal ends.

12. The method of claim 11, wherein the elongate element includes a flexible portion and/or a curved portion between proximal and distal ends.

13. The method of claim 1, wherein the anchor comprises one or more sensors attached thereto, the method further comprising:
    sensing a property of the gastrointestinal tract with the one or more sensors.

14. The method of claim 13, wherein the anchor comprises two or more separable segments, the method further comprising:
    de-anchoring the anchor by separating the at least two separable segments thereby allowing one or more of the separable segments to pass distally through the gastrointestinal tract.

15. The method of claim 14, wherein de-anchoring further comprises selectively timing the de-anchoring of the at least two separable segments through electrolytic erosion.

16. An implant for use in a gastrointestinal tract of a patient, said implant comprising:
an anchor having a proximal atraumatic feature at the proximal end, a distal atraumatic feature at the distal end, and an elongate element extending therebetween;
wherein the proximal and distal atraumatic features are configured to inhibit tissue trauma when urged against a surface area along a mucosa in the gastrointestinal tract of the patient, and wherein flexibility of the elongate element is limited so as to resist bending between the proximal and distal ends so as to inhibit advancement of the anchor around a bend of the gastrointestinal tract,
wherein the anchor include a first radially expandable structure between the proximal and distal ends and proximal of the distal atraumatic feature, the first radially expandable structure being dimensioned to sit within the duodenum within or adjacent a duodenal bulb of the gastrointestinal tract when expanded therein so as to maintain the distal atraumatic feature within the duodenum; and
an intestinal bypass sleeve supported with the anchor so that the sleeve extends along an intestine of the patient while a proximal opening of the intestinal bypass sleeve is maintained within the duodenum so that a flow including ingested matter enters a lumen of the sleeve from a stomach of the patient.

17. The implant of claim 16, wherein the first radially expandable structure is dimensioned to substantially fill a duodenal bulb of the gastrointestinal tract when expanded therein.

18. The implant of claim 16,
wherein the intestinal bypass sleeve is coupled to the first expandable structure so as to extend at least partially through the gastrointestinal tract.

19. The implant of claim 18, wherein the sleeve comprises a material substantially impenetrable to a flow including ingested matter when passed through the lumen, the flow of matter being in contact with a wall of a stomach of the patient.

20. The implant of claim 16, wherein the distal atraumatic feature comprises the first radially expandable structure and the anchor comprises a second radially expandable structure proximal of the first radially expandable structure, the second radially expandable structure dimensioned so as to engage a tissue proximal of a pyloric valve of the gastrointestinal tract when expanded so as to inhibit distal movement of the anchor along the gastrointestinal tract of the patient.

21. The implant of claim 16, wherein the elongate element comprises at least two bends so as to conform to a shape of the gastrointestinal tract.

22. The implant of claim 18, wherein the distal atraumatic feature comprises the first radially expandable structure.

23. The implant of claim 18, wherein the elongate element is substantially rigid and comprises one or more bends so as to further anchor and conform to a shape of the gastrointestinal tract.

24. The implant of claim 18, wherein the first radially expandable structure comprises a circumferential seal supporting a proximal opening of an intestinal bypass sleeve while maintained within the duodenum so as to allow a flow of ingested materials from a stomach of the patient to pass therethrough.

25. The implant of claim 24, wherein the circumferential seal is disposed on a proximal portion of the first radially expandable structure so as to position the proximal opening of the sleeve nearest a pyloric valve when the first expandable structure is expanded within the duodenal bulb.

26. The implant of claim 25, wherein the first expandable structure comprises space-filling struts extending along a distal portion of the first expandable structure so as to position the circumferential seal nearest the pyloric valve when expanded within the duodenal bulb.

27. The implant of claim 25, wherein the circumferential seal comprising a sinusoidal member of the expandable structure.

28. The implant of claim 25, wherein the circumferential seal comprises any of a ziz-zag member, a diamond shaped member, a multi-link structure, a plurality of flexible arms, or an expandable ring configuration suitable for supporting the proximal opening of the sleeve.

29. The implant of claim 24, wherein the circumferential seal comprises a sliding seal that circumferentially engages an outer wall of the sleeve against an inner wall of the duodenal bulb so as to maintain the seal while allowing slight movement of the first expandable structure along the gastrointestinal tract.

30. The implant of claim 24, wherein the first expandable structure comprises a proximal portion and a distal portion, wherein the proximal portion comprises the circumferential seal nearest a pyloric valve of the gastrointestinal tract when the first expandable structure is expanded within the duodenal bulb.

31. The implant of claim 24, wherein the circumferential seal is configured so as to urge the circumferential seal in the proximal direction when the first expandable structure is under radial compression.

32. The implant of claim 31, wherein the circumferential seal is supported with curved struts.

33. The implant of claim 32, wherein the curved struts are curved such than an apex of curvature points in a proximal direction such that radial compression of the expandable structure urges the circumferential seal in the proximal direction.

34. The implant of claim 24, wherein the distal atraumatic feature comprises a second expandable structure.

35. The implant of claim 34, wherein the first and second expandable structure are axially spaced apart by a distance sufficiently large enough to accommodate a pyloric valve of the gastrointestinal tract and sufficiently small enough that the first expandable structure engages a tissue adjacent the pyloric valve so as to inhibit distal movement of the implant while the expanded second expandable structure is disposed within the duodenal bulb.

36. The implant of claim 16, wherein the elongate element comprises a flexible portion so as to allow the anchor to accommodate a curvature of the gastrointestinal tract.

37. The implant of claim 16, wherein the elongate element comprises at least three elongate members attached in series in a shape corresponding to different portions of the gastrointestinal tract, wherein the at least three elongate members includes a first elongate member corresponding to an antrum and proximal duodenum of the gastrointestinal tract, a second elongate member attached thereto and corresponding to a descending portion of the duodenum and a third elongate member attached thereto and corresponding to a third portion of the duodenum.

38. The implant of claim 16, further comprising:
an intestinal bypass sleeve coupled to the first expandable anchor, wherein the sleeve extends at least partially through the gastrointestinal tract, the intestinal bypass sleeve having a lumen extending therethrough from a proximal opening to a distal opening.

39. The implant of claim 16, further comprising:
one or more sensors attached to the anchor, the one or more sensors configured to sense a property of the gastrointestinal tract when disposed therein.

40. The implant of claim 39, wherein the anchor comprises two or more separable segments, at least one of the separable segments sized so as to be passed through the gastrointestinal tract of the patient and wherein the two or more separable segments are coupled so as to be selectively de-coupled from outside a body of the patient.

* * * * *